United States Patent
Xiong et al.

(10) Patent No.: US 12,054,527 B2
(45) Date of Patent: Aug. 6, 2024

(54) GROWTH DIFFERENTIATION FACTOR 15 FUSION PROTEINS

(71) Applicant: Amgen Inc., Thousand Oaks, CA (US)

(72) Inventors: YuMei Xiong, Palo Alto, CA (US); Kenneth William Walker, Newbury Park, CA (US); Murielle Marie Veniant Ellison, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 1164 days.

(21) Appl. No.: 16/620,029

(22) PCT Filed: Apr. 8, 2019

(86) PCT No.: PCT/US2019/026369
§ 371 (c)(1),
(2) Date: Dec. 6, 2019

(87) PCT Pub. No.: WO2019/199685
PCT Pub. Date: Oct. 17, 2019

(65) Prior Publication Data
US 2023/0143988 A1  May 11, 2023

Related U.S. Application Data

(60) Provisional application No. 62/655,108, filed on Apr. 9, 2018.

(51) Int. Cl.
C07K 14/495 (2006.01)
A61K 38/00 (2006.01)

(52) U.S. Cl.
CPC ............ C07K 14/495 (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 6,737,056 B1 | 5/2004 | Presta | |
| 7,271,149 B2 | 9/2007 | Glaesner et al. | |
| 8,338,569 B2 | 12/2012 | Marshall et al. | |
| 8,362,210 B2 | 1/2013 | Lazar et al. | |
| 8,372,952 B2 | 2/2013 | Smith et al. | |
| 8,629,244 B2 | 1/2014 | Kolkman et al. | |
| 9,161,966 B2 | 10/2015 | Matern et al. | |
| 9,248,181 B2 | 2/2016 | De Kruif | |
| 9,272,019 B2 | 3/2016 | Shaw et al. | |
| 9,550,819 B2 | 1/2017 | Lindhout | |
| 9,714,276 B2 | 7/2017 | Xiong et al. | |
| 9,827,291 B2 | 11/2017 | Matern et al. | |
| 9,828,415 B2 | 11/2017 | Matern et al. | |
| 9,834,586 B2 | 12/2017 | Lindhout et al. | |
| 9,862,752 B2 | 1/2018 | Xiong et al. | |
| 9,920,118 B2 | 3/2018 | Shen et al. | |
| 10,195,250 B2 * | 2/2019 | Lindhout | C07K 14/495 |
| 10,336,798 B2 | 7/2019 | Xiong et al. | |
| 10,336,812 B2 | 7/2019 | Armstrong et al. | |
| 10,752,664 B2 * | 8/2020 | Xiong | A61P 3/00 |
| 10,894,814 B2 | 1/2021 | Xiong et al. | |
| 11,161,889 B2 | 11/2021 | Xiong et al. | |
| 11,208,464 B2 * | 12/2021 | Armstrong | A61K 47/65 |
| 11,739,131 B2 | 8/2023 | Xiong et al. | |
| 2004/0053366 A1 | 3/2004 | Lo et al. | |
| 2006/0275283 A1 | 12/2006 | Van Vlijmen et al. | |
| 2007/0054853 A1 | 3/2007 | Fujise et al. | |
| 2009/0004181 A1 | 1/2009 | Breit | |
| 2009/0042780 A1 | 2/2009 | Knopf et al. | |
| 2010/0087627 A1 | 4/2010 | Marshall et al. | |
| 2010/0278843 A1 | 11/2010 | Breit et al. | |
| 2011/0150901 A1 | 6/2011 | Smith et al. | |
| 2011/0195067 A1 | 8/2011 | Arnason et al. | |
| 2011/0229472 A1 | 9/2011 | Min et al. | |
| 2011/0236375 A1 | 9/2011 | Lazar et al. | |
| 2013/0336981 A1 | 12/2013 | De Kruif et al. | |
| 2014/0213511 A1 * | 7/2014 | Matern | C07K 16/22 514/6.9 |
| 2015/0023960 A1 | 1/2015 | Lindhout et al. | |
| 2015/0139996 A1 | 5/2015 | De Kruif et al. | |
| 2015/0307575 A1 | 10/2015 | Xiong | |
| 2016/0031960 A1 | 2/2016 | Lindhout et al. | |
| 2016/0030585 A1 | 3/2016 | Barnes et al. | |

(Continued)

FOREIGN PATENT DOCUMENTS

| | | |
|---|---|---|
| CN | 1723220 A | 1/2006 |
| CN | 1974601 A | 6/2007 |

(Continued)

OTHER PUBLICATIONS

"Metabolic Disease," Encyclopedia Britannica, https://www.britannica.com/science/metabolic-disease; accessed Jul. 21, 2023).*
Arnold, The Impact of Glycosylation on the Biological Function and Structure of Human Immunoglobulins, Annual Rev. Immunol; 25: 21-50, 2007.
Wang, IgG Fc engineering to modulate antibody effector functions; Protein Cell, 9(1): 63-73, 2018.
Abma (Blood Sugar Monitoring: When to Check and Why, 2009).
Alain et al., Therapeutic Fc-fusion proteins and peptides as successful alternatives to antibodies, MABS, 2011, 3:5, 415-416.
American Diabetes Association Standards of Medical Care in Diabetes Care—2011.
Ansel et al., Pharmaceutical Dosage Forms & Drug Delivery Systems, 7th ed. 2000.
Aulton, Pharmaceutics: The Science of Dosage Form Design, Churchill Livingstone, New York, 1988.
Ausubel et al., eds., Current Protocols in Molecular Biology, Green Publishers Inc. and Wiley and Sons, 1994.

(Continued)

*Primary Examiner* — Elizabeth C. Kemmerer
(74) *Attorney, Agent, or Firm* — Amy C. Madl

(57) ABSTRACT

GDF15 molecules are provided herein. In some embodiments, the GDF15 molecule is a GDF15-Fc fusion, in which a GDF15 region is fused to an Fc region. In some embodiments, the GDF15 region is fused to the Fc region via a linker. Also, provided herein are methods for making and using GDF15 molecules.

19 Claims, 10 Drawing Sheets

Specification includes a Sequence Listing.

(56) References Cited

U.S. PATENT DOCUMENTS

| | | |
|---|---|---|
| 2016/0120999 A1 | 5/2016 | Shen et al. |
| 2016/0129082 A1 | 5/2016 | Matern et al. |
| 2016/0200787 A1 | 7/2016 | Matern et al. |
| 2017/0107248 A1 | 4/2017 | Lou et al. |
| 2017/0204149 A1 | 7/2017 | Chopra et al. |
| 2017/0299608 A1 | 10/2017 | Hsu et al. |
| 2018/0079790 A1 | 3/2018 | Xiong et al. |
| 2019/0000923 A1 | 1/2019 | Chutkow et al. |
| 2019/0248852 A1 | 8/2019 | Zhang et al. |
| 2019/0292241 A1 | 9/2019 | Armstrong et al. |
| 2019/0309033 A1 | 10/2019 | Gonciarz et al. |
| 2021/0079051 A1 | 3/2021 | Xiong et al. |
| 2022/0152154 A1 | 5/2022 | Xiong et al. |

FOREIGN PATENT DOCUMENTS

| | | |
|---|---|---|
| EP | 0036676 A1 | 9/1981 |
| EP | 0036776 A2 | 9/1981 |
| EP | 0058481 A1 | 8/1982 |
| EP | 0088046 A2 | 9/1983 |
| EP | 0133988 A2 | 3/1985 |
| EP | 0143949 B1 | 10/1988 |
| EP | 2330197 A2 | 6/2011 |
| EP | 2439535 A1 | 4/2012 |
| EP | 2694092 B1 | 1/2017 |
| JP | 2003081831 A | 3/2003 |
| JP | 2007532586 A | 11/2007 |
| JP | 2010536717 A | 12/2010 |
| WO | 199315722 A1 | 8/1993 |
| WO | 199906445 A1 | 8/2005 |
| WO | 2005077981 A2 | 8/2005 |
| WO | 2005099746 A1 | 10/2005 |
| WO | 2006000448 A2 | 1/2006 |
| WO | 2007041635 A2 | 4/2007 |
| WO | 2009021293 A8 | 2/2009 |
| WO | 2009089004 A1 | 7/2009 |
| WO | 2009141357 A1 | 11/2009 |
| WO | 2010017198 A2 | 2/2010 |
| WO | 2010048670 A1 | 5/2010 |
| WO | 2011/063348 A1 | 5/2011 |
| WO | 2011064758 A2 | 6/2011 |
| WO | 2012138919 A1 | 10/2011 |
| WO | 2012007868 A2 | 1/2012 |
| WO | 2012007869 A2 | 1/2012 |
| WO | 2012007877 A2 | 1/2012 |
| WO | 2012025355 A1 | 3/2012 |
| WO | 2012058768 A1 | 5/2012 |
| WO | 2012125850 A1 | 9/2012 |
| WO | 2012146628 A1 | 11/2012 |
| WO | 2013113008 A1 | 8/2013 |
| WO | 2013148117 A1 | 10/2013 |
| WO | 2013157953 A1 | 10/2013 |
| WO | 2013157954 A1 | 10/2013 |
| WO | 2014100689 A1 | 6/2014 |
| WO | 2014/120619 A2 | 8/2014 |
| WO | 2015/198199 A1 | 12/2015 |
| WO | 2016/069921 A1 | 5/2016 |

OTHER PUBLICATIONS

Aronne, Treating Obesity: A New Target for Prevention of Coronary Heart Disease (Prog Cardiovasc Nurs. 2001 ;16(3)).
Baek SJ, J. Biol Chemistry, 2001, 276:33384-33392.
Baek SJ, Gastroenterology, 2006, 131:1553-1560.
Bauskin AR, EMBO J., 2000, 19:2212-2220; NCBI.
Beck et al., "Therapeutic Fc-fusion proteins and peptides as successful alternatives to antibodies," MABS, 3(5):415-416 (2011).
Berge et al., "Pharmaceutical Salts", J. Pharm. Science, 1977, 6661, 1-19.
Biotek (Determination of Insulin Levels in Human Serum, 2009).
Bootcov MR, 1997, Proc Natl Acad Sci 94:11514-11519.
Bottner M , Gene, 1999, 237:105-11.
Carrillo et al., SIAM J. Applied Math., 1988, 48:1073.
Cekanova M, "Nonsteroidal anti-inflammatory drug-activated gene-1 expression inhibits urethane-induced pulmonary tumorigenesis in transgenic mice", 2009, Cancer Prev Res 2:5, 450-458.
Computational Molecular Biology, Lesk, A. M., ed., 1988, New York: Oxford University Press; Biocomputing Informatics and Genome Projects, Smith, D. W., ed., 1993, New York: Academic Press.
Creative BioMart, Recombinant Human Growth Differentiation Factor 15. Fe Chimera; Oct. 23, 2010 (according to document properties for posted document); (Retrieved from the Internet Apr. 9, 2013 http://img.creativebiomart.netlpdf/GDF15-204H.GDF15 ,F c%20Chimera. pdf>.
Czajkowsky, et al., EMBO Mol Med, Epub, 2012 4(10), 1015-1028.
Czajkowsky, et al., "Fc-fusion proteins: new developments and future perspectrives". EMBO Mol Med, Epub, 2012 4(10), 1015-1028.
Dayhoff et al., Atlas of Protein Sequence and Structure, 1978, 5:345-352.
Devereux et al., Nucl. Acid Res. 1984, 12:387.
Diabetes self-management (downloaded online from URL:<http://www.diabetesselfmanagement.com/diabetesresources/definitions/prediabetes/>, 2006).
Dinsmoor (downloaded online from URL:<http://www.diabetesselfmanagement.com/managing-diabetes/complicationsprevention/protecting-your-kidneys/, 2009).
Dostalova, et al.: Increased serum concentrations of macrophage inhibitory cytokine-1 in patients with obesity and type 2 diabetes mellitus: the influence of very low calorie diet.: European Journal of Endocrinology /European Federation of Endocrine Societies Sep. 2009, vol. 161 No. 3, (Sep. 2009), pp. 397-404.
Epstein et al., Proc. Natl. Acad. Sci. US, 1985, 82: 3688-3692.
Fairlie WD, Gene, 2000, 254: 67-76.
Freiberg & Zhu, Int. J. Pharm., 2004, 282:1-18.
GenBank: AF003934.1 (Homo sapiens prostate differentiation factor mRNA, complete cds, 1997).
Gribskov, M. and Devereux, J., eds., Sequence Analysis Primer, 1991, New York: M. Stockton Press.
Griffin, A. M., and Griffin, H. G., eds., Computer Analysis of Sequence Data, Part I, 1994, New Jersey: Humana Press.
Henikoff et al., Proc. Natl. Acad. Sci. USA 1992, 89:10915-10919.
Hromas R., Biochim Biophys Acta. 1997, 1354:40-44.
Inoue et al., Nat Med. Feb. 2004; 10(2):168-74.
Jenson, et al. "A novel Fc gamma receptor ligand augments humoral responses by targeting antigen to Fc gamma receptors", Eur. J. Immunol, 2007, 37:4, 1139-1148.
Johnen H, Nat Med., 2007, 11:1333-1340.
Katoh M, Int J Mol Med, 2006. 17:951-955.
Kempf T, "The Transforming Growth Factor-{szligbeta} Superfamily Member Growth-Differentiation Factor-15 Protects the Heart From Ischemia/Reperfusion Injury", Circ Res., 2006, 98:351-360.
Lajer Maria, et al.: "Plasma growth differentiation factor-15 independently predicts all-cause and cardiovascular mortality as well as deterioration of kidney function in type 1 diabetic patients with nephropathy.", Diabetes Care, vol. 33, No. 7, Jul. 2010 (Jul. 2010), pp. 1567-1572.
Langer et al., J. Biomed. Mater. Res., 1981, 15:167-277.
Langer, Chem. Tech., 1982, 12: 98-105.
Lawton LN, "Identification of a novel member of the TGF-beta superfamily highly expressed in human placenta", Gene, 1997, 203:17-26.
Lind et al.: "Growth-differentiation factor-15 is an independent marker of cardiovascular dysfunction and disease in the elderly; results from the Prospective Investigation of the Vasculature in Uppsala Seniors (PIVUS) Study", European Heart Journal (Online), Oxford University Press, GB, US, NI., vol. 30, No. 19, Oct. 1, 2009 (Oct. 1, 2009), pp. 2346-2353.
Lo et al. (2005, Protein Engineering, Design & Selection 18:1-10).
Macia L. et al., PLoS One., Apr. 13, 2012, vol. 7, No. 4, pp. e34868.
Mekhaiel, et al. "Polymeric human Fc-fusion proteins with modified effector functions", 2011, Sci Rep. 1:124.

(56) References Cited

OTHER PUBLICATIONS

Moore A.G., "The transforming growth factor-ss superfamily cytokine macrophage inhibitory cytokine-1 is present in high concentrations in the serum of pregnant women", J Clin Endocrinol Metab, 2006, 85: 4781-4788.
NCBI Reference Sequence: NP 004855.2 (Jan. 13, 2011).
Needleman et al., J. Mol. Biol., 1970, 48:443-453.
Paralkar VM, "Cloning and characterization of a novel member of the transforming growth factor-beta/bone morphogenetic protein family", J. Biol. Chemistry, 1998, 273:13760-13767.
Remington: The Science and Practice of Pharmacy, 19th edition, 1995.
Rose-John et al., "The IL-6/sIL-6R complex as a novel target for therapeutic approaches," Expert Opinion on Therapeutic Targets, 11:5, 613-624 (2007).
Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N.Y., 1989.
Sidman et al., Biopolymers 1983, 22: 547-56.
Sino Biological Inc. (http:/ww.sinobiological.com/GDF-15-Protein-g-570.html; available May 1, 2010).
Smith, D. W., ed, Biocomputing Informatics and Genome Projects, 1993, New York: Academic Press.
Strelau J, "Progressive Postnatal Motoneuron Loss in Mice Lacking GDF-15", J Neuroscience, 2009, 29:13640-13648.
Tamary H, "", Blood, 2008, 112:5241-5244.
Tanno T, "High levels of GDF15 in thalassemia suppress expression of the iron regulatory protein hepcidin", Nat Med, 2007, 13:1096-1101.
Van Heeke & Schuster, "Expression of human asparagine synthetase in *Escherichia coli*", J. Biol. Chem., 1989, 264: 5503-5509.
Von Heinje, G., Sequence Analysis in Molecular Biology, 1987, New York: Academic Press.
White, "Design and expression of polymeric immunoglobulin fusion proteins: a strategy for target in low-affinity Fogamma receptors", Protein Expr, Purif, 2001, 21:3, 446-455.
White et al., "Rapid Immune Responses to a Botulinum Neurotoxin Hc Subunit Vaccine through in Vivo Targeting to Antigen-Presenting Cells," *Infect. Immun.*, Epub, 79(8):3388-3396 (2011).
Wilson and Gisvolds' Textbook of Organic Medicinal and Pharmaceutical Chemistry, Delgado and Remers, Eds., 10th ed., 1998.
Wischke & Schwendeman, Int. J. Pharm., 2008, 364: 298-327.
Xu J, "GDF15/MIC-1 Functions as a Protective and Antihypertrophic Factor Released From the Myocardium in Association With SMAD Protein Activation", Circ Res., 2006, 98:342-350.
Zimmermann MB, "Iron metabolism in heterozygotes for hemoglobin E (HbE), -thalassemia 1, or -thalassemia and in compound heterozygotes for HbE/-thalassemia", Am J Clin Nutr, 2008, 88:1026-1031.
K. Gunasekaran et al: "Enhancing Antibody 2-24 Fc Heterodimer Formation through Electrostatic Steering Effects: Applications to Bispecific Molecules and Monovalent IgG", Journal of Biological Chemistry, vol. 285, No. 25, Jun. 18, 2010 (Jun. 18, 2010), pp. 19637-19646.
International Search Report and Written Opinion for PCT Application No. PCT/US2019/026369, mailed on Jun. 13, 2019.

* cited by examiner

GROWTH DIFFERENTIATION FACTOR 15 FUSION PROTEINS

RELATED APPLICATIONS

This application is a U.S. national stage filing under 37 U.S.C. § 371 of PCT Application No. PCT/US2019/026369, filed on Apr. 8, 2019, which claims the benefit of U.S. Provisional Application No. 62/655,108, filed on Apr. 9, 2018, both of which are hereby incorporated by reference in their entireties.

SEQUENCE LISTING

The present application is being filed along with a Sequence Listing in electronic format. The Sequence Listing is provided as a file entitled A-2239-WO-PCT_SeqList_ST25.txt, created Mar. 15, 2019, which is 111,475 bytes in size. The information in the electronic format of the Sequence Listing is incorporated herein by reference in its entirety.

FIELD OF THE INVENTION

The instant disclosure relates to GDF15 molecules, such as GDF15 fusion proteins, compositions thereof, and methods for making and using such proteins.

BACKGROUND

Growth differentiation factor 15 (GDF15), also referred to as macrophage inhibitory cytokine 1 (MIC1) (Bootcov MR, 1997, *Proc Natl Acad Sci* 94:11514-9), placental bone morphogenetic factor (PLAB) (Hromas R 1997, *Biochim Biophys Acta.* 1354:40-4), placental transforming growth factor beta (PTGFB) (Lawton LN 1997, *Gene.* 203:17-26), prostate derived factor (PDF) (Paralkar VM 1998, *J Biol Chem.* 273:13760-7), and nonsteroidal anti-inflammatory drug-activated gene (NAG-1) (Baek SJ 2001, *J Biol Chem.* 276: 33384-92), is a secreted protein that circulates in plasma as an ~25 kDa homodimer. GDF15 binds to GDNF family receptor a-like (GFRAL) with high affinity. GDF15-induced cell signaling is believed to require the interaction of GFRAL with the coreceptor RET.

GDF15 has been linked to multiple biological activities. Elevated GDF15 has been shown to be correlated with weight loss and administration of GDF15 has been shown to reduce food intake and body weight. Accordingly, there is a need for efficacious GDF15 molecules that can be administered as a therapeutic. The present disclosure provides GDF15 molecules that meets this need and provide related advantages.

SUMMARY

Provided herein are GDF15 molecules, methods of making the molecules and methods of using the molecules. In some embodiments, the GDF15 molecule is a GDF15-Fc fusion protein. The fusion protein can comprise a GDF15 region joined to an Fc region. In some embodiments, the GDF15 region is joined to the Fc via a linker.

In some embodiments, the GDF15 region comprises the amino acid sequence of SEQ ID NO: 6 and at least one mutation, such as a mutation of the asparagine at position 3 (N3), as a mutation of the aspartate at position 5 (D5), or mutations of the asparagine at position 3 and the aspartate at position 5. In some embodiments, the GDF15 region comprises a mutation of the aspartate at position 5 to glutamate (D5E). In some embodiments, the GDF15 region comprises the amino acid sequence of SEQ ID NO: 16. In some embodiments, the GDF15 region comprises a mutation of the asparagine at position 3 to glutamine (N3Q), for example, having an amino acid sequence SEQ ID NO: 14. In yet other embodiments, the GDF15 region comprises both N3Q and D5E mutations. In some embodiments, the GDF15 region comprises the amino acid sequence of SEQ ID NO: 18.

In some embodiments, the fusion protein has a linker that is a G4S (SEQ ID NO: 19) or G4Q (SEQ ID NO: 24) linker, such as a (G4S)n or (G4Q)n linker, wherein n is greater than 0. In some embodiments, the fusion protein has a linker that is a G4A (SEQ ID NO: 58) linker, such as a (G4A)n linker, wherein n is greater than 0. In some embodiments, n is 1 or 2. In some embodiments, n is greater than 2, such as 3, 4, 5, 6, 7, or 8. In some embodiments, the linker comprises the amino acid sequence of SEQ ID NO: 19, 20, 21, 22, 23, 24, 25, or 58.

In some embodiments, the fusion protein has an Fc region comprises a charged pair mutation. In some embodiments, the Fc region has a truncated hinge region. In some embodiments, the Fc region is selected from Table 3.

Also provided herein are dimers and tetramers comprising the fusion proteins disclosed herein. In one embodiment, the dimer comprises a GDF15-Fc fusion comprising the amino acid sequence of any one of SEQ ID NOs: 39-57. In some embodiments, a GDF15-Fc fusion comprising the amino acid sequence of SEQ ID NO: 39, 40, 41, 42, 43, 44, 45, 46, 47, 48, 49, 50, 51, 52, 53, 54, 55, 56 or 57 dimerizes with an Fc domain comprising the amino acid sequence of SEQ ID NO: 32, 33, 34, 35, 36, or 37, such as shown in Table 6. In some embodiments, the dimers form tetramers. Methods of producing and using the GDF15 molecules disclosed herein are also provided.

DETAILED DESCRIPTION

Figure 1:
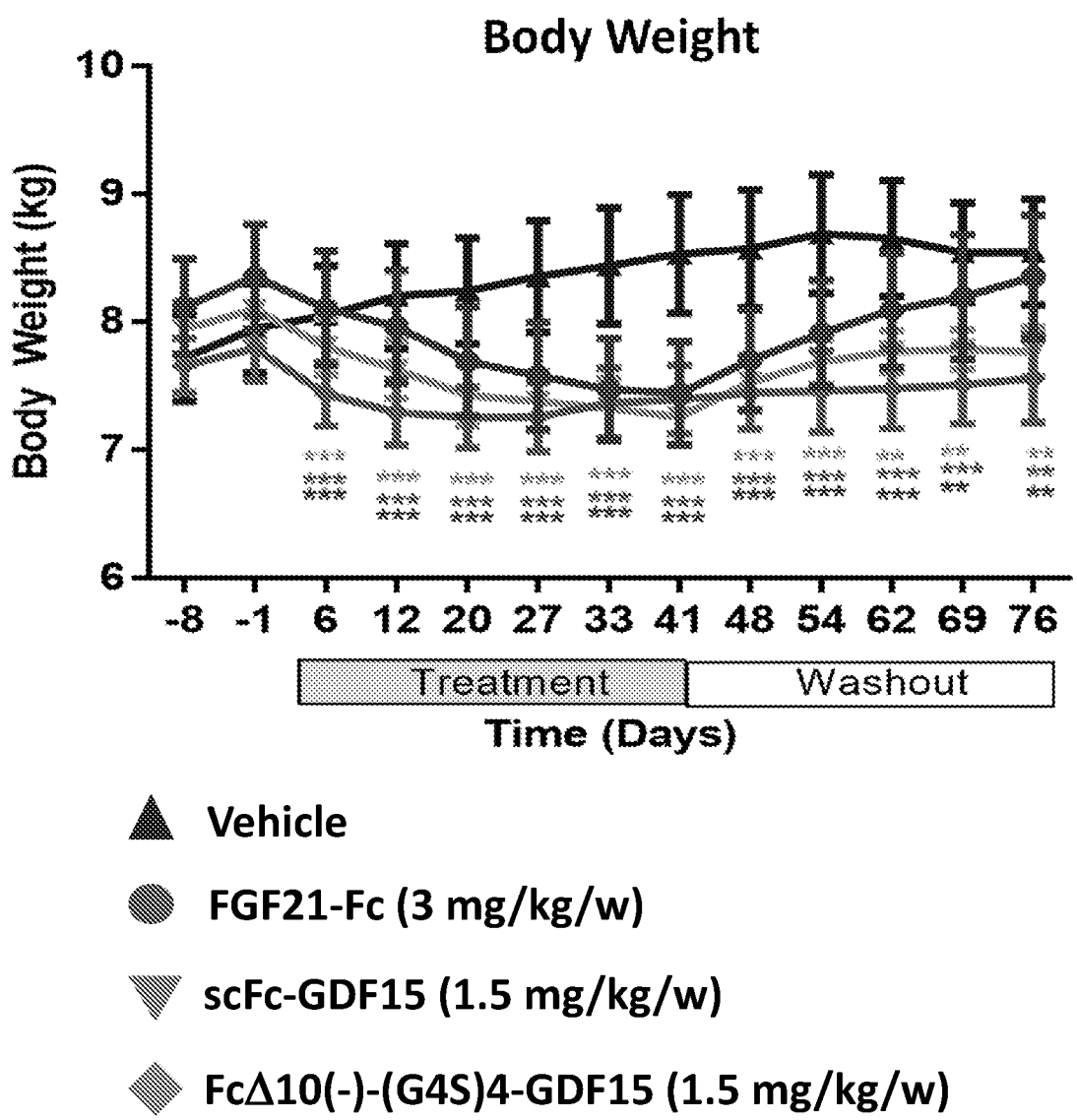
FIG. 1 is a graph showing the effect on the body weight of cynomologus monkeys dosed with vehicle, 3 mg/kg of the positive control FGF21-Fc, 1.5 mg/kg of scFc-GDF15, or 1.5 mg/kg of the dimer FcΔ10(-)-(G4S)4-GDF15:FcΔ10(+, K) weekly for six weeks, followed by a five-week washout.

Provided herein are GDF15 molecules, methods of making the molecules and methods of using the molecules. In some embodiments, the GDF15 molecule is a GDF15-Fc fusion protein. The fusion protein can comprise a GDF15 region joined to an Fc region. In some embodiments, the GDF15 region is joined to the Fc via a linker.

In some embodiments, the GDF15 region comprises wild type GDF15. Both the human and murine GDF15 have a signal peptide and prodomain. The nucleotide sequence for full-length human GDF15 is:

```
                                        (SEQ ID NO: 1)
atgcccgggc aagaactcag gacggtgaat ggctctcaga tgctcctggt gttgctggtg ctctcgtggc tgccgcatgg gggcgccctg tctctggccg aggcgagccg cgcaagtttc ccgggaccct cagagttgca ctccgaagac tccagattcc gagagttgcg gaaacgctac gaggacctgc taaccaggct gcgggccaac cagagctggg aagattcgaa caccgacctc gtcccggccc ctgcagtccg gatactcacg ccagaagtgc ggctgggatc cggcggccac ctgcacctgc gtatctctcg ggccgccctt cccgagggc tccccgaggc ctcccgcctt caccgggctc tgttccggct gtcccgacgc gcgtcaaggt cgtgggacgt gacacgaccg ctgcggcgtc agctcagcct
```

```
tgcaagaccc caggcgcccg cgctgcacct gcgactgtcg ccgccgccgt cgcagtcgga ccaactgctg gcagaatctt cgtccgcacg gccccagctg gagttgcact tgcggccgca agccgccagg gggcgccgca gagcgcgtgc gcgcaacggg gaccactgtc cgctcgggcc cgggcgttgc tgccgtctgc acacggtccg cgcgtcgctg gaagacctgg gctgggccga ttgggtgctg tcgccacggg aggtgcaagt gaccatgtgc atcggcgcgt gcccgagcca gttccgggcg gcaaacatgc acgcgcagat caagacgagc ctgcaccgcc tgaagcccga cacggtgcca gcgccctgct gcgtgcccgc cagctacaat cccatggtgc tcattcaaaa gaccgacacc ggggtgtcgc tccagaccta tgatgacttg ttagccaaag actgccactg catatga
```

The amino acid sequence for full-length human GDF15 (308 amino acids) is:

```
                                        (SEQ ID NO: 2)
MPGQELRTVNGSQMLLVLLVLSWLPHGGALSLA

EASRASFPGPSELHSEDSRFRELRKRYEDLLTR

LRANQSWEDSNTDLVPAPAVRILTPEVRLGSGG

HLHLRISRAALPEGLPEASRLHRALFRLSPTAS

RSWDVTRPLRRQLSLARPQAPALHLRLSPPPSQ

SDQLLAESSSARPQLELHLRPQAARGRRRARAR

NGDHCPLGPGRCCRLHTVRASLEDLGWADWVLS

PREVQVTMCIGACPSQFRAANMHAQIKTSLHRL

KPDTVPAPCCVPASYNPMVLIQKTDTGVSLQTY

DDLLAKDCHCI
```

The nucleotide sequence for human GDF15 without its signal sequence is:

```
                                        (SEQ ID NO: 3)
ctgtctctgg ccgaggcgag ccgcgcaagt ttcccgggac cctcagagtt gcactccgaa gactccagat tccgagagtt gcggaaacgc tacgaggacc tgctaaccag gctgcgggcc aaccagagct gggaagattc gaacaccgac ctcgtcccgg cccctgcagt ccggatactc acgccagaag tgcggctggg
```

```
atccggcggc cacctgcacc tgcgtatctc tcgggccgcc cttccgagg ggctccccga ggcctcccgc cttcaccggg ctctgttccg gctgtcccg acggcgtcaa ggtcgtggga cgtgacacga ccgctgcggc gtcagctcag ccttgcaaga ccccaggcgc ccgcgctgca cctgcgactg tcgccgccgc cgtcgcagtc ggaccaactg ctggcagaat cttcgtccgc acggcccag ctggagttgc acttgcggcc gcaagccgcc aggggcgcc gcagagcgcg tgcgcgcaac ggggaccact gtccgctcgg gcccgggcgt tgctgccgtc tgcacacggt ccgcgcgtcg ctggaagacc tgggctgggc cgattgggtg ctgtcgccac gggaggtgca agtgaccatg tgcatcggcg cgtgcccgag ccagttccgg gcggcaaaca tgcacgcgca gatcaagacg agcctgcacc gcctgaagcc cgacacggtg ccagcgccct gctgcgtgcc cgccagctac aatcccatgg tgctcattca aaagaccgac accgggtgt cgctccagac ctatgatgac ttgttagcca aagactgcca ctgcatatga
```

The amino acid sequence for human GDF15 without its 29 amino acid signal sequence (279 amino acids) is:

(SEQ ID NO: 4)
LSLAEASRASFPGPSELHSEDSRFRELRKRYEDLL
TRLRANQSWEDSNTDLVPAPAVRILTPEVRLGSGG
HLHLRISRAALPEGLPEASRLHRALFRLSPTASRS
WDVTRPLRRQLSLARPQAPALHLRLSPPPSQSDQL
LAESSSARPQLELHLRPQAARGRRRARARNGDHCP
LGPGRCCRLHTVRASLEDLGWADWVLSPREVQVTM
CIGACPSQFRAANMHAQIKTSLHRLKPDTVPAPCC
VPASYNPMVLIQKTDTGVSLQTYDDLLAKDCHCI

The nucleotide sequence for human GDF15 without its signal peptide or prodomain is:

```
                                      (SEQ ID NO: 5)
gcgcgcaacg gggaccactg tccgctcggg cccgg
gcgttgctgc cgtctgcaca cggtccgcgc gtcgc
tggaagacct gggctgggcc gattgggtgc tgtcg
ccacggaggt gcaagtgacc atgtgcatcg gcgc
gtgcccgagc cagttccggg cggcaaacat gcacg
```

```
cgcagatcaag acgagcctgc accgcctgaag ccc
gacacggtgc cagcgccctg ctgcgtgccc gcag
ctacaatccc atggtgctca ttcaaaagac cgaca
ccgggtgtc gctccagacc tatgatgact tgtta
gccaaagact gccactgcat atga
```

The amino acid sequence for human GDF15 without its signal peptide or pro-domain (the active domain of GDF15 of 112 amino acids) is:

(SEQ ID NO: 6)
ARNGDHCPLGPGRCCRLHTVRASLEDLGWADWVLS
PREVQVTMCIGACPSQFRAANMHAQIKTSLHRLKP
DTVPAPCCVPASYNPMVLIQKTDTGVSLQTYDDLL
AKDCHCI

The nucleotide sequence for full-length murine GDF15 is:

```
                                      (SEQ ID NO: 7)
atggccccgc ccgcgctcca ggcccagcct ccaggcggct ctcaactgag gttcctgctg ttcctgctgc tgttgctgct gctgctgtca tggccatcgc aggggacgc cctggcaatg cctgaacagc gaccctccgg ccctgagtcc caactcaacg ccgacgagct acggggtcgc ttccaggacc tgctgagccg gctgcatgcc aaccagagcc gagaggactc gaactcagaa ccaagtcctg acccagctgt ccggatactc agtccagagg tgagattggg gtcccacggc cagctgctac tccgcgtcaa ccgggcgtcg ctgagtcagg gtctccccga agcctaccgc gtgcaccgag cgctgctcct gctgacgccg acggcccgcc cctgggacat cactaggccc ctgaagcgtg cgctcagcct ccggggaccc cgtgctcccg cattacgcct gcgcctgacg ccgcctccgg acctggctat gctgccctct ggcggcacgc agctggaact gcgcttacgg gtagccgccg gcaggggcg ccgaagcgcg catgcgcacc caagagactc gtgcccactg ggtccggggc gctgctgtca cttggagact gtgcaggcaa ctcttgaaga cttgggctgg agcgactggg tgctgtcccc gcgccagctg cagctgagca tgtgcgtggg cgagtgtccc cacctgtatc gctccgcgaa cacgcatgcg
```

-continued
```
cagatcaaag cacgcctgca tggcctgcag cctgacaagg tgcctgcccc gtgctgtgtc ccctccagct acacccggt ggttcttatg cacaggacag acagtggtgt gtcactgcag acttatgatg acctggtggc ccggggctgc cactgcgctt ga
```

The amino acid sequence for full-length murine GDF15 (303 amino acids) is:

```
                                         (SEQ ID NO: 8)
MAPPALQAQPPGGSQLRFLLFLLLLLLLSWPSQG

DALAMPEQRPSGPESQLNADELRGRFQDLLSRLHA

NQSREDSNSEPSPDPAVRILSPEVRLGSHGQLLLR

VNRASLSQGLPEAYRVHRALLLLTPTARPWDITRP

LKRALSLRGPRAPALRLRLTPPPDLAMLPSGGTQL

ELRLRVAAGRGRRSAHAHPRDSCPLGPGRCCHLET

VQATLEDLGWSDWVLSPRQLQLSMCVGECPHLYRS

ANTHAQIKARLHGLQPDKVPAPCCVPSSYTPVVLM

HRTDSGVSLQTYDDLVARGCHCA
```

The nucleotide sequence for murine GDF15 without its signal sequence is:

```
                                         (SEQ ID NO: 9)
tcgcaggggga cgccctggca atgcctgaacagcg accctccggccct gagtcccaact caacgccgacg agctacgggt cgcttccagga cctgctgagccgg ctgcatgccaa ccagagccgagaggactcgaactc agaaccaagt cctgacccagctgtccggatactca gtccagaggt gagattggggtcccacggccagctg ctactccgcgt caaccgggcgtcgctgagtcaggg tctccccgaagcctaccgcgtgcaccgagcgctgc tcctgctgacgccgacggcccgcccctgggacatc actaggcccct gaagcgtgcgctcagcctccgggg accccgtgctcccgcattacgcctgcgcctgacgc cgcctccggacctggctatgctgccctctggcggc acgcagctggaactgcgcttacgggtagccgccgg caggggcgccgaagcgcgcatgcgcacccaagag actcgtgcccactgggtccggggcgctgctgtcac ttggagactgt gcaggcaactcttgaagacttggg ctggagcgactgggtgctgtcccgcgccagctgc agctgagcatgtgcgtgggcgagtgtccccacctg tatcgctccgcgaacacgcatgcgcagatcaaagc acgcctgcatggcctgcagcctgacaaggtgcctg
```

-continued
```
ccccgtgctgtgtccccctccagctacacccggtg gttcttatgcacaggacagacagtggtgtgtcact gcagacttatgatgacctggtggcccggggctgcc actgcgcttga
```

The amino acid sequence for murine GDF15 without its 32 amino acid signal sequence (271 amino acids) is:

```
                                        (SEQ ID NO: 10)
SQGDALAMPEQRPSGPESQLNADELRGRFQDLLSR

LHANQSREDSNSEPSPDPAVRILSPEVRLGSHGQ

LLLRVNRASLSQGLPEAYRVHRALLLLTPTARPWD

ITRPLKRALSLRGPRAPALRLRLTPPPDLAMLPSG

GTQLELRLRVAAGRGRRSAHAHPRDSCPLGPGRCC

HLETVQATLEDLGWSDWVLSPRQLQLSMCVGECPH

LYRSANTHAQIKARLHGLQPDKVPAPCCVPSSYTP

VVLMHRTDSGVSLQTYDDLVARGCHCA
```

The nucleotide sequence for murine GDF15 without its signal sequence or pro-domain is:

```
                                         (SEQ ID NO: 11)
agcgcgcatgcgcacccaagagactcgtgcccact gggtccggggcgctgctgtcacttggagactgtgc aggcaactcttgaagacttgggctggagcgactgg gtgctgtcccgcgccagctgcagctgagcatgtg cgtgggcgagtgtccccacctgtatcgctccgcga acacgcatgcgcagatcaaagcacgcctgcatggc ctgcagcctgacaaggtgcctgccccgtgctgtgt ccccctccagctacacccggtggttcttatgcaca ggacagacagtggtgtgtcactgcagacttatgat gacctggtggcccggggctgccactgcgcttga
```

The amino acid sequence for murine GDF15 without its signal peptide or prodomain (active domain of 115 amino acids) is:

```
                                        (SEQ ID NO: 12)
SAHAHPRDSCPLGPGRCCHLETVQATLEDLGWSDW

VLSPRQLQLSMCVGECPHLYRSANTHAQIKARLHG

LQPDKVPAPCCVPSSYTPVVLMHRTDSGVSLQTYD

DLVARGCHCA
```

In some embodiments, the GDF15 molecule comprises a GDF15 region comprising an active domain of GDF15, e.g., GDF15 without its signal peptide or pro-domain. In some embodiments, the GDF15 region comprises the amino acid sequence of SEQ ID NO: 6 or 12. In some embodiments, the GDF15 region comprises a GDF15 sequence with one or more mutations, such as at least one mutation in the active domain of GDF15. In particular embodiments, the mutation or mutations do not reduce or eliminate the activity of GDF15. In some embodiments, the GDF15 region comprises a mutation in the active domain of human GDF15. In one embodiment, the mutation is a deletion of the first three amino acids of the active domain, such as "GDF15(Δ3)" which is an active domain of human GDF15 in which the first three amino acids removed (i.e., SEQ ID NO: 13).

In some embodiments, the GDF15 region comprises a mutation of the asparagine at position 3 (N3) of the active domain of human GDF15 (SEQ ID NO: 6). An N3 mutation can refer to the mutation of the asparagine residue at position 3 of SEQ ID NO: 6 or the mutation of an asparagine residue corresponding to the asparagine at position 3 of SEQ ID NO: 6 in a GDF15 amino acid sequence. In some embodiments, the asparagine at position 3 is mutated to glutamine (N3Q) or aspartate (N3D). Accordingly, in some embodiments, the GDF15 molecule comprises a GDF15 region of GDF15 (N3Q), which has the amino acid sequence of SEQ ID NO: 14. In other embodiments, the GDF15 molecule comprises a GDF15 region of GDF15(N3D), which has the amino acid sequence of SEQ ID NO: 15. In some embodiments, the GDF15 region comprises a mutation of the aspartate at position 5 (D5) of the active domain of human GDF15 (SEQ ID NO: 6). A D5 mutation can refer to the mutation of the aspartate residue at position 5 of SEQ ID NO: 6 or the mutation of an aspartate residue corresponding to the aspartate at position 5 of SEQ ID NO: 6 in a GDF15 amino acid sequence. In one embodiment, the aspartate at position 5 is mutated to glutamate (D5E). Accordingly, in some embodiments, the GDF15 molecule comprises a GDF15 region of GDF15(D5E), which has the amino acid sequence of SEQ ID NO: 16.

In yet other embodiments, the GDF15 region comprises a combination of mutations, such as a combination of Δ3 and D5 mutations, e.g., GDF15(Δ3/D5E) (SEQ ID NO: 17) or a combination of N3 and D5 mutations, e.g., GDF15(N3D/D5E) or GDF15(N3Q/D5E). In, the GDF15 region comprises the amino acid sequence of SEQ ID NO: 18.

Table 1 provides examples of GDF15 regions that can be used in the GDF15 molecules.

TABLE 1

| SEQ ID NO: | Designation | Sequence |
|---|---|---|
| 6 | GDF15 | ARNGDHCPLGPGRCCRLHTVRASLEDLGWADWVLS PREVQVTMCIGACPSQFRAANMHAQIKTSLHRLKPD TVPAPCCVPASYNPMVLIQKTDTGVSLQTYDDLLAK DCHCI |
| 13 | GDF15(Δ3) | GDHCPLGPGRCCRLHTVRASLEDLGWADWVLSPRE VQVTMCIGACPSQFRAANMHAQIKTSLHRLKPDTVP APCCVPASYNPMVLIQKTDTGVSLQTYDDLLAKDC HCI<br>First third amino acids at N-terminus of GDF15 sequence (SEQ ID NO: 6) is deleted in this GDF15 region. |
| 14 | GDF15(N3Q) | ARQGDHCPLGPGRCCRLHTVRASLEDLGWADWVLS PREVQVTMCIGACPSQFRAANMHAQIKTSLHRLKPD TVPAPCCVPASYNPMVLIQKTDTGVSLQTYDDLLAK DCHCI<br>Underlined and bolded residue is N3Q mutation. |
| 15 | GDF15(N3D) | ARDGDHCPLGPGRCCRLHTVRASLEDLGWADWVLS PREVQVTMCIGACPSQFRAANMHAQIKTSLHRLKPD TVPAPCCVPASYNPMVLIQKTDTGVSLQTYDDLLAK DCHCI<br>Underlined and bolded residue is N3D mutation. |
| 16 | GDF15(D5E) | ARNGEHCPLGPGRCCRLHTVRASLEDLGWADWVLS PREVQVTMCIGACPSQFRAANMHAQIKTSLHRLKPD TVPAPCCVPASYNPMVLIQKTDTGVSLQTYDDLLAK DCHCI<br>Underlined and bolded residue is D5E mutation. |
| 17 | GDF15(Δ3/D5E) | GEHCPLGPGRCCRLHTVRASLEDLGWADWVLSPRE VQVTMCIGACPSQFRAANMHAQIKTSLHRLKPDTVP APCCVPASYNPMVLIQKTDTGVSLQTYDDLLAKDC HCI<br>First third amino acids at N-terminus of GDF15 sequence (SEQ ID NO: 6) is deleted in this GDF15 region; underlined and bolded residue is D5E mutation (position in reference to wild-type GDF15 sequence of SEQ ID NO: 6). |

TABLE 1-continued

GDF15 Regions

| SEQ ID NO: | Designation | Sequence |
|---|---|---|
| 18 | GDF15(N3Q/D5E) | ARQGEHCPLGPGRCCRLHTVRASLEDLGWADWVLS<br>PREVQVTMCIGACPSQFRAANMHAQIKTSLHRLKPD<br>TVPAPCCVPASYNPMVLIQKTDTGVSLQTYDDLLAK<br>DCHCI<br>Underlined and bolded residues are N3Q and D5E mutations. |

In some embodiments, the GDF15 molecule is fused to an Fc directly. In other embodiments, the Fc is fused to the GDF15 molecule via a linker. In some embodiments, the linker comprises a G4S (SEQ ID NO: 19) linker. In other embodiments, the linker comprises a G4Q (SEQ ID NO: 24) linker. In other embodiments, the linker comprises a G4A (SEQ ID NO: 58) linker. The linker can be a (G4S)n or (G4Q)n linker, wherein n is greater than 0. The linker can be a (G4A)n linker, wherein n is greater than 0. In some embodiments, n is 1 or 2. In some embodiments, n is greater than or equal to 2, such as 3, 4, 5, 6, 7, or 8. In some embodiments, the linker comprises the amino acid sequence of SEQ ID NO: 19, 20, 21, 22, 23, 24, 25, or 58 as shown in Table 2.

TABLE 2

Linkers

| SEQ ID NO: | Designation | Sequence |
|---|---|---|
| 19 | G4S | GGGGS |
| 20 | (G4S)2 | GGGGSGGGGS |
| 21 | (G4S)4 | GGGGSGGGGSGGGGSGGGGS |
| 22 | (G4S)8 | GGGGSGGGGSGGGGSGGGGS<br>GGGGSGGGGSGGGGSGGGGS |
| 23 | G4 | GGGG |
| 24 | G4Q | GGGGQ |
| 25 | (G4Q)4 | GGGGQGGGGQGGGGQGGGGQ |
| 58 | G4A | GGGGA |

In some embodiments, the GDF15 molecule comprises an Fc region. The Fc region can comprise or be derived from the Fc domain of a heavy chain of an antibody. In some embodiments, the Fc region may comprise an Fc domain with a mutation, such as a charged pair mutation, a mutation in a glycosylation site or the inclusion of an unnatural amino acid. The Fc region can be derived from a human IgG constant domain of IgG1, IgG2, IgG3 or IgG4. In some embodiments, the Fc region comprises the constant domain of an IgA, IgD, IgE, and IgM heavy chain.

In some embodiments, the Fc region comprises an Fc domain with a charged pair mutation. By introducing a mutation resulting in a charged Fc region, the GDF15 molecule can dimerize with a corresponding Fc molecule having the opposite charge. For example, an aspartate-to-lysine mutation (E356K, wherein 356 is the position using EU numbering, and corresponds to the positions as noted in Tables 3-5) and a glutamate-to-lysine mutation (D399K wherein 399 is the position using EU numbering, and corresponds to positions as noted in Tables 3-5) can be introduced into the Fc region that is joined to a GDF15 region, optionally via a linker, resulting in a positively charged Fc region for the GDF15 molecule. Lysine-to-aspartate mutations (K392D, K409D; wherein 392 and 409 are the positions using EU numbering and corresponds to the positions as noted in Tables 3-5) can be introduced into an Fc domain of a separate molecule, resulting in a negatively charged Fc molecule. The aspartate residues in the negatively charged Fc molecule can associate with the lysine residues of the positively charged Fc region of the GDF15 molecule through electrostatic force, facilitating formation of Fc heterodimers between the Fc region of the GDF15 molecule and the Fc molecule, while reducing or preventing formation of Fc homodimers between the Fc regions of the GDF15 molecules or between Fc molecules.

In some embodiments, one or more lysine-to-aspartate mutations (K392D, K409D) are introduced into the Fc region that is joined to a GDF15 region, optionally via a linker and an aspartate-to-lysine mutation (E356K) and a glutamate-to-lysine mutation (D399K) is introduced into the Fc domain of another molecule. The aspartate residues in the Fc region of the GDF15 molecule can associate with the lysine residues of the Fc molecule through electrostatic force, facilitating formation of Fc heterodimers between the Fc region of the GDF15 molecule and the Fc molecule, and reducing or preventing formation of Fc homodimers between the Fc regions of the GDF15 molecules or between Fc molecules.

In some embodiments, the GDF15 molecule comprises an Fc region comprising an Fc domain with a mutated hinge region. In some embodiments, the Fc domain comprises a deletion in the hinge. In some embodiments, ten amino acids from the hinge are deleted, e.g., FcΔ10. In other embodiments, sixteen amino acids from the hinge are deleted, e.g., FcΔ16. In some embodiments, the Fc domain comprises a hinge deletion (e.g., FcΔ10 or FcΔ16) and a charged pair mutation, such that the Fc domain is positively or negatively charged. For example, the Fc domain can comprise a ten-amino acid deletion in the hinge and lysine-to-aspartate mutations (K392D, K409D), such as FcΔ10(−). In another embodiment, the Fc domain can comprise a ten-amino acid deletion in the hinge and an aspartate-to-lysine mutation (E356K) and a glutamate-to-lysine mutation (D399K), such as an FcΔ10(+). In another embodiment, the Fc domain can comprise a sixteen-amino acid deletion in the hinge and lysine-to-aspartate mutations (K392D, K409D), such as FcΔ16(−). In another embodiment, the Fc domain can comprise a sixteen-amino acid deletion in the hinge and an aspartate-to-lysine mutation (E356K) and a glutamate-to-lysine mutation (D399K), such as an FcΔ16(+).

In some embodiments, an Fc molecule comprising a hinge deletion and a charged pair mutation heterodimerizes with such a GDF15 molecule. For example, the Fc molecule can have a hinge deletion and charged pair mutation that complements the hinge deletion and charged pair mutation of the Fc region of a GDF15 molecule. For example, an Fc molecule can comprise an Fc domain with a ten-amino acid deletion in the hinge and lysine-to-aspartate mutations (K392D, K409D), such as FcΔ10(−), which can optionally comprise a C-terminal lysine (e.g., FcΔ10(−, K)). The Fc molecule can heterodimerize with a GDF15 molecule that comprises an FcΔ10(+). In another embodiment, the Fc molecule can comprise a ten-amino acid deletion in the hinge and an aspartate-to-lysine mutation (E356K) and a glutamate-to-lysine mutation (D399K), such as an FcΔ10 (+), which can optionally comprise a C-terminal lysine (e.g., FcΔ10(+, K)). The Fc molecule can heterodimerize with a GDF15 molecule that comprises an FcΔ10(−). In another embodiment, the Fc molecule can comprise a sixteen-amino acid deletion in the hinge and lysine-to-aspartate mutations (K392D, K409D), such as FcΔ16(−), which can optionally comprise a C-terminal lysine (e.g., FcΔ16(−, K)). The Fc molecule which can heterodimerize with a GDF15 molecule that comprises an FcΔ16(+). In another embodiment, the Fc molecule can comprise a sixteen-amino acid deletion in the hinge and an aspartate-to-lysine mutation (E356K) and a glutamate-to-lysine mutation (D399K), such as an FcΔ16 (+), which can optionally comprise a C-terminal lysine (e.g., FcΔ16(−, K)). The Fc molecule can heterodimerize with a GDF15 molecule that comprises an FcΔ16(−).

In some embodiments, the Fc region or Fc molecule comprises an Fc domain with an L234A and/or L235A mutation, wherein 234 and 235 are the positions using EU numbering and corresponds to the positions as noted in Tables 3-5. The Fc domain can comprise an L234A mutation, an L235A mutation, a charged pair mutation, a hinge deletion, or any combination thereof. In some embodiments, the Fc domain comprises both an L234A mutation and an L235A mutation. In some embodiments, the Fc domain comprises a hinge deletion, an L234A mutation, an L235A mutation, and a charged pair mutation, such as FcΔ10(+, L234A/L235A), FcΔ10(−, L234A/L235A), FcΔ16(+, L234A/L235A), or FcΔ16(−, L234A/L235A). In some embodiments, the Fc domain comprises an optional C-terminal lysine, e.g., FcΔ10(+,K,L234A/L235A), FcΔ10(−,K, L234A/L235A), FcΔ16(+,K,L234A/L235A), or FcΔ16(−,K, L234A/L235A).

In some embodiments, the Fc region or Fc molecule comprises an Fc domain with a "cysteine clamp." A cysteine clamp mutation involves the introduction of a cysteine into the Fc domain at a specific location through mutation so that when incubated with another Fc domain that also has a cysteine introduced at a specific location through mutation, a disulfide bond (cysteine clamp) may be formed between the two Fc domains (e.g., between an FcΔ16 (+) domain having a "cysteine clamp" mutation and an FcΔ16(−) domain having a "cysteine clamp" mutation). The cysteine can be introduced into the CH3 domain of an Fc domain. In some embodiments, an Fc domain may contain one or more such cysteine clamp mutations. In one embodiment, a cysteine clamp is provided by introducing a serine to cysteine mutation (S354C, wherein 354 is the position using EU numbering, and corresponds to the position as noted in Tables 3-5) into a first Fc domain and a tyrosine to cysteine mutation (Y349C, wherein 349 is the position using EU numbering, and corresponds to the position as noted in Tables 3-5) into a second Fc domain. In one embodiment, a GDF15 molecule comprises an Fc region comprising an Fc domain with a cysteine clamp, a negatively charged pair mutation and a sixteen-amino acid hinge deletion (e.g., GDF15-FcΔ16(−,CC)), and an Fc molecule comprising an Fc domain comprising a cysteine clamp, a positively charged pair mutation and a sixteen-amino acid hinge deletion, and an optional C-terminal lysine (e.g., FcΔ16(+,K, CC)). The cysteine clamp may augment the heterodimerization of the GDF-Fc molecule with the Fc molecule.

Examples of Fc regions that can be used in a GDF15 molecule are shown in Table 3.

TABLE 3

Fc Regions

| SEQ ID NO: | Designation | Sequence |
|---|---|---|
| 26 | FcΔ10(−) | APELLGGPSVFLFPPKPKDTLMISRTPEVTCVVV DVSHEDPEVKFNWYVDGVEVHNAKTKPREEQ YNSTYRVVSVLTVLHQDWLNGKEYKCKVSNK ALPAPIEKTISKAKGQPREPQVYTLPPSREEMTK NQVSLTCLVKGFYPSDIAVEWESNGQPENNYDT TPPVLDSDGSFFLYSDLTVDKSRWQQGNVFSCS VMHEALHNHYTQKSLSLSPG Underlined and bolded residues are K392D and K409D mutations. |
| 27 | FcΔ10(+) | APELLGGPSVFLFPPKPKDTLMISRTPEVTCVVV DVSHEDPEVKFNWYVDGVEVHNAKTKPREEQ YNSTYRVVSVLTVLHQDWLNGKEYKCKVSNK ALPAPIEKTISKAKGQPREPQVYTLPPSRKEMTK NQVSLTCLVKGFYPSDIAVEWESNGQPENNYKT TPPVLKSDGSFFLYSKLTVDKSRWQQGNVFSCS VMHEALHNHYTQKSLSLSPG Underlined and bolded residues are E356K and D399K mutations. |

TABLE 3-continued

Fc Regions

| SEQ ID NO: | Designation | Sequence |
|---|---|---|
| 28 | FcΔ10(-, CC) | APELLGGPSVFLFPPKPKDTLMISRTPEVTCVVV<br>DVSHEDPEVKFNWYVDGVEVHNAKTKPREEQ<br>YNSTYRVVSVLTVLHQDWLNGKEYKCKVSNK<br>ALPAPIEKTISKAKGQPREPQVCTLPPSREEMTK<br>NQVSLTCLVKGFYPSDIAVEWE*S*NGQPENNYDT<br>TPPVLDSDGSFFLYSDLTVDKSRWQQGNVFSCS<br>VMHEALHNHYTQKSLSLSPG<br>Underlined and italicized residue is Y349C mutation;<br>underlined and bolded residues are K392D and<br>K409D mutations. |
| 29 | FcΔ16(-, CC) | GPSVFLFPPKPKDTLMISRTPEVTCVVVDVSHED<br>PEVKFNWYVDGVEVHNAKTKPREEQYNSTYRV<br>VSVLTVLHQDWLNGKEYKCKVSNKALPAPIEK<br>TISKAKGQPREPQVCTLPPSREEMTKNQVSLTCL<br>VKGFYPSDIAVEWE*S*NGQPENNYDTTPPVLDSD<br>GSFFLYSDLTVDKSRWQQGNVFSCSVMHEALH<br>NHYTQKSLSLSPG<br>Underlined and italicized residue is Y349C mutation;<br>underlined and bolded residues are K392D and<br>K409D mutations. |
| 30 | FcΔ16(-) | GPSVFLFPPKPKDTLMISRTPEVTCVVVDVSHED<br>PEVKFNWYVDGVEVHNAKTKPREEQYNSTYRV<br>VSVLTVLHQDWLNGKEYKCKVSNKALPAPIEK<br>TISKAKGQPREPQVYTLPPSREEMTKNQVSLTCL<br>VKGFYPSDIAVEWESNGQPENNYDTTPPVLDSD<br>GSFFLYSDLTVDKSRWQQGNVFSCSVMHEALH<br>NHYTQKSLSLSPG<br>Underlined and bolded residues are K392D and<br>K409D mutations. |
| 31 | FcΔ10(-, L234A/L235A) | APE*A*AGGPSVFLFPPKPKDTLMISRTPEVTCVVV<br>DVS*H*EDPEVKFNWYVDGVEVHNAKTKPREEQ<br>YNSTYRVVSVLTVLHQDWLNGKEYKCKVSNK<br>ALPAPIEKTISKAKGQPREPQVYTLPPSREEMTK<br>NQVSLTCLVKGFYPSDIAVEWESNGQPENNYDT<br>TPPVLDSDGSFFLYSDLTVDKSRWQQGNVFSCS<br>VMHEALHNHYTQKSLSLSPG<br>Underlined and italicized residues are L234A and<br>L235A mutations; underlined and bolded residues are<br>K392D and K409D mutations. |

Examples of Fc molecules are shown in Table 4, in which the C-terminal lysine is optional.

TABLE 4

Fc Molecules

| SEQ ID NO: | Designation | Sequence |
|---|---|---|
| 32 | FcΔ10(+, K) | APELLGGPSVFLFPPKPKDTLMISRTPEVTCV<br>VVDVSHEDPEVKFNWYVDGVEVHNAKTKP<br>REEQYNSTYRVVSVLTVLHQDWLNGKEYKC<br>KVSNKALPAPIEKTISKAKGQPREPQVYTLPP<br>SRKEMTKNQVSLTCLVKGFYPSDIAVEWESN<br>GQPENNYKTTPPVLKSDGSFFLYSKLTVDKS<br>RWQQGNVFSCSVMHEALHNHYTQKSLSLSP<br>GK<br>Underlined and bolded residues are E356K and<br>D399K mutations. |
| 33 | FcΔ10(-, K) | APELLGGPSVFLFPPKPKDTLMISRTPEVTCV<br>VVDVSHEDPEVKFNWYVDGVEVHNAKTKP<br>REEQYNSTYRVVSVLTVLHQDWLNGKEYKC |

TABLE 4-continued

Fc Molecules

| SEQ ID NO: | Designation | Sequence |
|---|---|---|
| | | KVSNKALPAPIEKTISKAKGQPREPQVYTLPP<br>SREEMTKNQVSLTCLVKGFYPSDIAVEWESN<br>GQPENNYDTTPPVLDSDGSFFLYSDLTVDKS<br>RWQQGNVFSCSVMHEALHNHYTQKSLSLSP<br>GK<br>Underlined and bolded residues are K392D and K409D mutations. |
| 34 | FcΔ10(+, K, CC) | APELLGGPSVFLFPPKPKDTLMISRTPEVTCV<br>VVDVSHEDPEVKFNWYVDGVEVHNAKTKP<br>REEQYNSTYRVVSVLTVLHQDWLNGKEYKC<br>KVSNKALPAPIEKTISKAKGQPREPQVYTLPP<br>CRKEMTKNQVSLTCLVKGFYPSDIAVEWESN<br>GQPENNYKTTPPVLKSDGSFFLYSKLTVDKS<br>RWQQGNVFSCSVMHEALHNHYTQKSLSLSP<br>GK<br>Underlined and italicized residue is S354C mutation; underlined and bolded residues are E356K and D399K mutations. |
| 35 | FcΔ16(+, K, CC) | GPSVFLFPPKPKDTLMISRTPEVTCVVVDVSH<br>EDPEVKFNWYVDGVEVHNAKTKPREEQYNS<br>TYRVVSVLTVLHQDWLNGKEYKCKVSNKAL<br>PAPIEKTISKAKGQPREPQVYTLPPCRKEMTK<br>NQVSLTCLVKGFYPSDIAVEWESNGQPENNY<br>KTTPPVLKSDGSFFLYSKLTVDKSRWQQGNV<br>FSCSVMHEALHNHYTQKSLSLSPGK<br>Underlined and italicized residue is S354C mutation; underlined and bolded residues are E356K and D399K mutations. |
| 36 | FcΔ16(+, K) | GPSVFLFPPKPKDTLMISRTPEVTCVVVDVSH<br>EDPEVKFNWYVDGVEVHNAKTKPREEQYNS<br>TYRVVSVLTVLHQDWLNGKEYKCKVSNKAL<br>PAPIEKTISKAKGQPREPQVYTLPPSRKEMTK<br>NQVSLTCLVKGFYPSDIAVEWESNGQPENNY<br>KTTPPVLKSDGSFFLYSKLTVDKSRWQQGNV<br>FSCSVMHEALHNHYTQKSLSLSPGK<br>Underlined and bolded residues are E356K and D399K mutations. |
| 37 | FcΔ10(+, K, L234A/L235A) | APEAAGGPSVFLFPPKPKDTLMISRTPEVTCV<br>VVDVSHEDPEVKFNWYVDGVEVHNAKTKP<br>REEQYNSTYRVVSVLTVLHQDWLNGKEYKC<br>KVSNKALPAPIEKTISKAKGQPREPQVYTLPP<br>SRKEMTKNQVSLTCLVKGFYPSDIAVEWESN<br>GQPENNYKTTPPVLKSDGSFFLYSKLTVDKS<br>RWQQGNVFSCSVMHEALHNHYTQKSLSLSP<br>GK<br>Underlined and italicized residues are L234A and L235A mutations; underlined and bolded residues are E356K and D399K mutations. |

The Fc molecules can be used to dimerize with a molecule comprising a complementary Fc domain. For example, an Fc molecule of FcΔ10(+,K) can dimerize with a molecule comprising an Fc region comprising a ten-amino acid hinge deletion and a negatively charged pair mutation such as FcΔ10(−) (e.g., a GDF15 molecule comprising an Fc region of FcΔ10(−)). An Fc molecule of FcΔ10(−,K) can dimerize with a molecule comprising an Fc region comprising a ten-amino acid hinge deletion and a negatively charged pair mutation such as FcΔ10(+) (e.g., a GDF15 molecule comprising an Fc region of FcΔ10(+)).

An Fc molecule of FcΔ10(+,K,CC) can dimerize with a molecule comprising an Fc region comprising a ten-amino acid hinge deletion and a negatively charged pair mutation such as FcΔ10(−,CC) (e.g., a GDF15 molecule comprising an Fc region of FcΔ10(−, CC)). An Fc molecule of FcΔ16(+,K,CC) can dimerize with a molecule comprising an Fc region comprising a ten-amino acid hinge deletion and a negatively charged pair mutation such as FcΔ16(−, CC) (e.g., a GDF15 molecule comprising an Fc region of FcΔ16(−, CC)). An Fc molecule of FcΔ16(+,K) can dimerize with a molecule comprising an Fc region comprising a ten-amino acid hinge deletion and a negatively charged pair mutation such as FcΔ16(−) (e.g., a GDF15 molecule comprising an Fc region of FcΔ16(+)). An Fc molecule of FcΔ10(+,K,L234A/L235A) can dimerize with a molecule comprising an Fc region comprising a ten-amino acid hinge deletion and a negatively charged pair mutation such as FcΔ10(−,L234A/L235A) (e.g., a GDF15 molecule comprising an Fc region of FcΔ10(−, L234A/L235A)).

Examples of GDF15 molecules that are GDF15-Fc fusion proteins are shown in Table 5.

TABLE 5

GDF15 Molecules

| | GDF15-Fc Fusion Protein | | GDF15-Fc Fusion Protein Components SEQ ID NOs | | |
|---|---|---|---|---|---|
| SEQ ID NO. | Designation | Sequence | Fc Region | Linker | GDF15 Region |
| 38 | ScFc7-GDF15 | GGGERKSSVECPPCPAPP VAGPSVFLFPPKPKDTLMI SRTPEVTCVVVDVSHEDP EVQFNWYVDGVEVHNA KTKPREEQFNSTFRVVSV LTVVHQDWLNGKEYKCK VSNKGLPAPIEKTISKTKG QPREPQVYTLPPSREEMT KNQVSLTCLVKGFYPSDI AVEWESNGQPENNYKTT PPMLDSDGSFFLYSKLTV DKSRWQQGNVFSCSVMH EALHNHYTQKSLSLSPGG GGGSGGGGSGGGGSGGG GSGGGGSGGGGSGGGGS GGGGSERKSSVECPPCPA PPVAGPSVFLFPPKPKDTL MISRTPEVTCVVVDVSHE DPEVQFNWYVDGVEVHN AKTKPREEQFNSTFRVVS VLTVVHQDWLNGKEYKC KVSNKGLPAPIEKTISKTK GQPREPQVYTLPPSREEM TKNQVSLTCLVKGFYPSD IAVEWESNGQPENNYKTT PPMLDSDGSFFLYSKLTV DKSRWQQGNVFSCSVMH EALHNHYTQKSLSLSPGS GGGGSGGGGSGGGGSGG GGSARNGDHCPLGPGRC CRLHTVRASLEDLGWAD WVLSPREVQVTMCIGACP SQFRAANMHAQIKTSLHR LKPDTVPAPCCVPASYNP MVLIQKTDTGVSLQTYDD LLAKDCHCI | — | — | — |
| 39 | FcΔ10(−)-(G4S)4-GDF15 | APELLGGPSVFLFPPKPKD TLMISRTPEVTCVVVDVS HEDPEVKFNWYVDGVEV HNAKTKPREEQYNSTYR VVSVLTVLHQDWLNGKE YKCKVSNKALPAPIEKTIS KAKGQPREPQVYTLPPSR EEMTKNQVSLTCLVKGF YPSDIAVEWESNGQPENN YDTTPPVLDSDGSFFLYS DLTVDKSRWQQGNVFSC SVMHEALHNHYTQKSLS LSPGGGGGSGGGGSGGG GSGGGGSARNGDHCPLG PGRCCRLHTVRASLEDLG WADWVLSPREVQVTMCI GACPSQFRAANMHAQIKT SLHRLKPDTVPAPCCVPA SYNPMVLIQKTDTGVSLQ TYDDLLAKDCHCI Underlined and bolded residues are K392D and K409D mutations. | 26 | 21 | 6 |
| 40 | FcΔ10(+)-(G4)-GDF15 | APELLGGPSVFLFPPKPKD TLMISRTPEVTCVVVDVS HEDPEVKFNWYVDGVEV HNAKTKPREEQYNSTYR VVSVLTVLHQDWLNGKE YKCKVSNKALPAPIEKTIS KAKGQPREPQVYTLPPSR KEMTKNQVSLTCLVKGF YPSDIAVEWESNGQPENN YKTTPPVLKSDGSFFLYS | 27 | 23 | 6 |

TABLE 5-continued

GDF15 Molecules

| SEQ ID NO. | Designation | Sequence | GDF15-Fc Fusion Protein Components SEQ ID NOs |  |  |
|---|---|---|---|---|---|
| | | | Fc Region | Linker | GDF15 Region |
| | | KLTVDKSRWQQGNVFSC SVMHEALHNHYTQKSLS LSPGGGGARNGDHCPL GPGRCCRLHTVRASLEDL GWADWVLSPREVQVTM CIGACPSQFRAANMHAQI KTSLHRLKPDTVPAPCCV PASYNPMVLIQKTDTGVS LQTYDDLLAKDCHCI Underlined and and bolded residues are E356K and D399K mutations. | | | |
| 41 | FcΔ10(-)-GDF15(Δ3) | APELLGGPSVFLFPPKPKD TLMISRTPEVTCVVVDVS HEDPEVKFNWYVDGVEV HNAKTKPREEQYNSTYR VVSVLTVLHQDWLNGKE YKCKVSNKALPAPIEKTIS KAKGQPREPQVYTLPPSR EEMTKNQVSLTCLVKGF YPSDIAVEWESNGQPENN YDTTPPVLDSDGSFFLYS DLTVDKSRWQQGNVFSC SVMHEALHNHYTQKSLS LSPGGDHCPLGPGRCCRL HTVRASLEDLGWADWVL SPREVQVTMCIGACPSQF RAANMHAQIKTSLHRLKP DTVPAPCCVPASYNPMVL IQKTDTGVSLQTYDDLLA KDCHCI Underlined and bolded residues are K392D and K409D mutations. | 26 | | 13 |
| 42 | FcΔ10(-)-GDF15 (N3D) | APELLGGPSVFLFPPKPKD TLMISRTPEVTCVVVDVS HEDPEVKFNWYVDGVEV HNAKTKPREEQYNSTYR VVSVLTVLHQDWLNGKE YKCKVSNKALPAPIEKTIS KAKGQPREPQVYTLPPSR EEMTKNQVSLTCLVKGF YPSDIAVEWESNGQPENN YDTTPPVLDSDGSFFLYS DLTVDKSRWQQGNVFSC SVMHEALHNHYTQKSLS LSPGARDGDHCPLGPGRC CRLHTVRASLEDLGWAD WVLSPREVQVTMCIGACP SQFRAANMHAQIKTSLHR LKPDTVPAPCCVPASYNP MVLIQKTDTGVSLQTYDD LLAKDCHCI Underlined and bolded residues are K392D and K409D mutations. | 26 | | 15 |
| 43 | FcΔ10(-, CC)-GDF15(Δ3) | APELLGGPSVFLFPPKPKD TLMISRTPEVTCVVVDVS HEDPEVKFNWYVDGVEV HNAKTKPREEQYNSTYR VVSVLTVLHQDWLNGKE YKCKVSNKALPAPIEKTIS KAKGQPREPQVCTLPPSR EEMTKNQVSLTCLVKGF YPSDIAVEWESNGQPENN YDTTPPVLDSDGSFFLYS DLTVDKSRWQQGNVFSC SVMHEALHNHYTQKSLS | 28 | | 13 |

TABLE 5-continued

GDF15 Molecules

| SEQ ID NO. | Designation | Sequence | Fc Region | Linker | GDF15 Region |
|---|---|---|---|---|---|
| | | LSPGGDHCPLGPGRCCRL HTVRASLEDLGWADWVL SPREVQVTMCIGACPSQF RAANMHAQIKTSLHRLKP DTVPAPCCVPASYNPMVL IQKTDTGVSLQTYDDLLA KDCHCI Underlined and italicized residue is Y349C mutation; underlined and bolded residues are K392D and K409D mutations. | | | |
| 44 | FcΔ10(-, CC)-GDF15(N3D) | APELLGGPSVFLFPPKPKD TLMISRTPEVTCVVVDVS HEDPEVKFNWYVDGVEV HNAKTKPREEQYNSTYR VVSVLTVLHQDWLNGKE YKCKVSNKALPAPIEKTIS KAKGQPREPQVCTLPPSR EEMTKNQVSLTCLVKGF YPSDIAVEWESNGQPENN YDTTPPVLDSDGSFFLYS DLTVDKSRWQQGNVFSC SVMHEALHNHYTQKSLS LSPGARDGDHCPLGPGRC CRLHTVRASLEDLGWAD WVLSPREVQVTMCIGACP SQFRAANMHAQIKTSLHR LKPDTVPAPCCVPASYNP MVLIQKTDTGVSLQTYDD LLAKDCHCI Underlined and italicized residue is Y349C mutation; underlined and bolded residues are K392D and K409D mutations. | 28 | | 15 |
| 45 | FcΔ16(-, CC)-GDF15(Δ3/D5E) | GPSVFLFPPKPKDTLMISR TPEVTCVVVDVSHEDPEV KFNWYVDGVEVHNAKT KPREEQYNSTYRVVSVLT VLHQDWLNGKEYKCKVS NKALPAPIEKTISKAKGQP REPQVCTLPPSREEMTKN QVSLTCLVKGFYPSDIAV EWESNGQPENNYDTTPPV LDSDGSFFLYSDLTVDKS RWQQGNVFSCSVMHEAL HNHYTQKSLSLSPGGEHC PLGPGRCCRLHTVRASLE DLGWADWVLSPREVQVT MCIGACPSQFRAANMHA QIKTSLHRLKPDTVPAPCC VPASYNPMVLIQKTDTGV SLQTYDDLLAKDCHCI Underlined and italicized residue is Y349C mutation; underlined and bolded residues are K392D and K409D mutations. | 29 | | 17 |
| 46 | FcΔ16(-, CC)-GDF15(N3Q/D5E) | GPSVFLFPPKPKDTLMISR TPEVTCVVVDVSHEDPEV KFNWYVDGVEVHNAKT KPREEQYNSTYRVVSVLT VLHQDWLNGKEYKCKVS NKALPAPIEKTISKAKGQP REPQVCTLPPSREEMTKN QVSLTCLVKGFYPSDIAV EWESNGQPENNYDTTPPV | 29 | | 18 |

TABLE 5-continued

GDF15 Molecules

| SEQ ID NO. | Designation | Sequence | GDF15-Fc Fusion Protein Components SEQ ID NOs | | |
|---|---|---|---|---|---|
| | | | Fc Region | Linker | GDF15 Region |
| | | LDSDGSFFLYS*D*LTVDKS RWQQGNVFSCS*V*MHEAL HNHYTQKSLSLSPGARQG EHCPLGPGRCCRLHTVRA SLEDLGWADWVLSPREV QVTMCIGACPSQFRAAN MHAQIKTSLHRLKPDTVP APCCVPASYNPMVLIQKT DTGVSLQTYDDLLAKDC HCI<br>Underlined and italicized residue is Y349C mutation; underlined and bolded residues are K392D and K409D mutations. | | | |
| 47 | FcΔ16(-)-GDF15(N3Q/D5E) | GPSVFLFPPKPKDTLMISR TPEVTCVVVDVSHEDPEV KFNWYVDGVEVHNAKT KPREEQYNSTYRVVSVLT VLHQDWLNGKEYKCKVS NKALPAPIEKTISKAKGQP REPQVYTLPPSREEMTKN QVSLTCLVKGFYPSDIAV EWESNGQPENNYDTTPPV LDSDGSFFLYSDLTVDKS RWQQGNVFSCSVMHEAL HNHYTQKSLSLSPGARQG EHCPLGPGRCCRLHTVRA SLEDLGWADWVLSPREV QVTMCIGACPSQFRAAN MHAQIKTSLHRLKPDTVP APCCVPASYNPMVLIQKT DTGVSLQTYDDLLAKDC HCI<br>Underlined and bolded residues are K392D and K409D mutations. | 30 | | 18 |
| 48 | FcΔ16(-)-(G4Q)4-GDF15 | GPSVFLFPPKPKDTLMISR TPEVTCVVVDVSHEDPEV KFNWYVDGVEVHNAKT KPREEQYNSTYRVVSVLT VLHQDWLNGKEYKCKVS NKALPAPIEKTISKAKGQP REPQVYTLPPSREEMTKN QVSLTCLVKGFYPSDIAV EWESNGQPENNYDTTPPV LDSDGSFFLYSDLTVDKS RWQQGNVFSCSVMHEAL HNHYTQKSLSLSPGGGGG QGGGGQGGGGQGGGGQ ARNGDHCPLGPGRCCRL HTVRASLEDLGWADWVL SPREVQVTMCIGACPSQF RAANMHAQIKTSLHRLKP DTVPAPCCVPASYNPMVL IQKTDTGVSLQTYDDLLA KDCHCI<br>Underlined and bolded residues are K392D and K409D mutations. | 30 | 25 | 6 |
| 49 | FcΔ16(-)-(G4Q)4-GDF15(N3Q) | GPSVFLFPPKPKDTLMISR TPEVTCVVVDVSHEDPEV KFNWYVDGVEVHNAKT KPREEQYNSTYRVVSVLT VLHQDWLNGKEYKCKVS NKALPAPIEKTISKAKGQP REPQVYTLPPSREEMTKN QVSLTCLVKGFYPSDIAV | 30 | 25 | 14 |

TABLE 5-continued

GDF15 Molecules

| SEQ ID NO. | Designation | GDF15-Fc Fusion Protein Sequence | GDF15-Fc Fusion Protein Components SEQ ID NOs |  |  |
|---|---|---|---|---|---|
| | | | Fc Region | Linker | GDF15 Region |
| | | EWESNGQPENNYDTTPPV LDSDGSFFLYSDLTVDKS RWQQGNVFSCSVMHEAL HNHYTQKSLSLSPGGGGG QGGGGQGGGGQGGGGQ ARQGDHCPLGPGRCCRL HTVRASLEDLGWADWVL SPREVQVTMCIGACPSQF RAANMHAQIKTSLHRLKP DTVPAPCCVPASYNPMVL IQKTDTGVSLQTYDDLLA KDCHCI Underlined and bolded residues are K392D and K409D mutations. | | | |
| 50 | FcΔ16(−)- (G4Q)4- GDF15(N3Q/ D5E) | GPSVFLFPPKPKDTLMISR TPEVTCVVVDVSHEDPEV KFNWYVDGVEVHNAKT KPREEQYNSTYRVVSVLT VLHQDWLNGKEYKCKVS NKALPAPIEKTISKAKGQP REPQVYTLPPSREEMTKN QVSLTCLVKGFYPSDIAV EWESNGQPENNYDTTPPV LDSDGSFFLYSDLTVDKS RWQQGNVFSCSVMHEAL HNHYTQKSLSLSPGGGGG QGGGGQGGGGQGGGGQ ARQGEHCPLGPGRCCRLH TVRASLEDLGWADWVLS PREVQVTMCIGACPSQFR AANMHAQIKTSLHRLKPD TVPAPCCVPASYNPMVLI QKTDTGVSLQTYDDLLA KDCHCI Underlined and bolded residues are K392D and K409D mutations. | 30 | 25 | 18 |
| 51 | FcΔ16(−)- (G4S)2- GDF15 (N3Q) | GPSVFLFPPKPKDTLMISR TPEVTCVVVDVSHEDPEV KFNWYVDGVEVHNAKT KPREEQYNSTYRVVSVLT VLHQDWLNGKEYKCKVS NKALPAPIEKTISKAKGQP REPQVYTLPPSREEMTKN QVSLTCLVKGFYPSDIAV EWESNGQPENNYDTTPPV LDSDGSFFLYSDLTVDKS RWQQGNVFSCSVMHEAL HNHYTQKSLSLSPGGGGG SGGGGSARQGDHCPLGP GRCCRLHTVRASLEDLG WADWVLSPREVQVTMCI GACPSQFRAANMHAQIKT SLHRLKPDTVPAPCCVPA SYNPMVLIQKTDTGVSLQ TYDDLLAKDCHCI Underlined and bolded residues are K392D and K409D mutations. | 30 | 20 | 14 |
| 52 | FcΔ16(−)- (G4S)2- GDF15(N3Q/ D5E) | GPSVFLFPPKPKDTLMISR TPEVTCVVVDVSHEDPEV KFNWYVDGVEVHNAKT KPREEQYNSTYRVVSVLT VLHQDWLNGKEYKCKVS NKALPAPIEKTISKAKGQP REPQVYTLPPSREEMTKN QVSLTCLVKGFYPSDIAV EWESNGQPENNYDTTPPV | 30 | 20 | 18 |

TABLE 5-continued

GDF15 Molecules

| SEQ ID NO. | Designation | GDF15-Fc Fusion Protein Sequence | Fc Region | Linker | GDF15 Region |
|---|---|---|---|---|---|
| | | LDSDGSFFLYSDLTVDKS RWQQGNVFSCSVMHEAL HNHYTQKSLSLSPGGGGG SGGGGSARQGEHCPLGPG RCCRLHTVRASLEDLGW ADWVLSPREVQVTMCIG ACPSQFRAANMHAQIKTS LHRLKPDTVPAPCCVPAS YNPMVLIQKTDTGVSLQT YDDLLAKDCHCI Underlined and bolded residues are K392D and K409D mutations. | | | |
| 53 | FcΔ16(-)- G4S- GDF15(N3Q) | GPSVFLFPPKPKDTLMISR TPEVTCVVVDVSHEDPEV KFNWYVDGVEVHNAKT KPREEQYNSTYRVVSVLT VLHQDWLNGKEYKCKVS NKALPAPIEKTISKAKGQP REPQVYTLPPSREEMTKN QVSLTCLVKGFYPSDIAV EWESNGQPENNYDTTPPV LDSDGSFFLYSDLTVDKS RWQQGNVFSCSVMHEAL HNHYTQKSLSLSPGGGGG SARQGDHCPLGPGRCCRL HTVRASLEDLGWADWVL SPREVQVTMCIGACPSQF RAANMHAQIKTSLHRLKP DTVPAPCCVPASYNPMVL IQKTDTGVSLQTYDDLLA KDCHCI Underlined and bolded residues are K392D and K409D mutations. | 30 | 19 | 14 |
| 54 | FcΔ16(-)- G4S- GDF15(N3Q/ D5E) | GPSVFLFPPKPKDTLMISR TPEVTCVVVDVSHEDPEV KFNWYVDGVEVHNAKT KPREEQYNSTYRVVSVLT VLHQDWLNGKEYKCKVS NKALPAPIEKTISKAKGQP REPQVYTLPPSREEMTKN QVSLTCLVKGFYPSDIAV EWESNGQPENNYDTTPPV LDSDGSFFLYSDLTVDKS RWQQGNVFSCSVMHEAL HNHYTQKSLSLSPGGGGG SARQGEHCPLGPGRCCRL HTVRASLEDLGWADWVL SPREVQVTMCIGACPSQF RAANMHAQIKTSLHRLKP DTVPAPCCVPASYNPMVL IQKTDTGVSLQTYDDLLA KDCHCI Underlined and bolded residues are K392D and K409D mutations. | 30 | 19 | 18 |
| 55 | FcΔ16(-)- GDF15(N3Q) | GPSVFLFPPKPKDTLMISR TPEVTCVVVDVSHEDPEV KFNWYVDGVEVHNAKT KPREEQYNSTYRVVSVLT VLHQDWLNGKEYKCKVS NKALPAPIEKTISKAKGQP REPQVYTLPPSREEMTKN QVSLTCLVKGFYPSDIAV EWESNGQPENNYDTTPPV LDSDGSFFLYSDLTVDKS RWQQGNVFSCSVMHEAL | 30 | | 14 |

TABLE 5-continued

GDF15 Molecules

| | GDF15-Fc Fusion Protein | | GDF15-Fc Fusion Protein Components SEQ ID NOs | | |
|---|---|---|---|---|---|
| SEQ ID NO. | Designation | Sequence | Fc Region | Linker | GDF15 Region |
| | | HNHYTQKSLSLSPGARQG DHCPLGPGRCCRLHTVRA SLEDLGWADWVLSPREV QVTMCIGACPSQFRAAN MHAQIKTSLHRLKPDTVP APCCVPASYNPMVLIQKT DTGVSLQTYDDLLAKDC HCI Underlined and bolded residues are K392D and K409D mutations. | | | |
| 56 | FcΔ10(-, L234A/L235 A)-(G4Q)4-GDF15(N3Q) | APEAAGGPSVFLFPPKPKD TLM*I*SRTPEVTCVVVDVS HEDPEVKFNWYVDGVEV HNAKTKPREEQYNSTYR VVSVLTVLHQDWLNGKE YKCKVSNKALPAPIEKTIS KAKGQPREPQ VYTLPP SR EEMTKNQVSLTCLVKGF YPSDIAVEWESNGQPENN YDTTPPVLDSDGSFFLYS DLTVDKSRWQQGNVFSC SVMHEALHNHYTQKSLS LSPGGGGGQGGGGQGGG GQGGGGQARQGDHCPLG PGRCCRLHTVRASLEDLG WADWVLSPREVQVTMCI GACPSQFRAANMHAQIKT SLHRLKPDTVPAPCCVPA SYNPMVLIQKTDTGVSLQ TYDDLLAKDCHCI Underlined and italicized residues are L234A and L235A mutations; underlined and bolded residues are K392D and K409D mutations. | 31 | 25 | 14 |
| 57 | FcΔ10(-, L234A/L235 A)-(G4Q)4-GDF15(N3Q/ D5E) | APEAAGGPSVFLFPPKPKD TLM*I*SRTPEVTCVVVDVS HEDPEVKFNWYVDGVEV HNAKTKPREEQYNSTYR VVSVLTVLHQDWLNGKE YKCKVSNKALPAPIEKTIS KAKGQPREPQ VYTLPP SR EEMTKNQVSLTCLVKGF YPSDIAVEWESNGQPENN YDTTPPVLDSDGSFFLYS DLTVDKSRWQQGNVFSC SVMHEALHNHYTQKSLS LSPGGGGGQGGGGQGGG GQGGGGQARQGEHCPLG PGRCCRLHTVRASLEDLG WADWVLSPREVQVTMCI GACPSQFRAANMHAQIKT SLHRLKPDTVPAPCCVPA SYNPMVLIQKTDTGVSLQ TYDDLLAKDCHCI Underlined and italicized residues are L234A and L235A mutations; underlined and bolded residues are K392D and K409D mutations. | 31 | 25 | 18 |

In some embodiments, the fusion protein is an scFc-GDF15 in which the GDF15 region is joined to two Fc regions. In some embodiments, the fusion protein comprises an amino acid sequence that has at least 85%, 90%, 95% or 99% sequence identity to SEQ ID NO: 38. In some embodiments, the fusion protein comprises an amino acid sequence of SEQ ID NO: 38. In calculating percent sequence identity, the sequences being compared are aligned in a way that gives the largest match between the sequences. A computer program that can be used to determine percent identity is the GCG program package, which includes GAP (Devereux et al., (1984) Nucl. Acid Res. 12:387; Genetics Computer Group, University of Wisconsin, Madison, Wis.). The computer algorithm GAP can be used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., (1978) Atlas of Protein Sequence and Structure 5:345-352 for the PAM 250 comparison matrix; Henikoff et al., (1992) Proc. Natl. Acad. Sci. U.S.A. 9:10915-10919 for the BLOSUM 62 comparison matrix) is also used by the algorithm. Parameters that can be used for determining percent identity using the GAP program are the following:

Algorithm: Needleman et al., 1970, J. Mol. Biol. 48:443-453;

Comparison matrix: BLOSUM 62 from Henikoff et al., 1992, supra;

Gap Penalty: 12 (but with no penalty for end gaps)

Gap Length Penalty: 4

Threshold of Similarity: 0

Certain alignment schemes for aligning two amino acid sequences can result in matching of only a short region of the two sequences, and this small aligned region can have very high sequence identity even though there is no significant relationship between the two full-length sequences. Accordingly, the selected alignment method (e.g., the GAP program) can be adjusted if so desired to result in an alignment that spans at least 50 contiguous amino acids of the target polypeptide.

In some embodiments, the GDF15 molecule is FcΔ10(−)-(G4S)4-GDF15, FcΔ10(+)-(G4)-GDF15, FcΔ10(−)-GDF15(Δ3), FcΔ10(−)-GDF15(N3D), FcΔ10(−,CC)-GDF15(Δ3), FcΔ10(−,CC)-GDF15(N3D), FcΔ16(−,CC)-GDF15(Δ3/D5E), FcΔ16(−,CC)-GDF15(N3Q/D5E), FcΔ16(−)-GDF15(N3Q/D5E), FcΔ16(−)-(G4Q)4-GDF15, FcΔ16(−)-(G4Q)4-GDF15(N3Q), FcΔ16(−)-(G4Q)4-GDF15(N3Q/D5E), FcΔ16(−)-(G4S)2-GDF15(N3Q), FcΔ16(−)-(G4S)2-GDF15(N3Q/D5E), FcΔ16(−)-G4S-GDF15(N3Q), FcΔ16(−)-G4S-GDF15(N3Q/D5E), FcΔ16(−)-GDF15(N3Q), FcΔ10(−,L234A/L235A)-(G4Q)4-GDF15(N3Q), or FcΔ10(−,L234A/L235A)-(G4Q)4-GDF15(N3Q/D5E).

In some embodiments, the GDF15 molecule comprises the amino acid sequence of SEQ ID NO: 39, 40, 41, 42, 43, 44, 45, 46, 47, 48, 49, 50, 51, 52, 53, 54, 55, 56, or 57. In some embodiments, the GDF15 molecule comprises an amino acid sequence that has 80-99%, 85%-99%, 90-99%, or 95-99% sequence identity to SEQ ID NO: 39, 40, 41, 42, 43, 44, 45, 46, 47, 48, 49, 50, 51, 52, 53, 54, 55, 56, or 57. In some embodiments, the GDF15 molecule comprises an amino acid sequence that has at least 85% sequence identity to SEQ ID NO: 39, 40, 41, 42, 43, 44, 45, 46, 47, 48, 49, 50, 51, 52, 53, 54, 55, 56, or 57. In some embodiments, the GDF15 molecule comprises an amino acid sequence that has at least 90% sequence identity to SEQ ID NO: 39, 40, 41, 42, 43, 44, 45, 46, 47, 48, 49, 50, 51, 52, 53, 54, 55, 56, or 57. In some embodiments, the GDF15 molecule comprises an amino acid sequence that has at least 95% sequence identity to SEQ ID NO: 39, 40, 41, 42, 43, 44, 45, 46, 47, 48, 49, 50, 51, 52, 53, 54, 55, 56, or 57. In some embodiments, the GDF15 molecule comprises an amino acid sequence that has at least 99% sequence identity to SEQ ID NO: 39, 40, 41, 42, 43, 44, 45, 46, 47, 48, 49, 50, 51, 52, 53, 54, 55, 56, or 57.

In some embodiments, the GDF15 molecule is a FcΔ10(−)-(G4S)4-GDF15, FcΔ10(+)-(G4)-GDF15, FcΔ10(−)-GDF15(Δ3), FcΔ10(−)-GDF15(N3D), FcΔ10(−,CC)-GDF15(Δ3), FcΔ10(−,CC)-GDF15(N3D), FcΔ16(−,CC)-GDF15(Δ3/D5E), FcΔ16(−,CC)-GDF15(N3Q/D5E), FcΔ16(−)-GDF15(N3Q/D5E), FcΔ16(−)-(G4Q)4-GDF15, FcΔ16(−)-(G4Q)4-GDF15(N3Q), FcΔ16(−)-(G4Q)4-GDF15(N3Q/D5E), FcΔ16(−)-(G4S)2-GDF15(N3Q), FcΔ16(−)-(G4S)2-GDF15(N3Q/D5E), FcΔ16(−)-G4S-GDF15(N3Q), FcΔ16(−)-G4S-GDF15(N3Q/D5E), FcΔ16(−)-GDF15(N3Q), FcΔ10(−,L234A/L235A)-(G4Q)4-GDF15(N3Q), or FcΔ10(−,L234A/L235A)-(G4Q)4-GDF15(N3Q/D5E) molecule. In some embodiments, the GDF15 molecule is a FcΔ10(−)-(G4S)4-GDF15, FcΔ10(+)-(G4)-GDF15, FcΔ10(−)-GDF15(Δ3), FcΔ10(−)-GDF15(N3D), FcΔ10(−,CC)-GDF15(Δ3), FcΔ10(−,CC)-GDF15(N3D), FcΔ16(−,CC)-GDF15(Δ3/D5E), FcΔ16(−,CC)-GDF15(N3Q/D5E), FcΔ16(−)-GDF15(N3Q/D5E), FcΔ16(−)-(G4Q)4-GDF15, FcΔ16(−)-(G4Q)4-GDF15(N3Q), FcΔ16(−)-(G4Q)4-GDF15(N3Q/D5E), FcΔ16(−)-(G4S)2-GDF15(N3Q), FcΔ16(−)-(G4S)2-GDF15(N3Q/D5E), FcΔ16(−)-G4S-GDF15(N3Q), FcΔ16(−)-G4S-GDF15(N3Q/D5E), FcΔ16(−)-GDF15(N3Q), FcΔ10(−,L234A/L235A)-(G4Q)4-GDF15(N3Q), or FcΔ10(−,L234A/L235A)-(G4Q)4-GDF15(N3Q/D5E) molecule that has 80-99%, 85%-99%, 90-99%, or 95-99% sequence identity to its Fc region and/or GDF15 region.

In some embodiments, the GDF15 molecule is a FcΔ10(−)-(G4S)4-GDF15, FcΔ10(+)-(G4)-GDF15, FcΔ10(−)-GDF15(Δ3), FcΔ10(−)-GDF15(N3D), FcΔ10(−,CC)-GDF15(Δ3), FcΔ10(−,CC)-GDF15(N3D), FcΔ16(−,CC)-GDF15(Δ3/D5E), FcΔ16(−,CC)-GDF15(N3Q/D5E), FcΔ16(−)-GDF15(N3Q/D5E), FcΔ16(−)-(G4Q)4-GDF15, FcΔ16(−)-(G4Q)4-GDF15(N3Q), FcΔ16(−)-(G4Q)4-GDF15(N3Q/D5E), FcΔ16(−)-(G4S)2-GDF15(N3Q), FcΔ16(−)-(G4S)2-GDF15(N3Q/D5E), FcΔ16(−)-G4S-GDF15(N3Q), FcΔ16(−)-G4S-GDF15(N3Q/D5E), FcΔ16(−)-GDF15(N3Q), FcΔ10(−,L234A/L235A)-(G4Q)4-GDF15(N3Q), or FcΔ10(−,L234A/L235A)-(G4Q)4-GDF15(N3Q/D5E) molecule that has at least 85%, 90%, 95% or 99% sequence identity to its Fc region and/or GDF15 region. For example, a FcΔ10(−)-(G4S)4-GDF15 molecule with 80-99%, 85%-99%, 90-99%, or 95-99% sequence identity to its Fc region and/or GDF15 region, includes a GDF15 molecule with an Fc region that has a ten-amino acid deletion of the hinge region and a negatively charged pair mutation, and has 80-99%, 85%-99%, 90-99%, or 95-99% sequence identity to SEQ ID NO: 26 and/or a GDF15 region that has 80-99%, 85%-99%, 90-99%, or 95-99% sequence identity to SEQ ID NO: 6. For example, a FcΔ10(−)-(G4S)4-GDF15 molecule with at least 85%, 90%, 95% or 99% sequence identity to its Fc region and/or GDF15 region, includes a GDF15 molecule with an Fc region that has a ten-amino acid deletion of the hinge region and a negatively charged pair mutation, and has at least 85%, 90%, 95% or 99% sequence identity to SEQ ID NO: 26 and/or a GDF15 region that has at least 85%, 90%, 95% or 99% sequence identity to SEQ ID NO: 6.

In another example, a FcΔ16(−)-(G4Q)4-GDF15(N3Q/D5E) molecule with 80-99%, 85%-99%, 90-99%, or 95-99% sequence identity to its Fc region and/or a GDF15 region, includes a GDF15 molecule with an Fc region that has a sixteen-amino acid deletion of the hinge region and a negatively charged pair mutation that has 80-99%, 85%-99%, 90-99%, or 95-99% sequence identity to SEQ ID NO: 30 and/or a GDF15 region that has 80-99%, 85%-99%, 90-99%, or 95-99% sequence identity to SEQ ID NO: 18. In another example, a FcΔ16(−)-(G4Q)4-GDF15(N3Q/D5E) molecule with at least 85%, 90%, 95% or 99% identity to its Fc region and/or a GDF15 region, includes a GDF15 molecule with an Fc region that has a sixteen-amino acid deletion of the hinge region and a negatively charged pair mutation that has at least 85%, 90%, 95% or 99% sequence identity to SEQ ID NO: 30 and/or a GDF15 region that has at least 85%, 90%, 95% or 99% sequence identity to SEQ ID NO: 18.

In yet another example, a FcΔ10(−,L234A/L235A)-(G4Q)4-GDF15(N3Q/D5E) molecule with 80-99%, 85%-99%, 90-99%, or 95-99% sequence identity to its Fc region and/or a GDF15 region, includes a GDF15 molecule with an Fc region that has a ten-amino acid deletion of the hinge region, a negatively charged pair mutation and leucine to alanine mutations at positions 234 and 235 and has 80-99%, 85%-99%, 90-99%, or 95-99% sequence identity to SEQ ID NO: 31 and/or a GDF15 region that has 80-99%, 85%-99%, 90-99%, or 95-99% sequence identity to SEQ ID NO: 18. In yet another example, a FcΔ10(−,L234A/L235A)-(G4Q)4-GDF15(N3Q/D5E) molecule with at least 85%, 90%, 95% or 99% sequence identity to its Fc region and/or a GDF15 region, includes a GDF15 molecule with an Fc region that has a ten-amino acid deletion of the hinge region, a negatively charged pair mutation and leucine to alanine mutations at positions 234 and 235 and has at least 85%, 90%, 95% or 99% sequence identity to SEQ ID NO: 31 and/or a GDF15 region that has at least 85%, 90%, 95% or 99% sequence identity to SEQ ID NO: 18.

Also provided herein are dimers and tetramers comprising a GDF15 molecule provided herein. In one embodiment, the dimer comprises a GDF15-Fc fusion comprising the amino acid sequence of any one of SEQ ID NOs: 39-57. In some embodiments, a GDF15-Fc fusion comprising the amino acid sequence of SEQ ID NO: 39, 40, 41, 42, 43, 44, 45, 46, 47, 48, 49, 50, 51, 52, 53, 54, 55, 56 or 57 dimerizes with an Fc molecule comprising the amino acid sequence of SEQ ID NO: 32, 33, 34, 35, 36, or 37 (in which the C-terminal lysine is optional), such as shown in Table 6. For example, in some embodiments, the dimer is FcΔ10(−)-(G4S)4-GDF15: FcΔ10(+,K). In another embodiment, the dimer is FcΔ10(−,L234A/L235A)-(G4Q)4-GDF15(N3Q): FcΔ10(+,K,L234A/L235A). In yet another embodiment, the dimer is FcΔ10(−,L234A/L235A)-(G4Q)4-GDF15(N3Q):FcΔ10(+,K,L234A/L235A).

TABLE 6

Dimers

| GDF15-Fc Fusion SEQ ID NO. | GDF15-Fc Fusion Designation | Corresponding Fc Molecule SEQ ID NO. | Fc Molecule Designation |
|---|---|---|---|
| 39 | FcΔ10(−)-(G4S)4-GDF15 | 32 | FcΔ10(+, K) |
| 40 | FcΔ10(+)-(G4)-GDF15 | 33 | FcΔ10(−, K) |
| 41 | FcΔ10(−)-GDF15(Δ3) | 32 | FcΔ10(+, K) |
| 42 | FcΔ10(−)-GDF15(N3D) | 32 | FcΔ10(+, K) |
| 43 | FcΔ10(−, CC)-GDF15(Δ3) | 34 | FcΔ10(+, K, CC) |
| 44 | FcΔ10(−, CC)-GDF15(N3D) | 34 | FcΔ10(+, K, CC) |
| 45 | FcΔ16(−, CC)-GDF15(Δ3/D5E) | 35 | FcΔ16(+, K, CC) |
| 46 | FcΔ16(−, CC)-GDF15(N3Q/D5E) | 35 | FcΔ16(+, K, CC) |
| 47 | FcΔ16(−)-GDF15(N3Q/D5E) | 36 | FcΔ16(+, K) |
| 48 | FcΔ16(−)-(G4Q)4-GDF15 | 36 | FcΔ16(+, K) |
| 49 | FcΔ16(−)-(G4Q)4-GDF15(N3Q) | 36 | FcΔ16(+, K) |
| 50 | FcΔ16(−)-(G4Q)4-GDF15(N3Q/D5E) | 36 | FcΔ16(+, K) |
| 51 | FcΔ16(−)-(G4S)2-GDF15(N3Q) | 36 | FcΔ16(+, K) |
| 52 | FcΔ16(−)-(G4S)2-GDF15(N3Q/D5E) | 36 | FcΔ16(+, K) |
| 53 | FcΔ16(−)-G4S- GDF15(N3Q) | 36 | FcΔ16(+, K) |
| 54 | FcΔ16(−)-G4S-GDF15(N3Q/D5E) | 36 | FcΔ16(+, K) |
| 55 | FcΔ16(−)-GDF15(N3Q) | 36 | FcΔ16(+, K) |
| 56 | FcΔ10(−, L234A/L235A)-(G4Q)4-GDF15(N3Q) | 37 | FcΔ10(+, K, L234A/L235A) |
| 57 | FcΔ10(−, L234A/L235A)-(G4Q)4-GDF15(N3Q/D5E) | 37 | FcΔ10(+, K, L234A/L235A) |

In one embodiment, a GDF15-Fc fusion comprising the amino acid sequence of SEQ ID NO: 39 dimerizes with an Fc molecule comprising SEQ ID NO: 32 (C-terminal lysine optional). In another embodiment, a GDF15-Fc fusion comprising the amino acid sequence of SEQ ID NO: 40 dimerizes with an Fc molecule comprising SEQ ID NO: 33 (C-terminal lysine optional). In another embodiment, a GDF15-Fc fusion comprising the amino acid sequence of SEQ ID NO: 41 dimerizes with an Fc molecule comprising SEQ ID NO: 32 (C-terminal lysine optional). In another embodiment, a GDF15-Fc fusion comprising the amino acid sequence of SEQ ID NO: 42 dimerizes with an Fc molecule comprising SEQ ID NO: 32 (C-terminal lysine optional). In another embodiment, a GDF15-Fc fusion comprising the amino acid sequence of SEQ ID NO: 43 dimerizes with an Fc molecule comprising SEQ ID NO: 34 (C-terminal lysine optional). In another embodiment, a GDF15-Fc fusion comprising the amino acid sequence of SEQ ID NO: 44 dimerizes with an Fc molecule comprising SEQ ID NO: 34 (C-terminal lysine optional). In another embodiment, a GDF15-Fc fusion comprising the amino acid sequence of SEQ ID NO: 44 dimerizes with an Fc molecule comprising SEQ ID NO: 34 (C-terminal lysine optional). In another embodiment, a GDF15-Fc fusion comprising the amino acid sequence of SEQ ID NO: 45 dimerizes with an Fc molecule comprising SEQ ID NO: 35 (C-terminal lysine optional). In another embodiment, a GDF15-Fc fusion comprising the amino acid sequence of SEQ ID NO: 46 dimerizes with an Fc molecule comprising SEQ ID NO: 35 (C-terminal lysine optional). In another embodiment, a GDF15-Fc fusion comprising the amino acid sequence of SEQ ID NO: 47 dimerizes with an Fc molecule comprising SEQ ID NO: 36 (C-terminal lysine optional). In another embodiment, a GDF15-Fc fusion comprising the amino acid sequence of SEQ ID NO: 48 dimerizes with an Fc molecule comprising SEQ ID NO: 36 (C-terminal lysine optional). In another embodiment, a GDF15-Fc fusion comprising the amino acid sequence of SEQ ID NO: 49 dimerizes with an Fc molecule comprising SEQ ID NO: 36 (C-terminal lysine optional). In another embodiment, a GDF15-Fc fusion comprising the amino acid sequence of SEQ ID NO: 50 dimerizes with an Fc molecule comprising SEQ ID NO: 36 (C-terminal lysine optional). In another embodiment, a GDF15-Fc fusion comprising the amino acid sequence of SEQ ID NO: 51 dimerizes with an Fc molecule comprising SEQ ID NO: 36 (C-terminal lysine optional). In another embodiment, a GDF15-Fc fusion comprising the amino acid sequence of SEQ ID NO: 52 dimerizes with an Fc molecule comprising SEQ ID NO: 36 (C-terminal lysine optional). In another embodiment, a GDF15-Fc fusion comprising the amino acid sequence of SEQ ID NO: 53 dimerizes with an Fc molecule comprising SEQ ID NO: 36 (C-terminal lysine optional). In another embodiment, a GDF15-Fc fusion comprising the amino acid sequence of SEQ ID NO: 54 dimerizes with an Fc molecule comprising SEQ ID NO: 36 (C-terminal lysine optional). In another embodiment, a GDF15-Fc fusion comprising the amino acid sequence of SEQ ID NO: 55 dimerizes with an Fc molecule comprising SEQ ID NO: 36 (C-terminal lysine optional). In another embodiment, a GDF15-Fc fusion comprising the amino acid sequence of SEQ ID NO: 56 dimerizes with an Fc molecule comprising SEQ ID NO: 37 (C-terminal lysine optional). In another embodiment, a GDF15-Fc fusion comprising the amino acid sequence of SEQ ID NO: 57 dimerizes with an Fc molecule comprising SEQ ID NO: 37 (C-terminal lysine optional).

In some embodiments, the dimers form tetramers. For example, the dimers in Table 6 can form tetramers. In some embodiments, the tetramers are formed from the same dimers. In some embodiments, two dimers of FcΔ10(−)-(G4S)4-GDF15:FcΔ10(+,K); FcΔ10(+)-(G4)-GDF15: FcΔ10(−,K); FcΔ10(−)-GDF15(Δ3):FcΔ10(+,K); FcΔ10(−)-GDF15(N3D):FcΔ10(+,K); FcΔ10(−,CC)-GDF15(Δ3): FcΔ10(+,K,CC); FcΔ10(−,CC)-GDF15(N3D):FcΔ10(+,K, CC); FcΔ16(−,CC)-GDF15(Δ3/D5E):FcΔ16(+,K,CC); FcΔ16(−,CC)-GDF15(N3Q/D5E):FcΔ16(+,K,CC); FcΔ16 (−)-GDF15(N3Q/D5E):FcΔ16(+,K); FcΔ16(−)-(G4Q)4-GDF15:FcΔ16(+,K); FcΔ16(−)-(G4Q)4-GDF15(N3Q): FcΔ16(+,K); FcΔ16(−)-(G4Q)4-GDF15(N3Q/D5E):FcΔ16 (+,K); FcΔ16(−)-(G4S)2-GDF15(N3Q):FcΔ16(+,K); FcΔ16 (−)-(G4S)2-GDF15(N3Q/D5E):FcΔ16(+,K); FcΔ16(−)-G4S-GDF15(N3Q):FcΔ16(+,K); FcΔ16(−)-G4S-GDF15 (N3Q/D5E): FcΔ16(+,K); FcΔ16(−)-GDF15(N3Q): FcΔ16 (+,K); FcΔ10(−,L234A/L235A)-(G4Q)4-GDF15(N3Q): FcΔ10(+,K,L234A/L235A); or FcΔ10(−,L234A/L235A)-(G4Q)4-GDF15(N3Q/D5E):FcΔ10(+,K,L234A/L235A) form a tetramer, such as through the dimerization of the two GDF15 regions.

Also provided herein are host cells comprising the nucleic acids and vectors for producing the GDF15 and Fc molecules disclosed herein. In various embodiments, the vector or nucleic acid is integrated into the host cell genome, which in other embodiments the vector or nucleic acid is extrachromosomal.

Recombinant cells, such as yeast, bacterial (e.g., *E. coli*), and mammalian cells (e.g., immortalized mammalian cells) comprising such a nucleic acid, vector, or combinations of either or both thereof are provided. In various embodiments, cells comprising a non-integrated nucleic acid, such as a plasmid, cosmid, phagemid, or linear expression element, which comprises a sequence coding for expression of a GDF15 molecule and/or an Fc molecule. In some embodiments, the cell comprises a nucleic acid for producing a GDF15 molecule and another cell comprises a nucleic acid for producing an Fc molecule for dimerization with the GDF15 molecule (e.g., a vector for encoding a GDF15 molecule in one cell and a second vector for encoding an Fc molecule in a second cell). In other embodiments, a host cell comprises a nucleic acid for producing a GDF15 molecule and an Fc molecule (e.g., a vector that encodes both molecules). In another embodiment, a host cell comprises a nucleic acid for producing a GDF15 molecule and another nucleic acid for producing an Fc molecule (e.g., two separate vectors, one that encodes a GDF15 molecule and one that encodes an Fc molecule, in a single host cell).

A vector comprising a nucleic acid sequence encoding a GDF15 molecule and/or an Fc molecule can be introduced into a host cell by transformation or by transfection, such as by methods known in the art.

A nucleic acid encoding a GDF15 molecule can be positioned in and/or delivered to a host cell or host animal via a viral vector. A viral vector can comprise any number of viral polynucleotides, alone or in combination with one or more viral proteins, which facilitate delivery, replication, and/or expression of the nucleic acid of the invention in a desired host cell. The viral vector can be a polynucleotide comprising all or part of a viral genome, a viral protein/nucleic acid conjugate, a virus-like particle (VLP), or an intact virus particle comprising viral nucleic acids and a nucleic acid encoding a polypeptide comprising a GDF15 region. A viral particle viral vector can comprise a wild-type viral particle or a modified viral particle. The viral vector can be a vector which requires the presence of another vector or wild-type virus for replication and/or expression (e.g., a viral vector can be a helper-dependent virus), such as an adenoviral vector amplicon. Suitable viral vector particles in this respect, include, for example, adenoviral vector particles (including any virus of or derived from a virus of the adenoviridae), adeno-associated viral vector particles (AAV vector particles) or other parvoviruses and parvoviral vector particles, papillomaviral vector particles, flaviviral vectors, alphaviral vectors, herpes viral vectors, pox virus vectors, retroviral vectors, including lentiviral vectors.

A GDF15 molecule can be isolated using standard protein purification methods. A polypeptide comprising a GDF15 region can be isolated from a cell that has been engineered to express a polypeptide comprising a GDF15 region, for example a cell that does not naturally express native GDF15. Protein purification methods known in the art can be employed to isolate GDF15 molecules, as well as associated materials and reagents. Methods of purifying a GDF15 molecule are also provided in the Examples herein. Additional purification methods that may be useful for isolating GDF15 molecules can be found in references such as Bootcov MR, 1997, *Proc. Natl. Acad. Sci. USA* 94:11514-9, Fairlie WD, 2000, *Gene* 254: 67-76.

Pharmaceutical compositions comprising a GDF15 molecule (and optionally, an Fc molecule, such as a dimer or tetramer disclosed herein) are also provided. Such polypeptide pharmaceutical compositions can comprise a therapeutically effective amount of a GDF15 molecule in admixture with a pharmaceutically or physiologically acceptable formulation agent or carrier selected for suitability with the mode of administration. The pharmaceutically or physiologically acceptable formulation agent can be one or more formulation agents suitable for accomplishing or enhancing the delivery of a GDF15 molecule into the body of a human or non-human subject. Pharmaceutically acceptable substances such as wetting or emulsifying agents, preservatives or buffers, which enhance the shelf life or effectiveness of the GDF15 molecule can also act as, or form a component of, a formulation carrier. Acceptable pharmaceutically acceptable carriers are preferably nontoxic to recipients at the dosages and concentrations employed. The pharmaceutical composition can contain formulation agent(s) for modifying, maintaining, or preserving, for example, the pH, osmolarity, viscosity, clarity, color, isotonicity, odor, sterility, stability, rate of dissolution or release, adsorption, or penetration of the composition.

The effective amount of pharmaceutical composition comprising a GDF15 molecule which is to be employed therapeutically will depend, for example, upon the therapeutic context and objectives. One skilled in the art will appreciate that the appropriate dosage levels for treatment will thus vary depending, in part, upon the molecule delivered, the indication for which a GDF15 molecule is being used, the route of administration, and the size (body weight, body surface, or organ size) and condition (the age and general health) of the subject. The frequency of dosing will depend upon the pharmacokinetic parameters of the GDF15 molecule in the formulation being used.

The route of administration of the pharmaceutical composition can be orally; through injection by intravenous, intraperitoneal, intracerebral (intraparenchymal), intracerebroventricular, intramuscular, intraocular, intraarterial, intraportal, or intralesional routes; by sustained release systems (which may also be injected); or by implantation devices. Where desired, the compositions can be administered by bolus injection or continuously by infusion, or by an implantation device. The composition can also be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

A GDF15 molecule can be used to treat, diagnose or ameliorate, a metabolic condition or disorder. In one embodiment, the metabolic disorder is diabetes, e.g., type 2 diabetes. In another embodiment, the metabolic condition or disorder is obesity. In other embodiments, the metabolic condition or disorder is dyslipidemia, elevated glucose levels, elevated insulin levels or diabetic nephropathy. For example, a metabolic condition or disorder that can be treated or ameliorated using a GDF15 molecule includes a state in which a human subject has a fasting blood glucose level of 125 mg/dL or greater, for example 130, 135, 140, 145, 150, 155, 160, 165, 170, 175, 180, 185, 190, 195, 200 or greater than 200 mg/dL. Blood glucose levels can be determined in the fed or fasted state, or at random. The metabolic condition or disorder can also comprise a condition in which a subject is at increased risk of developing a metabolic condition. For a human subject, such conditions include a fasting blood glucose level of 100 mg/dL. Conditions that can be treated using a pharmaceutical composition comprising a GDF15 molecule can also be found in the American Diabetes Association Standards of Medical Care in Diabetes Care 2011, American Diabetes Association, *Diabetes Care* Vol. 34, No. Supplement 1, S11-S61, 2010.

The administration can be performed such as by intravenous (IV) injection, intraperitoneal (IP) injection, subcutaneous injection, intramuscular injection, or orally in the form of a tablet or liquid formation. A therapeutically effective dose of a GDF15 molecule will depend upon the administration schedule, the unit dose of agent administered, whether the GDF15 molecule is administered in combination with other therapeutic agents, the immune status and the health of the recipient. A therapeutically effective dose is an amount of a GDF15 molecule that elicits a biological or medicinal response in a tissue system, animal, or human being sought by a researcher, medical doctor, or other clinician, which includes alleviation or amelioration of the symptoms of the disease or disorder being treated, i.e., an amount of a GDF15 molecule that supports an observable level of one or more desired biological or medicinal response, for example, lowering blood glucose, insulin, triglyceride, or cholesterol levels; reducing body weight; improving glucose tolerance, energy expenditure, or insulin sensitivity; or reducing food intake. A therapeutically effective dose of a GDF15 molecule can also vary with the desired result.

Also provided herein is a method comprising measuring a baseline level of one or more metabolically-relevant compounds such as glucose, insulin, cholesterol, lipid in a subject, administering a pharmaceutical composition comprising a GDF15 molecule to the subject, and after a desired period of time, measure the level of the one or more metabolically-relevant compounds (e.g., blood glucose, insulin, cholesterol, lipid) in the subject. The two levels can then be compared to determine the relative change in the metabolically-relevant compound in the subject. Depending on the outcome of that comparison another dose of the pharmaceutical composition can be administered to achieve a desired level of one or more metabolically-relevant compound.

A pharmaceutical composition comprising a GDF15 molecule can be co-administered with another compound or therapeutic agent. A GDF15 molecule (and optionally, its corresponding Fc molecule) can be administered in combination with another therapeutic agent, such as an agent that lowers blood glucose, insulin, triglyceride, or cholesterol levels; lowers body weight; reduces food intake; improves glucose tolerance, energy expenditure, or insulin sensitivity; or any combination thereof (e.g., antidiabetic agent, hypolipidemic agent, anti-obesity agent, anti-hypertensive agent, or agonist of peroxisome proliferator-activator receptor). The identity and properties of a compound co-administered with the GDF15 molecule will depend on the nature of the condition to be treated or ameliorated. The agent administered with a GDF15 molecule disclosed herein can be a GLP-1R agonist, such as GLP-1 or an analog thereof; or an exendin, exendin analog, or exendin agonist. A non-limiting list of examples of compounds that can be administered in combination with the pharmaceutical composition include liraglutide, rosiglitizone, pioglitizone, repaglinide, nateglitinide, metformin, exenatide, stiagliptin, pramlintide, glipizide, glimepirideacarbose, orlistat, lorcaserin, phenterminetopiramate, naltrexonebupropion, setmelanotide, semaglutide, efpeglenatide, canagliflozin, LIK-066, SAR-425899, Tt-401, FGFR4Rx, HDV-biotin and miglitol.

In one embodiment, a GDF15 molecule comprising the amino acid sequence of SEQ ID NO: 39, 40, 41, 42, 43, 44, 45, 46, 47, 48, 49, 50, 51, 52, 53, 54, 55, 56 or 57 is administered with another compound or therapeutic agent, such as liraglutide.

In another embodiment, a GDF15 molecule and corresponding Fc molecule comprising the amino acid sequences of SEQ ID NOs: 39 and 32 (C-terminal lysine optional), respectively; SEQ ID NOs: 40 and 33 (C-terminal lysine optional), SEQ ID NOs: 41 and 32 (C-terminal lysine optional), respectively; SEQ ID NOs: 42 and 32 (C-terminal lysine optional), respectively; SEQ ID NOs: 43 and 34 (C-terminal lysine optional), respectively; SEQ ID NOs: 44 and 34 (C-terminal lysine optional), respectively; SEQ ID NOs: 45 and 35 (C-terminal lysine optional), respectively; SEQ ID NOs: 46 and 35 (C-terminal lysine optional), respectively; SEQ ID NOs: 47 and 36 (C-terminal lysine optional) respectively; SEQ ID NOs: 48 and 36 (C-terminal lysine optional), respectively; SEQ ID NOs: 49 and 36 (C-terminal lysine optional) respectively; SEQ ID NOs: 50 and 36 (C-terminal lysine optional), respectively; SEQ ID NOs: 51 and 36 (C-terminal lysine optional), respectively; SEQ ID NOs: 52 and 36 (C-terminal lysine optional), respectively; SEQ ID NOs: 53 and 36 (C-terminal lysine optional), respectively; SEQ ID NOs: 54 and 36 (C-terminal lysine optional), respectively; SEQ ID NOs: 55 and 36 (C-terminal lysine optional), respectively; SEQ ID NOs: 56 and 37 (C-terminal lysine optional), respectively; or SEQ ID NOs: 57 and 37 (C-terminal lysine optional), respectively; is administered with another compound or therapeutic agent, such as liraglutide.

In another embodiment, a GDF15 molecule and corresponding Fc molecule comprising the amino acid sequences of SEQ ID NOs: 50 and 36 (C-terminal lysine optional), respectively, is administered with another compound or therapeutic agent, such as liraglutide. In another embodiment, a GDF15 molecule and corresponding Fc molecule comprising the amino acid sequences of SEQ ID NOs: 57 and 37 (C-terminal lysine optional), respectively, is administered with another compound or therapeutic agent, such as liraglutide.

A GDF15 molecule administered with another therapeutic agent can include concurrent administration of a therapeutically effective amount of the GDF15 molecule (and optionally, its corresponding Fc molecule) and a therapeutically effective amount of the other therapeutic agent. A GDF15 molecule administered with another therapeutic agent can include subsequent administration of a therapeutically effective amount of the GDF15 molecule (and optionally, its corresponding Fc molecule) and a therapeutically effective amount of the other therapeutic agent, e.g., administration of a therapeutically effective amount of the GDF15 molecule (and optionally, its corresponding Fc molecule) followed by a therapeutically effective amount of the other therapeutic agent or administration of a therapeutically effective amount of the other therapeutic agent followed by administration of a therapeutically effective amount of the GDF15 molecule (and optionally, its corresponding Fc molecule). Administration of a therapeutically effective amount of the GDF15 molecule (and optionally, its corresponding Fc molecule) can be at least 1, 2, 3, 4, 5, 6, or 7 days after administration of a therapeutically effective amount of the other therapeutic agent. In another embodiment, administration of a therapeutically effective amount of a therapeutically effective amount of the other therapeutic agent can be at least 1, 2, 3, 4, 5, 6, or 7 days after at least 1, 2, 3, 4, 5, 6, or 7 days after administration of a therapeutically effective amount of the GDF15 molecule (and optionally, its corresponding Fc molecule).

A GDF15 molecule administered concurrently with another therapeutic agent can comprise administration of a composition comprising both the GDF15 molecule (and optionally its corresponding Fc molecule) and the other therapeutic agent, e.g., a therapeutically effective amount of the GDF15 molecule (and optionally its corresponding Fc molecule) is combined with a therapeutically effective amount of the other agent prior to administration. In another embodiment, concurrent administration of GDF15 molecule (and optionally its corresponding Fc molecule) and another therapeutic agent can comprise concurrent administration of a first composition comprising the GDF15 molecule and a second composition comprising the other therapeutic agent.

In some embodiments, administration of a GDF15 molecule with another therapeutic agent has a synergistic effect. In one embodiment, the effect is greater than the GDF15 molecule (and optionally its corresponding Fc molecule) alone or the other agent. In another embodiment, the effect is greater than an additive effect of both agents (the GDF15 molecule, and optionally its corresponding Fc molecule, plus the other agent). In one embodiment, combination therapy (i.e., administration of a GDF15 molecule, optionally with its corresponding Fc molecule, with another therapeutic agent) has a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than GDF15 monotherapy (administration of the GDF15 molecule, and optionally its corresponding Fc molecule). In another embodiment, combination therapy (i.e., administration of a GDF15 molecule, optionally with its corresponding Fc molecule, with another therapeutic agent) has a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than monotherapy with the other agent. The effect can be the amount of body weight lost (e.g., the decrease in total mass or percent body change); the decrease in blood glucose, insulin, triglyceride, or cholesterol levels; the improvement in glucose tolerance, energy expenditure, or insulin sensitivity; or the reduction food intake. The synergistic effect can be about 1, 2, 3, 4, 5, 6, 7, 8, 9, 10, 11, 12, 13, 14, 21, 28, 35, 42, 49, 56, 63, or 70 days after administration.

In one embodiment, a GDF15 molecule and corresponding Fc molecule comprising the amino acid sequences of SEQ ID NOs: 39 and 32 (C-terminal lysine optional), respectively; SEQ ID NOs: 40 and 33 (C-terminal lysine optional), SEQ ID NOs: 41 and 32 (C-terminal lysine optional), respectively; SEQ ID NOs: 42 and 32 (C-terminal lysine optional), respectively; SEQ ID NOs: 43 and 34 (C-terminal lysine optional), respectively; SEQ ID NOs: 44 and 34 (C-terminal lysine optional), respectively; SEQ ID NOs: 45 and 35 (C-terminal lysine optional), respectively; SEQ ID NOs: 46 and 35 (C-terminal lysine optional), respectively; SEQ ID NOs: 47 and 36 (C-terminal lysine optional) respectively; SEQ ID NOs: 48 and 36 (C-terminal lysine optional), respectively; SEQ ID NOs: 49 and 36 (C-terminal lysine optional) respectively; SEQ ID NOs: 50 and 36 (C-terminal lysine optional), respectively; SEQ ID NOs: 51 and 36 (C-terminal lysine optional), respectively; SEQ ID NOs: 52 and 36 (C-terminal lysine optional), respectively; SEQ ID NOs: 53 and 36 (C-terminal lysine optional), respectively; SEQ ID NOs: 54 and 36 (C-terminal lysine optional), respectively; SEQ ID NOs: 55 and 36 (C-terminal lysine optional), respectively; SEQ ID NOs: 56 and 37 (C-terminal lysine optional), respectively; or SEQ ID NOs: 57 and 37 (C-terminal lysine optional), respectively; administered with a GLP-1R agonist (e.g., liraglutide or exendin, or an analog or agonist thereof) has a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than GDF15 monotherapy; a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than GLP-1R agonist monotherapy (i.e., administration of GLP-1R agonist alone); or both, about 1, 2, 3, 4, 5, 6, 7, 8, 9, 10, 11, 12, 13, 14, 21, 28, 35, 42, 49, 56, 63, or 70 days after administration of the agent(s).

The detailed description and following examples illustrate the present invention and are not to be construed as limiting the present invention thereto. Various changes and modifications can be made by those skilled in the art on the basis of the description of the invention, and such changes and modifications are also included in the present invention.

EXAMPLES

The following examples, including the experiments conducted and results achieved, are provided for illustrative purposes only and are not to be construed as limiting the present invention.

Example 1: GDF15(WT)-Linker-Fc Molecules

The GDF15 molecules of scFc-GDF15 (SEQ ID NO: 38) and FcΔ10(−)-(G4S)4-GDF15 (SEQ ID NO: 39) were produced and the activity of the molecules tested.

FcΔ10(−)-(G4S)4-GDF15 (SEQ ID NO: 39) was stably expressed in a serum free, suspension adapted CHO-K1 cell line. It was cloned into a stable expression vector containing puromycin resistance while the Fc chain for forming a heterodimer with FcΔ10(−)-(G4S)4-GDF15, FcΔ10(+,K) (SEQ ID NO: 32), was cloned into a hygromycin containing expression vector (Selexis, Inc.). The plasmids were transfected at a 1:1 ratio using lipofectamine LTX and cells were selected 2 days post transfection in a proprietary growth media containing 10 ug/mL puromycin and 600 ug/mL hygromycin. Media was exchanged 2 times per week during selection. When cells reached about 90% viability, they were scaled up for a batch production run. Cells were seeded at 2×10⁶/mL in production media. The conditioned medium (CM) produced by the cells was harvested on day 7 and clarified. Endpoint viabilities typically were above 90%.

FcΔ10(−)-(G4S)4-GDF15 (SEQ ID NO: 39) (and any paired Fc) were clarified. Conditioned media was purified using a two-step chromatography procedure. Approximately 5 L of the CM was applied directly to a GE MabSelect SuRe column that had previously been equilibrated with Dulbecco's Phosphate Buffered Saline (PBS). The bound protein underwent three wash steps: first, 3 column volumes (CV) of PBS; next, 1 CV of 20 mM Tris, 100 mM sodium chloride, pH 7.4; and finally, 3 CV of 500 mM L-arginine, pH 7.5. These wash steps remove unbound or lightly bound media components and host cell impurities. The column was then re-equilibrated with 5 CV of 20 mM Tris, 100 mM sodium chloride at pH 7.4 which brought the UV absorbance back to baseline. The desired protein was eluted with 100 mM acetic acid at pH 3.6 and collected in bulk. The protein pool was quickly titrated to within a pH range of 5.0 to 5.5 with 1 M Tris-HCl, pH 9.2. The pH adjusted protein pool was next loaded onto a GE SP Sepharose® HP column that had been previously equilibrated with 20 mM 2-ethanesulfonic acid (MES) at pH 6.0. The bound protein was then washed with 5 CV of equilibration buffer, and finally eluted over a 20 CV, 0 to 50% linear gradient from 0 to 400 mM sodium chloride in 20 mM MES at pH 6.0. Fractions were collected during the elution and analyzed by analytical size-exclusion chromatography (Superdex® 200) to determine the appropriate fractions to pool for a homogeneous product. The SP HP chromatography removes product-related impurities such as free Fc, clipped species, and Fc-GDF15 multimers. The SP HP pool was then buffer exchanged into 10 mM sodium acetate, 5% proline, pH 5.2 by dialysis. It was concentrated to approximately 15 mg/ml using the Sartorius Vivaspin® 20 ten kilo-dalton molecular weight cut-off centrifugal device. Finally, it was sterile filtered and the resulting solution containing the purified Fc-GDF15 molecules was stored at 5° C. Final products were assessed for identity and purity using mass spectral analysis, sodium dodecyl sulfate polyacrylamide electrophoresis and size exclusion high performance liquid chromatography.

ScFc-GDF15 (SEQ ID NO: 38) was produced in a similar manner. This GDF15 molecule was stably expressed in a CHO/CS9 cell line. The molecules were cloned into a stable expression vector. The plasmids (linearized) were transfected at a 1:1 ratio using electroporation and cells were selected 2 days post transfection. Media was exchanged 3 times per week during selection. When cells reached about 90% viability, they were scaled up for a fed batch production run. Cells were seeded at 1×10⁶/mL in production media and fed once when the cell number reached to 4-5×10⁶/ml. The conditioned medium (CM) produced by the cells was harvested on day 10 and clarified. Endpoint viabilities typically were above 90%. ScFc-GDF15 was clarified and conditioned media was purified using a two-step coupled chromatography procedure. Conditioned media from multiple harvests were pooled and concentrated nearly 5 fold by ultrafiltration using a 1 sq ft Pellicon® 2 10 kD regenerated cellulose membrane (Millipore) by tangential flow filtration. Approximately 5 L of the concentrated CM was applied directly to a GE MabSelect SuRe column that had previously been equilibrated with Dulbecco's Phosphate Buffered Saline (PBS). The non-specifically bound protein was removed by a 12CV PBS wash step. The desired protein was eluted with 0.5% acetic acid at pH 3.5, 150 mM NaCl in 3 CV and collected in a storage loop. The collected protein pool was directly loaded onto a GE HiLoad 26/60 Superdex 200 Prep Grade sizing column that had been previously equilibrated with 30 mM acetate at pH 5.0, 150 mM NaCl. Peak fractions collected during the sizing run were analyzed by sodium dodecyl sulfate polyacrylamide gel electrophoresis to determine the appropriate fractions to pool for a homogeneous product. The pH of the final sizing-pool was adjusted to pH 4.5, with the addition of 10% glacial acetic acid and then buffer exchanged into 10 mM sodium acetate, 9% (w/v) sucrose, pH 4.5 by dialysis. It was concentrated to above 15 mg/ml using a ten kilo-dalton molecular weight cut-off centrifugal device. Protein stability to freezing was tested by 3 cycles of freezing and thawing. Finally, the final lot was sterile filtered and the resulting solution containing the purified GDF15 molecules was stored at −80° C. Final products were assessed for identity and purity using mass spectral analysis, n-terminal sequencing, sodium dodecyl sulfate polyacrylamide electrophoresis and size exclusion high performance liquid chromatography.

Activity of scFc-GDF15 and FcΔ10(−)-(G4S)4-GDF15 was then analyzed for in vivo activity. Cynomologus monkeys (n=10 per group) were administered vehicle, 3 mg/kg of the positive control FGF21-Fc, 1.5 mg/kg of scFc-GDF15, or 1.5 mg/kg of FcΔ10(−)-(G4S)4-GDF15:FcΔ10 (+,K) weekly for six weeks, followed by a five-week washout. Body weight and triglyceride levels were determined. Naïve male spontaneously obese cynomolgus monkeys were prescreened for health and had a body mass index >41. Monkeys were acclimated to single housing, experimental procedures and handling for 6 weeks prior to treatment. Monkeys were sorted into 4 groups receiving once weekly SC injection for 6 weeks (days 0, 7, 14, 21, 28, and 35) for each group to have similar baseline. Overnight fasting blood samples were collected at pre-dose days −24, −17 and −10, and on days 6, 13, 20, 27, 34, and 41 (6 days after each weekly dose) during the treatment phase. During the washout phase, blood samples were collected on days 48, 55, 62, 69 and 76. Body weight was measured once a week and food intake was monitored daily for each monkey throughout the study. Each monkey received unlimited feed for a limited amount of time (1 hour) at the morning and evening feeding, approximately 8 hours apart. A 150 g apple snack, for a limited amount of time (1 hour), was provided between meals. The remaining food or apple was removed and weighed after each meal or snack to calculate food intake.

Figure 2:
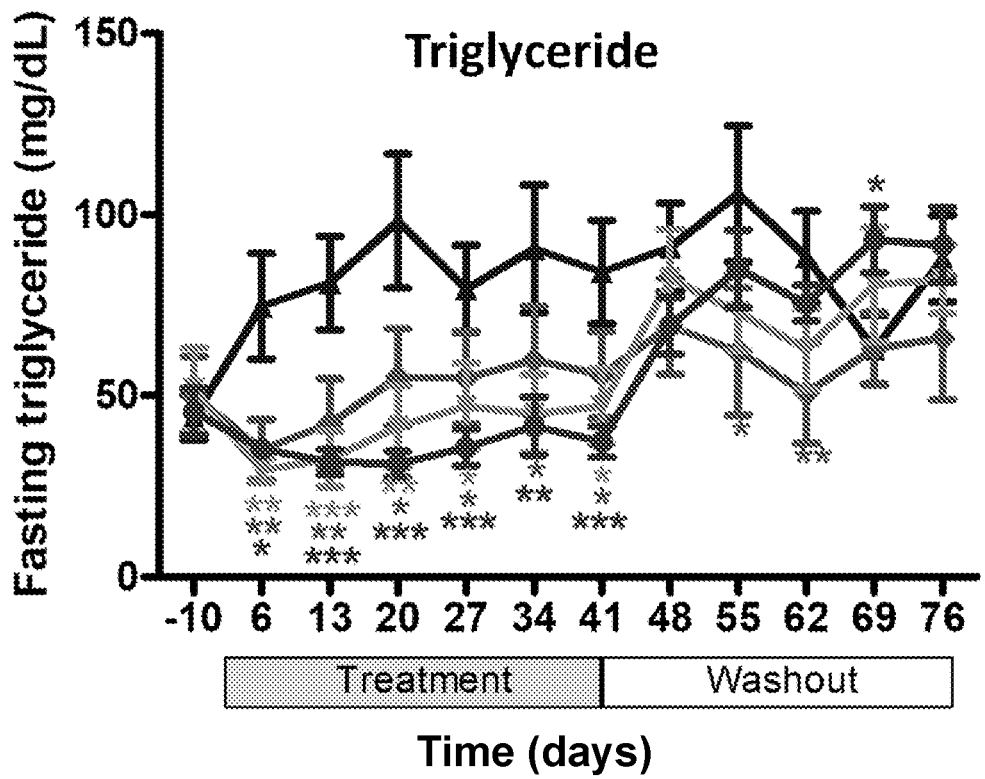
FIG. 2 is a plot showing the effect on the triglyceride levels of cynomologus monkeys dosed with vehicle, 3 mg/kg of the positive control FGF21-Fc, 1.5 mg/kg of scFc-GDF15, or 1.5 mg/kg of the dimer FcΔ10(-)-(G4S)4-GDF15:FcΔ10(+,K) weekly for six weeks, followed by a five-week washout.

GDF15-Fc fusion proteins reduced body weight (FIG. 1) and triglyceride levels (FIG. 2), similar to FGF21-Fc.

Example 2: GDF15(WT)-Linker-Fc Molecule Attributes

The FcΔ10(−)-(G4S)4-GDF15 (SEQ ID NO: 39) molecule as described in Example 1 and FcΔ10(+)-(G4)-GDF15 (SEQ ID NO: 40) were analyzed for attributes that may affect its stability and manufacturability (e.g., for commercial manufacturing). The GDF15 molecules (e.g., FcΔ10(−)-(G4S)4-GDF15 and FcΔ10(+)-(G4)-GDF15) were determined to be highly heterogeneous (e.g., analysis of an ion exchange column fraction of FcΔ10(−)-(G4S)4-GDF15 shows the molecule is highly heterogeneous, FIG. 3), an undesirable feature for manufacturability of a molecule. To determine the attributes of the GDF15 molecules that result in a highly heterogenous population, analysis of the molecules by size exclusion chromatography, SDS PAGE gel, and mass spectrometry was performed. A lack of difference in retention time by size exclusion chromatography indicated that aggregation or gross degradation are unlikely to be responsible for the heterogeneity. There was also a lack of difference on an SDS PAGE gel, which indicated that disulfide mispairing or gross degradation are also unlikely to be responsible for the heterogeneity.

MS analysis was also performed to evaluate the heterogeneity of FcΔ10(−)-(G4S)4-GDF15 (SEQ ID NO: 39). The GDF15 molecule was purified using mono S, 1 ml column and fraction number 25 (P1), fraction number 28 (P2), and fraction number 31 (P3) (FIG. 3) were collected and submitted for MS analysis. About 50 µg of the fractions were dried down, resuspended in 25 µL of 150 mM Tris, pH 7.5/8M urea/40 mM hydroxylamine/10 mM DTT, and then incubated for 1 hour at 37° C. The samples were alkylated with 20 mM iodoacetamide (IAM) for 30 minutes at room temperature in the dark. The samples were then diluted to 100 µL with water and 2 µg of trypsin (1:25) and digested overnight at 37° C. The digests were acidified, followed by injection onto a Waters (Milford, MA) NanoAcquity UPLC system. Samples were first loaded onto a 180 µm×20 mm Symmetry C18 trapping column at 15 µL/min, followed by peptide separation on an Agilent (Santa Clara, CA) Zorbax 0.5 mm×250 mm 300SB-C18 column. Buffer A was 0.1% formic acid/water, while buffer B was 0.10% formic acid/ 99.9% acetonitrile. The gradient consisted of initial conditions at 1% B, followed by an increase to 45% B over 85 minutes, to 97% B over 1 minute, isocratic at 97% B for 6 minutes, to 1% B over 3 minutes, and then isocratic at 1% B for 20 minutes. The UPLC column effluent was sprayed into a Thermo Fisher Scientific (San Jose, CA) Orbitrap Velos Pro mass spectrometer using the standard heated electrospray ionization II (HESI II) ionization source. The mass spectrometer method consisted of a full MS scan of m z [300-2000] at 30K resolution, followed by MS/MS (CID activation) of the top 10 most abundant precursor ions. The following instrument parameters were used for the analysis: source voltage=3.5 kV; capillary temperature=275° C.; S-lens RF level=50%; activation time=10 msec; normalized collision energy=35; isolation width=2.0 Da; and threshold=1.0E4. The Xtract component of the Thermo Xcalibur 2.1 software was used for deconvolution of high-resolution MS data. Averaged data from [300-2000] were deconvoluted using a S/N threshold of 1.2 and a resolution of 100,000 at m z 400. Deconvoluted peptide masses (glycosylated and non-glycosylated) were displayed as monoisotopic [M+H]⁺. The various glycosylated species were confirmed by the stepwise loss of glycan subunits and the presence of the unglycosylated precursor ion as the most intense fragment following CID activation.

Figure 3:
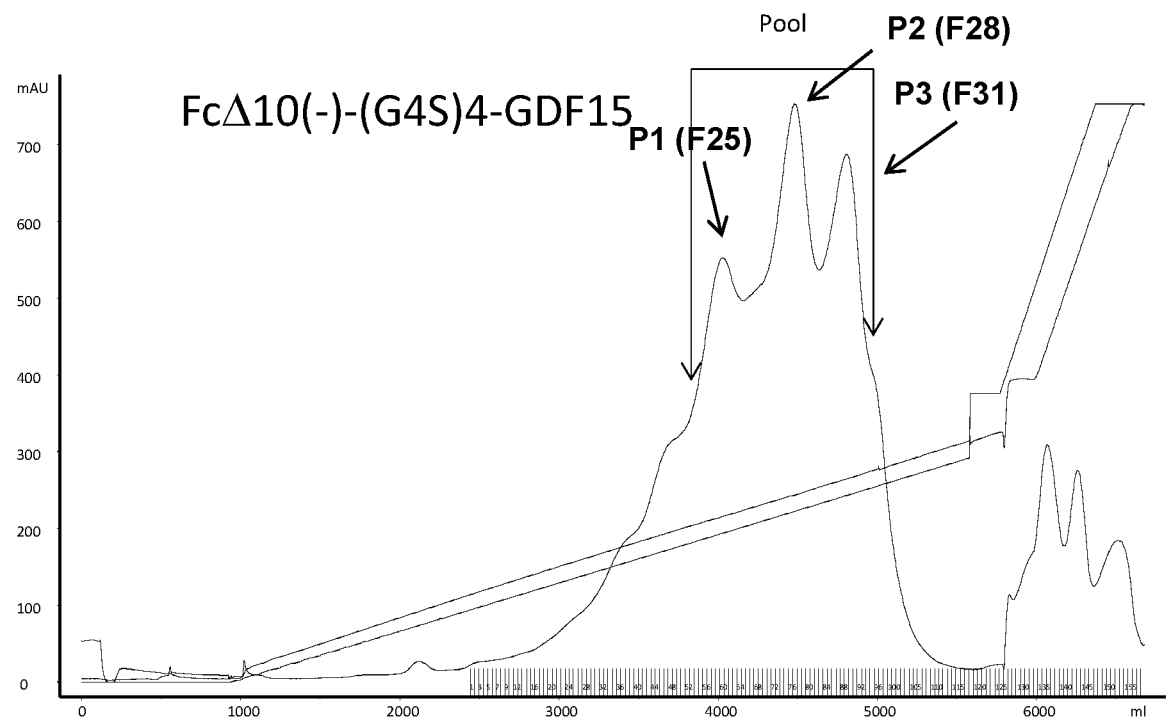
FIG. 3 shows the profile of FcΔ10(-)-(G4S)4-GDF15 after cation exchange.
Figure 4:
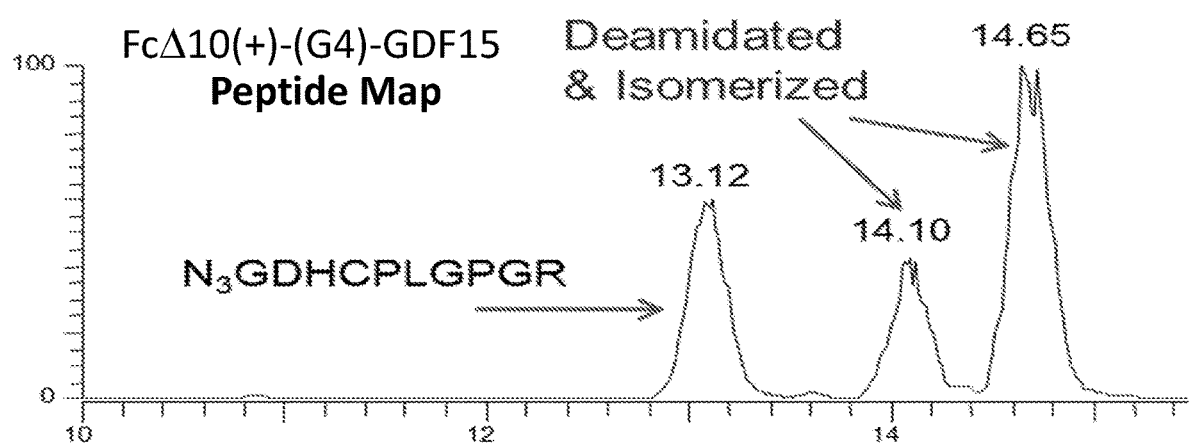
FIG. 4 is a peptide map of FcΔ10(+)-(G4)-GDF15.

The MS results showed that the varying degrees of deamidated species (e.g., 70% of P1, 47% of P2, and 24% of P3) and glycosylation distribution (mostly monosaccharide and trisaccharide) on the linker contributed to highly heterogeneous nature of the GDF15 molecule as shown in its CEX profile (FIG. 3). It was determined that the (G4S)4 linker (e.g., present in FcΔ10(−)-(G4S)4-GDF15) was highly glycosylated and phosphorylated, with varying degrees and types of glycosylation and/or phosphorylation, and the N-terminus of the active fragment of wildtype human GDF15 was highly susceptible to deamidation and isomerization (see e.g., FIG. 4, which shows certain masses extracted from the full mass spec data that correspond to the unmodified, deamidated, and isomerized species of the peptide that contains asparagine at position 3. The extracted masses were m z [590.25-590.75] from the doubly charged versions of the peptide). The asparagine at position 3 (in reference to SEQ ID NO: 6, the amino acid sequence encoding the active fragment of hGDF15) was highly susceptible to deamidation and isomerization and the aspartate at position 5 (in reference to SEQ ID NO: 6, the amino acid sequence encoding the active fragment of hGDF15) was highly susceptible to isomerization.

Based on these attributes, manufacturing a generally homogenous population of a GDF15-Fc fusion protein having the active fragment of wild type human GDF15 with a linker to the Fc region (e.g., for commercial manufacturing) would be challenging.

Example 3: Activity of GDF15-Fc Fusion Proteins Without a Linker

To address the heterogeneity issues described in Example 2, new GDF15-Fc fusion proteins that 1) eliminated the linker between the GDF15 region and the Fc region and 2) eliminated or substituted the N-terminal residues of the active fragment of wild-type human GDF15 (e.g., GDF15 (Δ3) (SEQ ID NO: 13), where the first three amino acids of the active fragment of wild type human GDF15 is deleted, or GDF15(N3D) (SEQ ID NO: 16), in which the asparagine at position 3 of the active fragment of wild type human GDF15 is mutated to aspartate).

In addition to the charged pair mutation in the Fc region of the GDF15-Fc fusion protein and the Fc molecule for the non-covalent association of the Fc molecule to the Fc region of the GDF15-Fc fusion protein to form a heterodimer, some of the new molecules were designed to also include an interchain disulfide bond in the CH3 region, or "cysteine clamp" (molecules that include "CC" in their designation) to augment the heterodimerization of the GDF-Fc molecule with an Fc molecule.

Four new GDF15-Fc fusion proteins in which 1) the linker between the GDF15 region and the Fc region was deleted and 2) the N-terminal residues of GDF15 were eliminated or substituted were generated. In two of the four molecules, an interchain disulfide bond was also introduced into the CH3 domain of the Fc region of the GDF15-Fc fusion protein (as well as its corresponding Fc molecule for heterodimerization). The potency and pharmacokinetic (PK) properties of these molecules (FcΔ10(−)-GDF15(Δ3) (SEQ ID NO: 41); FcΔ10(−)-GDF15(N3D) (SEQ ID NO: 42); FcΔ10(−,CC)-GDF15(Δ3) (SEQ ID NO: 43); FcΔ10(−,CC)-GDF15(N3D) (SEQ ID NO: 44)) were compared to the earlier generation FcΔ10(−)-(G4S)4-GDF15 (SEQ ID NO: 39), in mice.

Figure 5:
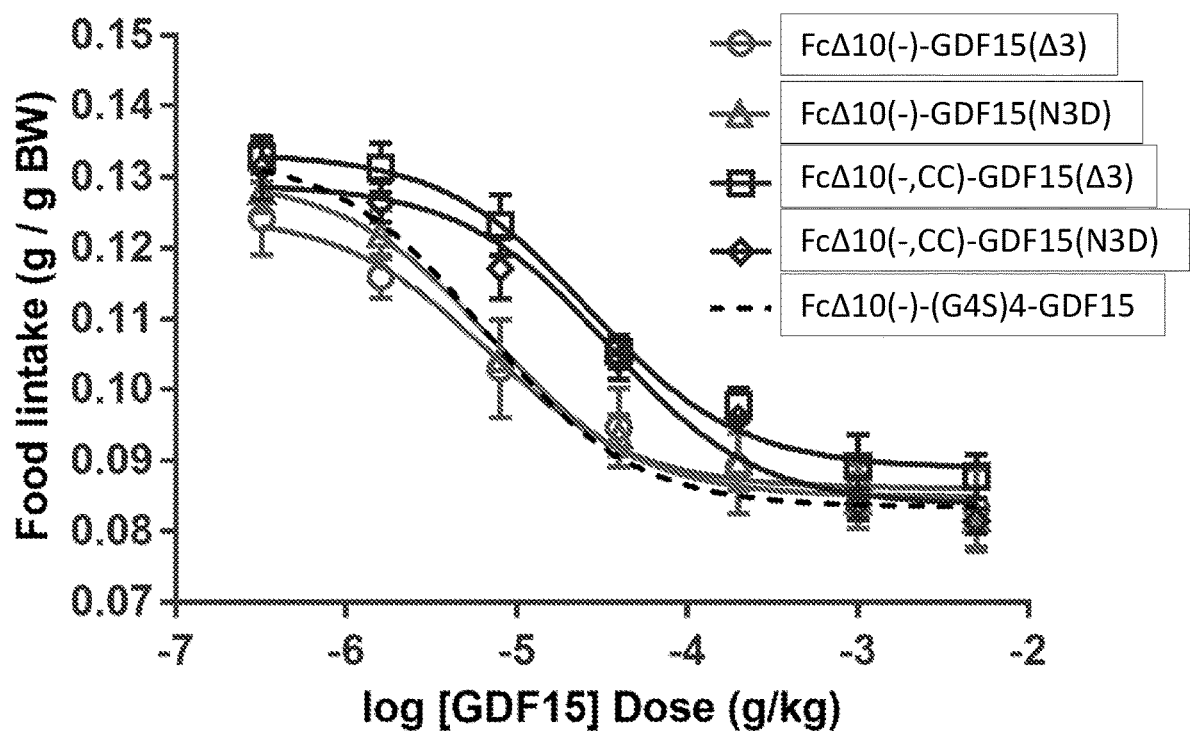
FIG. 5 is a graph showing the effect on food intake in mice as a function of dose of the dimers FcΔ10(-)-GDF15(Δ3): FcΔ10(+,K) (SEQ ID NOs: 41 and 32); FcΔ10(-)-GDF15 (N3D):FcΔ10(+,K) (SEQ ID NOs: 42 and 32); FcΔ10(-, CC)-GDF15(Δ3):FcΔ10(+,K,CC) (SEQ ID NOs: 43 and 34); FcΔ10(-,CC)-GDF15(N3D):FcΔ10(+,K,CC) (SEQ ID NOs: 44 and 34)) and FcΔ10(-)-(G4S)4-GDF15:FcΔ10(+, K) (SEQ ID NOs:39 and 32).

To determine the potency of the molecules, food intake was determined. Seven to eight-week old single-housed male ob/ob mice were sorted into different treatment groups with each group having comparable pretreatment body weight and food intake levels. Animals were treated with 0.32 ug/kg, 1.6 ug/kg, 8 ug/kg, 40 ug/kg, 0.2 mg/kg, 1 mg/kg, or 5 mg/kg of a GDF15-Fc fusion protein (a dimer of FcΔ10(−)-GDF15(Δ3):FcΔ10(+,K) (SEQ ID NOs: 41 and 32); FcΔ10(−)-GDF15(N3D):FcΔ10(+,K) (SEQ ID NOs: 42 and 32); or FcΔ10(−,CC)-GDF15(Δ3):FcΔ10(+,K,CC) (SEQ ID NOs: 39 and 32)) through subcutaneous injection, and overnight food intake was measured. Data presented is an average of 2-4 independent studies (FIG. 5). The four new molecules, FcΔ10(−)-GDF15(Δ3) (SEQ ID NO: 41); FcΔ10(−)-GDF15(N3D) (SEQ ID NO: 42); FcΔ10(−,CC)-GDF15(Δ3) (SEQ ID NO: 43); and FcΔ10(−,CC)-GDF15 (N3D) (SEQ ID NO: 44), had comparable potency as the earlier generation GDF15-Fc fusion protein, FcΔ10(−)-(G4S)4-GDF15 (SEQ ID NO: 39).

Figure 6:
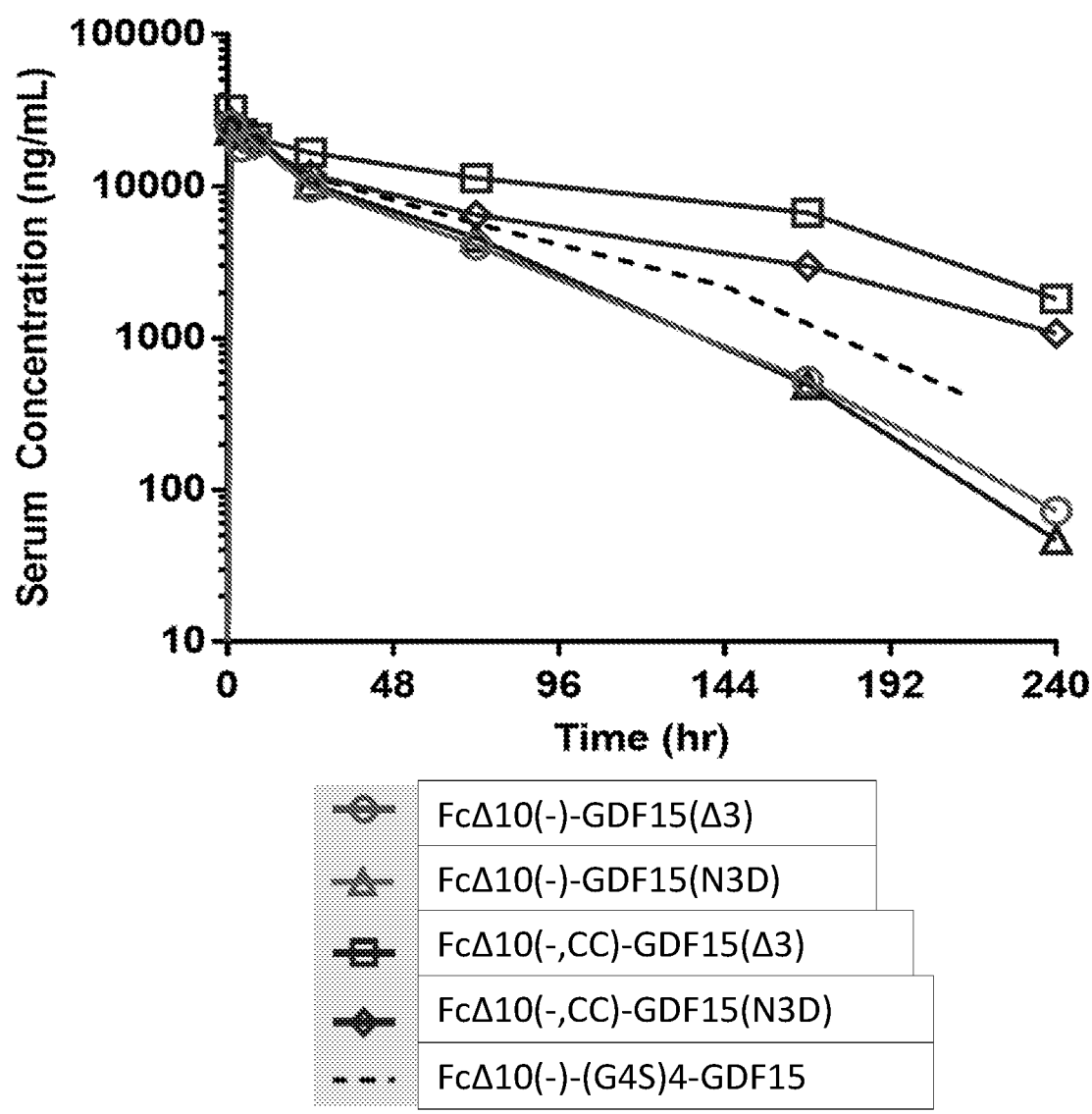
FIG. 6 is a graph of the serum concentration of FcΔ10 (-)-GDF15(Δ3) (SEQ ID NO: 41); FcΔ10(-)-GDF15(N3D) (SEQ ID NO: 42); FcΔ10(-,CC)-GDF15(Δ3) (SEQ ID NO: 43); and FcΔ10(-,CC)-GDF15(N3D) (SEQ ID NO: 44)) as a function of time in mice.

To determine the pharmacokinetics of the molecules, 18-wk old male diet-induced obese C57Bl/6 mice were dosed with 1 mg/kg protein subcutaneously, and serial sampling was performed at 1, 4, 8, 24, 72, 168, 240, and 336 hr post-dose. The four new molecules, FcΔ10(−)-GDF15 (Δ3) (SEQ ID NO: 41); FcΔ10(−)-GDF15(N3D) (SEQ ID NO: 42); FcΔ10(−,CC)-GDF15(Δ3) (SEQ ID NO: 43); and FcΔ10(−,CC)-GDF15(N3D) (SEQ ID NO: 44), had comparable pharmacokinetic properties as the earlier generation GDF15-Fc fusion protein, FcΔ10(−)-(G4S)4-GDF15 (SEQ ID NO: 39) (FIG. 6).

Example 4: Further Engineering of GDF15-Fc Fusion Proteins without a Linker

As the newly designed molecules with improved manufacturability and stability attributes had similar potency and PK properties as the earlier generation molecule, the molecules were further engineered to reduce possible heterogeneity and reduce Fc effector function and increase potency.

To further reduce heterogeneity of the GDF15 region, instead of substituting the asparagine at position 3 with aspartate, the asparagine was substituted with glutamine. In addition, the molecules were engineered to have two changes introduced in the N-terminus of GDF15, e.g., GDF15(Δ3/D5E) (SEQ ID NO: 17), GDF15(N3Q/D5E) (SEQ ID NO: 18) to eliminate the high rate of deamidation and isomerization of the native GDF15 protein. To reduce Fc effector function by and improve potency, the molecules were also engineered to have the hinge region of the Fc region deleted further by having an additional six amino acids deleted from the Fc hinge region (e.g., FcΔ16 instead of FcΔ10) to decrease binding to FcγR. The same engineering of the hinge region was performed for the corresponding Fc molecules to which the GDF15-Fc fusion proteins heterodimerize with.

The activity of the further engineered GDF15-Fc fusion proteins, FcΔ16(−,CC)-GDF15(Δ3/D5E) (SEQ ID NO: 45), FcΔ16(−,CC)-GDF15(N3Q/D5E) (SEQ ID NO: 46), and FcΔ16(−)-GDF15(N3Q/D5E) (SEQ ID NO: 47), were tested in cynomologus monkeys. Naïve male spontaneously obese cynomolgus monkeys were acclimated/trained to procedural manipulations (e.g., blood collection, subcutaneous injection, body weight measurement, feeding schedule) for 10 weeks prior to treatment initiation. Eighty (80) monkeys were sorted into 8 treatment groups of n=10 monkeys each based on data collected during acclimation/training phase (blood chemistries and body weight). Each treatment group was administered vehicle, 3 mg/kg of the positive control FGF21-Fc, 0.5 mg/kg of FcΔ16(−,CC)-GDF15(Δ3/D5E) (along with its heterodimerization partner, FcΔ16(+,K,CC) (SEQ ID NO: 35)), 3.0 mg/kg of FcΔ16(−,CC)-GDF15(Δ3/D5E) (along with its heterodimerization partner, FcΔ16(+,K,CC) (SEQ ID NO: 35)), 0.5 mg/kg of FcΔ16(−,CC)-GDF15(N3Q/D5E) (along with its heterodimerization partner, FcΔ16(+,K,CC)), 3.0 mg/kg of FcΔ16(−,CC)-GDF15(N3Q/D5E) (along with its heterodimerization partner, FcΔ16(+,K,CC)), 0.5 mg/kg of FcΔ16(−)-GDF15(N3Q/D5E) (along with its heterodimerization partner, FcΔ16(+,K) (SEQ ID NO: 36)), or 3.0 mg/kg of FcΔ16(−)-GDF15 (N3Q/D5E) (along with its heterodimerization partner, FcΔ16(+,K) (SEQ ID NO: 36)). Subcutaneous injections of each were given once a week for 4 weeks during the treatment phase followed by a 4-week washout phase; blood collection and body weight monitoring occurred weekly and food intake occurred daily during treatment and washout phases. The graph represents n=5-6/group and data are represented as group means±SEM. Statistical analysis was performed by ANCOVA and statistical significance is denoted as *p<0.05, p<0.01 and *p<0.001 versus vehicle. Monkeys with rapid drug clearance were suspect of anti-drug antibodies (ADAs) and were excluded from analysis.

Figure 7:
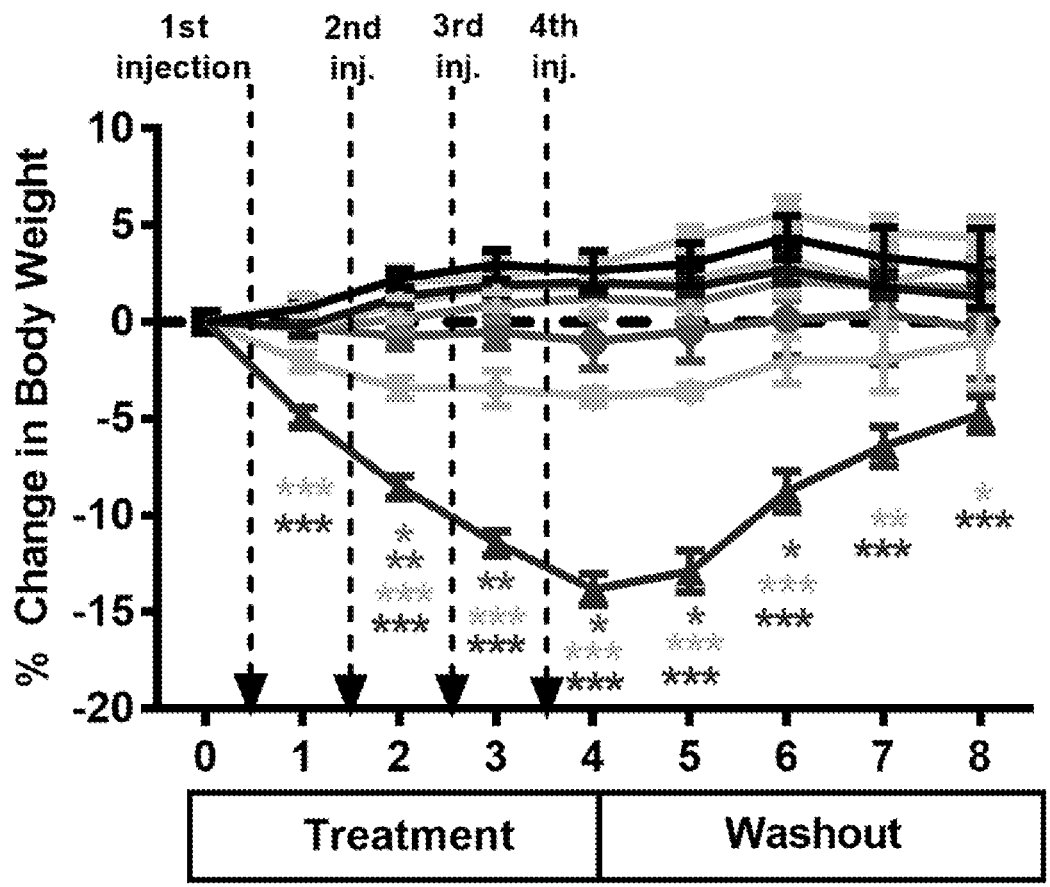
FIG. 7 is a graph showing the effect on the body weight of cynomologus monkeys dosed with vehicle, 3 mg/kg of the positive control FGF21-Fc, 0.5 mg/kg or 3.0 mg/kg of FcΔ16(−,CC)-GDF15(Δ3/D5E):FcΔ16(+,K,CC) (SEQ ID NOs: 45 and 35), 0.5 mg/kg or 3.0 mg/kg of FcΔ16(−,CC)-GDF15(N3Q/D5E):FcΔ16(+,K,CC)) (SEQ ID NOs: 46 and 35) or 0.5 mg/kg or 3.0 mg/kg of FcΔ16(−)-GDF15(N3Q/D5E):FcΔ16(+,K) (SEQ ID NOs: 47 and 36) weekly for four weeks, followed by a four-week washout.

Unexpectedly, the newly engineered GDF15-Fc fusion proteins lost almost all potency (FIG. 7). None of the newly engineered GDF15-Fc fusion proteins reduced body weight to a similar degree as to FGF21-Fc, in contrast to the previously generated GDF15-Fc fusion proteins (see Example 1, FIG. 1)

Example 5: Restoration of GDF15-Fc Fusion Protein Activity in Cynomologus Monkeys The GDF15-Fc fusion proteins in Example 4 as compared to the GDF15-Fc fusion protein in Example 1 had the following differences as shown in Table 7:

TABLE 7

Differences between GDF15-Fc Fusion
Proteins in Examples 1 and 4

| GDF15-Fc Molecules in Example 1: Efficacious in Cynomologus Monkeys | GDF15-Fc Molecules in Example 5: Not Efficacious in Cynomologus Monkeys |
|---|---|
| Δ10 in Fc region | Δ16 in Fc region |
| No cysteine clamp | Cysteine clamp |
| Has linker | No linker |
| Wild type GDF15 | Two mutations in N-terminus of GDF15 |

To restore potency, different aspects of the molecules that were efficacious in the monkeys were re-introduced into new GDF15-Fc fusion proteins. The cysteine clamp (CH3 interchain disulfide bond) was eliminated and a linker reintroduced for FcΔ16(−)-(G4Q)4-GDF15(N3Q) (SEQ ID NO: 49); FcΔ16(−)-(G4Q)4-GDF15(N3Q/D5E) (SEQ ID NO: 50) and FcΔ16(−)-G4S-GDF15(N3Q/D5E) (SEQ ID NO: 54). However, the linker used in this Example cannot be glycosylated (e.g., G4Q) or was shorter (G4S instead of (G4S)4), to reduce glycosylation. Also, for FcΔ16(−)-(G4Q)4-GDF15(N3Q), the mutation at position 5 was eliminated. Lastly, for the new molecule FcΔ10(−,L234A/L235A)-(G4Q)4-GDF15(N3Q/D5E) (SEQ ID NO: 57), the smaller deletion of the hinge region of the Fc region was reintroduced, however with L234A/L235A mutations in the Fc region, which should eliminate FcγR binding.

Figure 8:
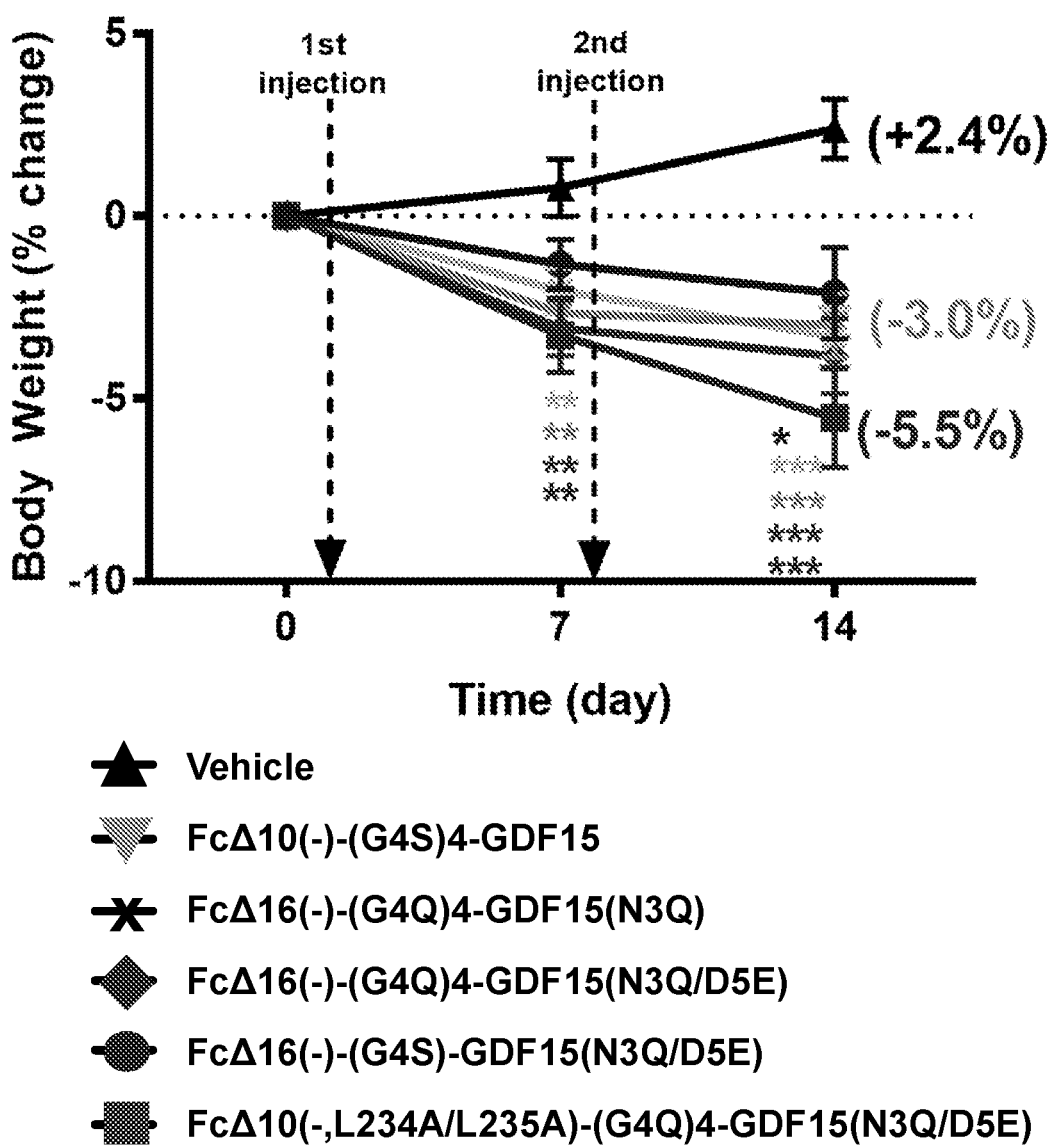
FIG. 8 is a graph showing the effect on the body weight of cynomologus monkeys dosed with vehicle, 1.5 mg/kg of FcΔ10(−)-(G4S)4-GDF15:FcΔ10(+,K) (SEQ ID NOs: 39 and 32), 1.5 mg/kg of FcΔ16(−)-(G4Q)4-GDF15(N3Q):FcΔ16(+,K) (SEQ ID NOs: 49 and 36); 1.5 mg/kg of FcΔ16(−)-(G4Q)4-GDF15(N3Q/D5E):FcΔ16(+,K) (SEQ ID NOs: 50 and 36), 1.5 mg/kg of FcΔ16(−)-G4S-GDF15(N3Q/D5E):FcΔ16(+,K) (SEQ ID NOs: 54 and 36), or 1.5 mg/kg of FcΔ10(−,L234A/L235A)-(G4Q)4-GDF15(N3Q/D5E):FcΔ10(+,K,L234A/L235A) (SEQ ID NOs: 57 and 37) weekly for two weeks.

These new molecules were compared to FcΔ10(−)-(G4S)4-GDF15, which was shown to be efficacious in cynomologus monkeys in Example 1. Naïve male spontaneously obese cynomolgus monkeys were acclimated/trained to procedural manipulations (e.g., blood collection, subcutaneous injection, body weight measurement, feeding schedule) for 2 weeks prior to treatment initiation. Forty-two (42) monkeys were sorted into 6 treatment groups of n=7 monkeys each based on data collected during acclimation/training phase (blood chemistries and body weight). Each treatment group was administered vehicle, 1.5 mg/kg of FcΔ10(−)-(G4S)4-GDF15 (along with its heterodimerization partner, FcΔ10(+,K)), 1.5 mg/kg of FcΔ16(−)-(G4Q)4-GDF15(N3Q) (along with its heterodimerization partner, FcΔ16(+, K)), 1.5 mg/kg of FcΔ16(−)-(G4Q)4-GDF15(N3Q/D5E) (along with its heterodimerization partner, FcΔ16(+,K)), 1.5 mg/kg of FcΔ16(−)-G4S-GDF15(N3Q/D5E) (along with its heterodimerization partner, FcΔ16(+,K)), or 1.5 mg/kg of FcΔ10(−,L234A/L235A)-(G4Q)4-GDF15(N3Q/D5E) (along with its heterodimerization partner, FcΔ10(+,K, L234A/L235A) (SEQ ID NO: 37). Subcutaneous injections were given once a week for 2 weeks during the treatment phase; blood collection and body weight monitoring occurred weekly and food intake was monitored daily during the treatment phase. The graph represents n=7/group and data is represented as group means±SEM. Statistical analysis was performed by ANCOVA and statistical significance is denoted as *p<0.05, p<0.01 and *p<0.001 versus vehicle. The new molecules restored potency (FIG. 8).

Based on these results, the N3Q mutation was determined to not impact the GDF15 activity in the monkeys, and that the double mutation in GDF15 (N3Q/D5E) also did not impact GDF15 activity in the monkeys. The 16-amino acid Fc hinge deletion (Δ16) was also shown to have a similar effect as the 10-amino acid Fc hinge deletion (Δ10) in the monkeys. Lastly, the linker was shown to be a critical component for activity in the monkeys. Though whether the linker is a G4S or G4Q does not affect activity, the length of the linker is important for activity. The longer linkers (e.g., (G4S)4 and (G4Q)4 in FIG. 8) are more potent as compared to a shorter linker (e.g., G4S).

Example 6: Food Intake Assay in Ob/Ob Mice for FcΔ16(−)-(G4Q)4-GDF15(N3Q/D5E) and FcΔ10(−, L234A/L235A)-(G4Q)4-GDF15(N3Q/D5E)

Figure 9:
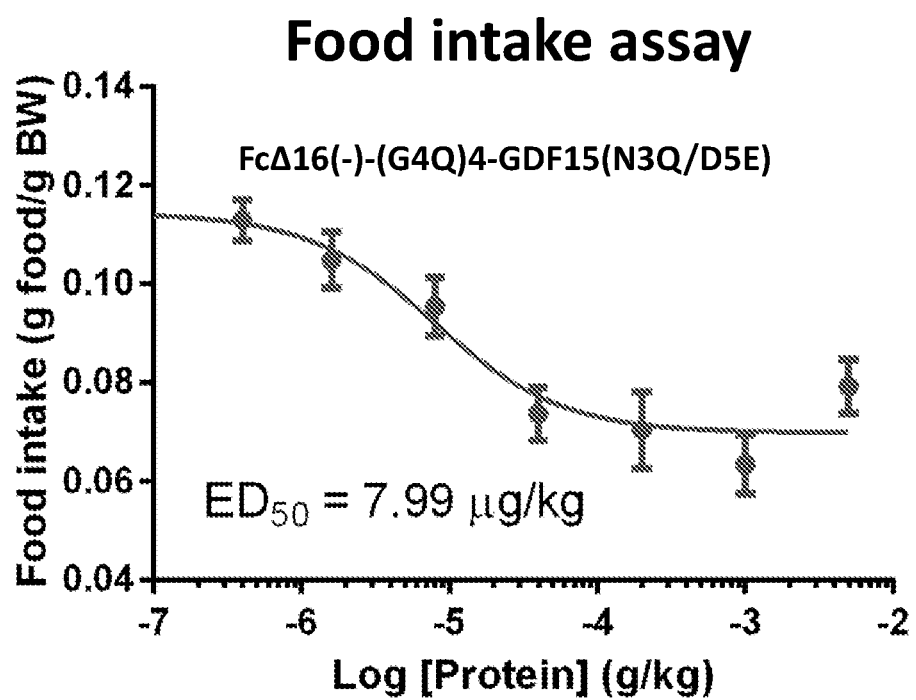
FIG. 9 is a graph of food intake as a function of dose in ob/ob mice administered FcΔ16(−)-(G4Q)4-GDF15(N3Q/D5E):FcΔ16(+,K) (SEQ ID NOs: 50 and 36).
Figure 10:
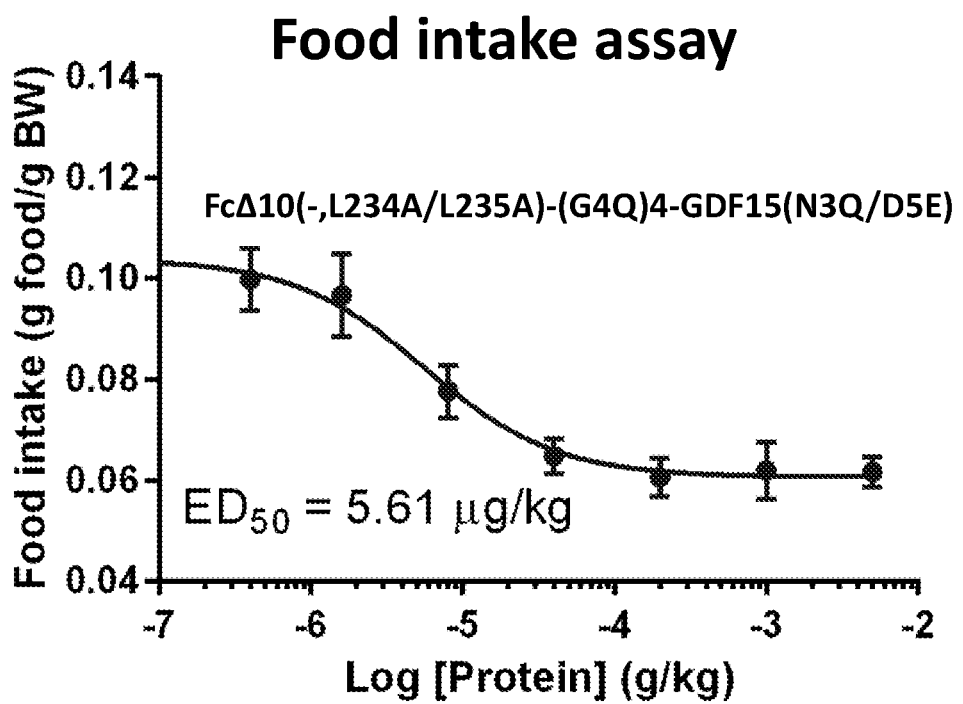
FIG. 10 is a graph of food intake as a function of dose in ob/ob mice administered FcΔ10(−,L234A/L235A)-(G4Q)4-GDF15(N3Q/D5E):FcΔ10(+,K,L234A/L235A) (SEQ ID NOs: 57 and 37).

A food intake assay was used to evaluate efficacy of two different GDF15-Fc fusion proteins. Seven to eight weeks-old single-housed male ob/ob mice were sorted into different treatment groups (n=5 per group) with each group having comparable pretreatment body weight and food intake levels. Animals were treated with 0.32 ug/kg, 1.6 ug/kg, 8 ug/kg, 40 ug/kg, 0.2 mg/kg, 1 mg/kg, or 5 mg/kg of the heterodimer FcΔ16(−)-(G4Q)4-GDF15(N3Q/D5E):FcΔ16(+,K) or FcΔ10(−,L234A/L235A)-(G4Q)4-GDF15(N3Q/D5E):FcΔ10(+,K,L234A/L235A) through subcutaneous injection, and overnight food intake was measured. The results of a representative experiment for each GDF15-Fc fusion protein is shown in a dose response curve for FcΔ16(−)-(G4Q)4-GDF15(N3Q/D5E) (FIG. 9) and FcΔ10(−, L234A/L235A)-(G4Q)4-GDF15(N3Q/D5E) (FIG. 10). The results show both GDF15-Fc fusion proteins reduce food intake in acute ob/ob mice. The ED50 in this assay is shown in Table 8.

TABLE 8

ED50 in Food Intake Assay

| Molecule | ED50 (mg/kg) n = 3-5 |
|---|---|
| FcΔ16(−)-(G4Q)4-GDF15(N3Q/D5E) | 7.4 ± 4.2 |
| FcΔ10(−, L234A/L235A)-(G4Q)4-GDF15(N3Q/D5E) | 5.8 ± 0.7 |

While the present invention has been described in terms of various embodiments, it is understood that variations and modifications will occur to those skilled in the art. Therefore, it is intended that the appended claims cover all such equivalent variations that come within the scope of the invention as claimed. In addition, the section headings used herein are for organizational purposes only and are not to be construed as limiting the subject matter described.

All references cited in this application are expressly incorporated by reference herein for any purpose.

What is claimed is:

1. A method for reducing body weight and/or food intake in a subject in need thereof, comprising administering to the subject a fusion protein comprising a GDF15 region joined to an Fc region via a linker, wherein the GDF15 region comprises the amino acid sequence of SEQ ID NO: 6, except for having mutations at the asparagine residue at position 3 of SEQ ID NO: 6 and the aspartate residue at position 5 of SEQ ID NO: 6, wherein the aspartate at position 5 of SEQ ID NO: 6 is substituted with glutamate, and wherein the linker is a $(G_4Q)_n$ linker, wherein n is greater than 2.

2. A method for reducing body weight and/or food intake in a subject in need thereof, comprising administering to the subject a fusion protein comprising the amino acid sequence of SEQ ID NO: 50.

3. The method of claim 1, wherein n is 3 or 4.

4. The method of claim 3, wherein n is 4.

5. The method of claim 1, wherein the asparagine at position 3 is substituted with glutamine.

6. The method of claim 1, wherein the GDF15 region comprises the amino acid sequence of SEQ ID NO: 18.

7. The method of claim 6, wherein the Fc region comprises a charged pair mutation.

8. The method of claim 6, wherein the Fc region comprises a truncated hinge region.

9. The method of claim 1, wherein the Fc region comprises the amino acid sequence of SEQ ID NO: 30.

10. A method for reducing body weight and/or food intake in a subject in need thereof, comprising administering to the subject a dimer comprising a fusion protein comprising the amino acid sequence of SEQ ID NO: 50 and a protein comprising the amino acid sequence of SEQ ID NO: 36.

11. A method for reducing body weight and/or food intake in a subject in need thereof, comprising administering to the subject a tetramer comprising a dimer comprising a fusion protein comprising the amino acid sequence of SEQ ID NO: 50 and a protein comprising the amino acid sequence of SEQ ID NO: 36.

12. The method of claim 1, wherein the method comprises reducing body weight in the subject.

13. The method of claim 1, wherein the method comprises reducing food intake in the subject.

14. The method of claim 2, wherein the method comprises reducing body weight in the subject.

15. The method of claim 2, wherein the method comprises reducing food intake in the subject.

16. The method of claim 10, wherein the method comprises reducing body weight in the subject.

17. The method of claim 10, wherein the method comprises reducing food intake in the subject.

18. The method of claim 11, wherein the method comprises reducing body weight in the subject.

19. The method of claim 11, wherein the method comprises reducing food intake in the subject.

* * * * *

SEQUENCE LISTING

<160> NUMBER OF SEQ ID NOS: 58

<210> SEQ ID NO 1
<211> LENGTH: 927
<212> TYPE: DNA
<213> ORGANISM: Homo sapiens

<400> SEQUENCE: 1

```
atgcccgggc aagaactcag gacggtgaat ggctctcaga tgctcctggt gttgctggtg      60
ctctcgtggc tgccgcatgg gggcgccctg tctctggccg aggcgagccg cgcaagtttc     120
ccgggaccct cagagttgca ctccgaagac tccagattcc gagagttgcg gaaacgctac     180
gaggacctgc taaccaggct gcgggccaac cagagctggg aagattcgaa caccgacctc     240
gtcccggccc ctgcagtccg gatactcacg ccagaagtgc ggctgggatc cggcggccac     300
ctgcacctgc gtatctctcg ggccgccctt cccgaggggc tcccgaggc ctcccgcctt      360
caccgggctc tgttccggct gtccccgacg gcgtcaaggt cgtgggacgt gacacgaccg     420
ctgcggcgtc agctcagcct tgcaagaccc caggcgcccg cgctgcacct gcgactgtcg     480
ccgccgccgt cgcagtcgga ccaactgctg cagaatctt cgtccgcacg gccccagctg      540
gagttgcact tgcggccgca agccgccagg gggcgccgca gagcgcgtgc gcgcaacggg     600
gaccactgtc cgctcgggcc cggcgttgc tgccgtctgc acacggtccg cgcgtcgctg      660
gaagacctgg gctgggccga ttgggtgctg tcgccacggg aggtgcaagt gaccatgtgc     720
atcggcgcgt gcccgagcca gttccggggcg gcaaacatgc acgcgcagat caagacgagc     780
ctgcaccgcc tgaagcccga cacggtgcca gcgccctgct gcgtgcccgc cagctacaat     840
cccatggtgc tcattcaaaa gaccgacacc ggggtgtcgc tccagaccta tgatgacttg     900
ttagccaaag actgccactg catatga                                         927
```

<210> SEQ ID NO 2
<211> LENGTH: 308
<212> TYPE: PRT
<213> ORGANISM: Homo sapiens

<400> SEQUENCE: 2

```
Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190
```

-continued

```
Arg Arg Ala Arg Ala Arg Asn Gly Asp His Cys Pro Leu Gly Pro Gly
            195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
    275                 280                 285

Asp Thr Gly Val Ser Leu Gln Thr Tyr Asp Asp Leu Leu Ala Lys Asp
290                 295                 300

Cys His Cys Ile
305
```

<210> SEQ ID NO 3
<211> LENGTH: 840
<212> TYPE: DNA
<213> ORGANISM: Homo sapiens

<400> SEQUENCE: 3

```
ctgtctctgg ccgaggcgag ccgcgcaagt ttcccgggac cctcagagtt gcactccgaa      60
gactccagat tccgagagtt gcggaaacgc tacgaggacc tgctaaccag gctgcgggcc     120
aaccagagct gggaagattc gaacaccgac ctcgtcccgg cccctgcagt ccggatactc     180
acgccagaag tgcggctggg atccggcggc cacctgcacc tgcgtatctc tcgggccgcc     240
cttcccgagg ggctccccga ggcctcccgc cttaccgggg ctctgttccg gctgtccccg     300
acggcgtcaa ggtcgtggga cgtgacacga ccgctgcggc gtcagctcag ccttgcaaga     360
ccccaggcgc ccgcgctgca cctgcgactg tcgccgccgc cgtcgcagtc ggaccaactg     420
ctggcagaat cttcgtccgc acggccccag ctggagttgc acttgcggcc gcaagccgcc     480
aggggggcgcc gcagagcgcg tgcgcgcaac ggggaccact gtccgctcgg gcccgggcgt     540
tgctgccgtc tgcacacggt ccgcgcgtcg ctggaagacc tgggctgggc cgattgggtg     600
ctgtcgccac gggaggtgca agtgaccatg tgcatcggcg cgtgcccgag ccagttccgg     660
gcggcaaaca tgcacgcgca gatcaagacg agcctgcacc gcctgaagcc cgacacggtg     720
ccagcgccct gctgcgtgcc cgccagctac aatcccatgg tgctcattca aaagaccgac     780
accggggtgt cgctccagac ctatgatgac ttgttagcca aagactgcca ctgcatatga     840
```

<210> SEQ ID NO 4
<211> LENGTH: 279
<212> TYPE: PRT
<213> ORGANISM: Homo sapiens

<400> SEQUENCE: 4

```
Leu Ser Leu Ala Glu Ala Ser Arg Ala Ser Phe Pro Gly Pro Ser Glu
1               5                   10                  15

Leu His Ser Glu Asp Ser Arg Phe Arg Glu Leu Arg Lys Arg Tyr Glu
            20                  25                  30

Asp Leu Leu Thr Arg Leu Arg Ala Asn Gln Ser Trp Glu Asp Ser Asn
        35                  40                  45

Thr Asp Leu Val Pro Ala Pro Ala Val Arg Ile Leu Thr Pro Glu Val
    50                  55                  60
```

Arg Leu Gly Ser Gly Gly His Leu His Leu Arg Ile Ser Arg Ala Ala
65                  70                  75                  80

Leu Pro Glu Gly Leu Pro Glu Ala Ser Arg Leu His Arg Ala Leu Phe
            85                  90                  95

Arg Leu Ser Pro Thr Ala Ser Arg Ser Trp Asp Val Thr Arg Pro Leu
            100                 105                 110

Arg Arg Gln Leu Ser Leu Ala Arg Pro Gln Ala Pro Ala Leu His Leu
            115                 120                 125

Arg Leu Ser Pro Pro Ser Gln Ser Asp Gln Leu Leu Ala Glu Ser
        130                 135                 140

Ser Ser Ala Arg Pro Gln Leu Glu Leu His Leu Arg Pro Gln Ala Ala
145                 150                 155                 160

Arg Gly Arg Arg Ala Arg Ala Arg Asn Gly Asp His Cys Pro Leu
            165                 170                 175

Gly Pro Gly Arg Cys Cys Arg Leu His Thr Val Arg Ala Ser Leu Glu
            180                 185                 190

Asp Leu Gly Trp Ala Asp Trp Val Leu Ser Pro Arg Glu Val Gln Val
            195                 200                 205

Thr Met Cys Ile Gly Ala Cys Pro Ser Gln Phe Arg Ala Ala Asn Met
    210                 215                 220

His Ala Gln Ile Lys Thr Ser Leu His Arg Leu Lys Pro Asp Thr Val
225                 230                 235                 240

Pro Ala Pro Cys Cys Val Pro Ala Ser Tyr Asn Pro Met Val Leu Ile
            245                 250                 255

Gln Lys Thr Asp Thr Gly Val Ser Leu Gln Thr Tyr Asp Leu Leu
            260                 265                 270

Ala Lys Asp Cys His Cys Ile
        275

<210> SEQ ID NO 5
<211> LENGTH: 339
<212> TYPE: DNA
<213> ORGANISM: Homo sapiens

<400> SEQUENCE: 5
gcgcgcaacg gggaccactg tccgctcggg cccgggcgtt gctgccgtct gcacacggtc     60
cgcgcgtcgc tggaagacct gggctgggcc gattgggtgc tgtcgccacg ggaggtgcaa    120
gtgaccatgt gcatcggcgc gtgcccgagc cagttccggg cggcaaacat gcacgcgcag    180
atcaagacga gcctgcaccg cctgaagccc gacacggtgc cagcgccctg ctgcgtgccc    240
gccagctaca atcccatggt gctcattcaa aagaccgaca ccggggtgtc gctccagacc    300
tatgatgact tgttagccaa agactgccac tgcatatga                           339

<210> SEQ ID NO 6
<211> LENGTH: 112
<212> TYPE: PRT
<213> ORGANISM: Homo sapiens

<400> SEQUENCE: 6

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

| Pro | Ser | Gln | Phe | Arg | Ala | Ala | Asn | Met | His | Ala | Gln | Ile | Lys | Thr | Ser |
|---|---|---|---|---|---|---|---|---|---|---|---|---|---|---|---|
| | 50 | | | | | 55 | | | | | 60 | | | | |

| Leu | His | Arg | Leu | Lys | Pro | Asp | Thr | Val | Pro | Ala | Pro | Cys | Cys | Val | Pro |
|---|---|---|---|---|---|---|---|---|---|---|---|---|---|---|---|
| 65 | | | | | 70 | | | | | 75 | | | | | 80 |

| Ala | Ser | Tyr | Asn | Pro | Met | Val | Leu | Ile | Gln | Lys | Thr | Asp | Thr | Gly | Val |
|---|---|---|---|---|---|---|---|---|---|---|---|---|---|---|---|
| | | | | 85 | | | | | 90 | | | | | 95 | |

| Ser | Leu | Gln | Thr | Tyr | Asp | Asp | Leu | Leu | Ala | Lys | Asp | Cys | His | Cys | Ile |
|---|---|---|---|---|---|---|---|---|---|---|---|---|---|---|---|
| | | | 100 | | | | | 105 | | | | | 110 | | |

<210> SEQ ID NO 7
<211> LENGTH: 912
<212> TYPE: DNA
<213> ORGANISM: Mus musculus

<400> SEQUENCE: 7

```
atggccccgc cgcgctcca ggcccagcct ccaggcggct ctcaactgag gttcctgctg      60
ttcctgctgc tgttgctgct gctgctgtca tggccatcgc aggggacgc cctggcaatg     120
cctgaacagc gaccctccgg ccctgagtcc caactcaacg ccgacgagct acgggtcgc     180
ttccaggacc tgctgagccg gctgcatgcc aaccagagcc gagaggactc gaactcagaa   240
ccaagtcctg acccagctgt ccggatactc agtccagagg tgagattggg gtcccacggc   300
cagctgctac tccgcgtcaa ccgggcgtcg ctgagtcagg gtctccccga agcctaccgc   360
gtgcaccgag cgctgctcct gctgacgccg acggcccgcc cctgggacat cactaggccc   420
ctgaagcgtg cgctcagcct ccggggaccc cgtgctcccg cattacgcct gcgcctgacg   480
ccgcctccgg acctggctat gctgccctct ggcggcacgc agctggaact gcgcttacgg   540
gtagccgccg gcaggggcg ccgaagcgcg catgcgcacc caagagactc gtgcccactg   600
ggtccgggc gctgctgtca cttggagact gtgcaggcaa ctcttgaaga cttgggctgg   660
agcgactggg tgctgtcccc gcgccagctg cagctgagca tgtgcgtggg cgagtgtccc   720
cacctgtatc gctccgcgaa cacgcatgcg cagatcaaag cacgcctgca tggcctgcag   780
cctgacaagg tgcctgcccc gtgctgtgtc ccctccagct acaccccggt ggttcttatg   840
cacaggacag acagtggtgt gtcactgcag acttatgatg acctggtggc ccggggctgc   900
cactgcgctt ga                                                       912
```

<210> SEQ ID NO 8
<211> LENGTH: 303
<212> TYPE: PRT
<213> ORGANISM: Mus musculus

<400> SEQUENCE: 8

| Met | Ala | Pro | Pro | Ala | Leu | Gln | Ala | Gln | Pro | Gly | Gly | Ser | Gln | Leu |
|---|---|---|---|---|---|---|---|---|---|---|---|---|---|---|
| 1 | | | | 5 | | | | | 10 | | | | | 15 |

| Arg | Phe | Leu | Leu | Phe | Leu | Leu | Leu | Leu | Leu | Leu | Leu | Ser | Trp | Pro |
|---|---|---|---|---|---|---|---|---|---|---|---|---|---|---|
| | | | 20 | | | | | 25 | | | | | 30 | |

| Ser | Gln | Gly | Asp | Ala | Leu | Ala | Met | Pro | Glu | Gln | Arg | Pro | Ser | Gly |Pro |
|---|---|---|---|---|---|---|---|---|---|---|---|---|---|---|---|
| | | | 35 | | | | | 40 | | | | | 45 | | |

| Glu | Ser | Gln | Leu | Asn | Ala | Asp | Glu | Leu | Arg | Gly | Arg | Phe | Gln | Asp | Leu |
|---|---|---|---|---|---|---|---|---|---|---|---|---|---|---|---|
| | 50 | | | | | 55 | | | | | 60 | | | | |

| Leu | Ser | Arg | Leu | His | Ala | Asn | Gln | Ser | Arg | Glu | Asp | Ser | Asn | Ser | Glu |
|---|---|---|---|---|---|---|---|---|---|---|---|---|---|---|---|
| 65 | | | | | 70 | | | | | 75 | | | | | 80 |

| Pro | Ser | Pro | Asp | Pro | Ala | Val | Arg | Ile | Leu | Ser | Pro | Glu | Val | Arg | Leu |
|---|---|---|---|---|---|---|---|---|---|---|---|---|---|---|---|
| | | | | 85 | | | | | 90 | | | | | 95 | |

```
Gly Ser His Gly Gln Leu Leu Leu Arg Val Asn Arg Ala Ser Leu Ser
            100                 105                 110

Gln Gly Leu Pro Glu Ala Tyr Arg Val His Arg Ala Leu Leu Leu Leu
        115                 120                 125

Thr Pro Thr Ala Arg Pro Trp Asp Ile Thr Arg Pro Leu Lys Arg Ala
    130                 135                 140

Leu Ser Leu Arg Gly Pro Arg Ala Pro Ala Leu Arg Leu Arg Leu Thr
145                 150                 155                 160

Pro Pro Pro Asp Leu Ala Met Leu Pro Ser Gly Thr Gln Leu Glu
                165                 170                 175

Leu Arg Leu Arg Val Ala Ala Gly Arg Gly Arg Arg Ser Ala His Ala
            180                 185                 190

His Pro Arg Asp Ser Cys Pro Leu Gly Pro Gly Arg Cys Cys His Leu
        195                 200                 205

Glu Thr Val Gln Ala Thr Leu Glu Asp Leu Gly Trp Ser Asp Trp Val
    210                 215                 220

Leu Ser Pro Arg Gln Leu Gln Leu Ser Met Cys Val Gly Glu Cys Pro
225                 230                 235                 240

His Leu Tyr Arg Ser Ala Asn Thr His Ala Gln Ile Lys Ala Arg Leu
                245                 250                 255

His Gly Leu Gln Pro Asp Lys Val Pro Ala Pro Cys Cys Val Pro Ser
            260                 265                 270

Ser Tyr Thr Pro Val Val Leu Met His Arg Thr Asp Ser Gly Val Ser
        275                 280                 285

Leu Gln Thr Tyr Asp Asp Leu Val Ala Arg Gly Cys His Cys Ala
    290                 295                 300

<210> SEQ ID NO 9
<211> LENGTH: 816
<212> TYPE: DNA
<213> ORGANISM: Mus musculus

<400> SEQUENCE: 9
tcgcaggggg acgccctggc aatgcctgaa cagcgaccct ccggccctga gtcccaactc      60
aacgccgacg agctacgggg tcgcttccag gacctgctga gccggctgca tgccaaccag     120
agccgagagg actcgaactc agaaccaagt cctgacccag ctgtccggat actcagtcca     180
gaggtgagat tggggtccca cggccagctg ctactccgcg tcaaccgggc gtcgctgagt     240
cagggtctcc ccgaagccta ccgcgtgcac cgagcgctgc tcctgctgac gccgacggcc     300
cgcccctggg acatcactag gcccctgaag cgtgcgctca gctccgggga ccccgtgctc     360
cccgcattac gcctgcgcct gacgccgcct ccggacctgg ctatgctgcc ctctggcggc     420
acgcagctga aactgcgctt acgggtagcc gccggcaggg ggcgccgaag cgcgcatgcg     480
cacccaagag actcgtgccc actgggtccg gggcgctgct gtcacttgga gactgtgcag     540
gcaactcttg aagacttggg ctggagcgac tgggtgctgt ccccgcgcca gctgcagctg     600
agcatgtgcg tgggcgagtg tccccacctg tatcgctccg cgaacacgca tgcgcagatc     660
aaagcacgcc tgcatggcct gcagcctgac aaggtgcctg cccccgtgctg tgtcccctcc     720 agctacaccc cggtggttct tatgcacagg acagacagtg gtgtgtcact gcagacttat     780
gatgacctgg tggcccgggg ctgccactgc gcttga                               816

<210> SEQ ID NO 10
<211> LENGTH: 271
<212> TYPE: PRT
```

<213> ORGANISM: Mus musculus

<400> SEQUENCE: 10

```
Ser Gln Gly Asp Ala Leu Ala Met Pro Glu Gln Arg Pro Ser Gly Pro
1               5                   10                  15
Glu Ser Gln Leu Asn Ala Asp Glu Leu Arg Gly Arg Phe Gln Asp Leu
            20                  25                  30
Leu Ser Arg Leu His Ala Asn Gln Ser Arg Glu Asp Ser Asn Ser Glu
        35                  40                  45
Pro Ser Pro Asp Pro Ala Val Arg Ile Leu Ser Pro Glu Val Arg Leu
    50                  55                  60
Gly Ser His Gly Gln Leu Leu Leu Arg Val Asn Arg Ala Ser Leu Ser
65                  70                  75                  80
Gln Gly Leu Pro Glu Ala Tyr Arg Val His Arg Ala Leu Leu Leu Leu
                85                  90                  95
Thr Pro Thr Ala Arg Pro Trp Asp Ile Thr Arg Pro Leu Lys Arg Ala
            100                 105                 110
Leu Ser Leu Arg Gly Pro Arg Ala Pro Ala Leu Arg Leu Arg Leu Thr
        115                 120                 125
Pro Pro Pro Asp Leu Ala Met Leu Pro Ser Gly Thr Gln Leu Glu
    130                 135                 140
Leu Arg Leu Arg Val Ala Ala Gly Arg Gly Arg Arg Ser Ala His Ala
145                 150                 155                 160
His Pro Arg Asp Ser Cys Pro Leu Gly Pro Gly Arg Cys Cys His Leu
                165                 170                 175
Glu Thr Val Gln Ala Thr Leu Glu Asp Leu Gly Trp Ser Asp Trp Val
            180                 185                 190
Leu Ser Pro Arg Gln Leu Gln Leu Ser Met Cys Val Gly Glu Cys Pro
        195                 200                 205
His Leu Tyr Arg Ser Ala Asn Thr His Ala Gln Ile Lys Ala Arg Leu
    210                 215                 220
His Gly Leu Gln Pro Asp Lys Val Pro Ala Pro Cys Cys Val Pro Ser
225                 230                 235                 240
Ser Tyr Thr Pro Val Val Leu Met His Arg Thr Asp Ser Gly Val Ser
                245                 250                 255
Leu Gln Thr Tyr Asp Asp Leu Val Ala Arg Gly Cys His Cys Ala
            260                 265                 270
```

<210> SEQ ID NO 11
<211> LENGTH: 348
<212> TYPE: DNA
<213> ORGANISM: Mus musculus

<400> SEQUENCE: 11

```
agcgcgcatg cgcacccaag agactcgtgc ccactgggtc cggggcgctg ctgtcacttg      60
gagactgtgc aggcaactct tgaagacttg ggctggagcg actgggtgct gtccccgcgc     120
cagctgcagc tgagcatgtg cgtgggcgag tgtccccacc tgtatcgctc cgcgaacacg     180
catgcgcaga tcaaagcacg cctgcatggc ctgcagcctg acaaggtgcc tgccccgtgc     240
tgtgtcccct ccagctacac cccggtggtt cttatgcaca ggacagacag tggtgtgtca     300
ctgcagactt atgatgacct ggtggcccgg ggctgccact gcgcttga                  348
```

<210> SEQ ID NO 12
<211> LENGTH: 115
<212> TYPE: PRT

<213> ORGANISM: Mus musculus

<400> SEQUENCE: 12

Ser Ala His Ala His Pro Arg Asp Ser Cys Pro Leu Gly Pro Gly Arg
1               5                   10                  15

Cys Cys His Leu Glu Thr Val Gln Ala Thr Leu Glu Asp Leu Gly Trp
            20                  25                  30

Ser Asp Trp Val Leu Ser Pro Arg Gln Leu Gln Leu Ser Met Cys Val
        35                  40                  45

Gly Glu Cys Pro His Leu Tyr Arg Ser Ala Asn Thr His Ala Gln Ile
    50                  55                  60

Lys Ala Arg Leu His Gly Leu Gln Pro Asp Lys Val Pro Ala Pro Cys
65                  70                  75                  80

Cys Val Pro Ser Ser Tyr Thr Pro Val Val Leu Met His Arg Thr Asp
                85                  90                  95

Ser Gly Val Ser Leu Gln Thr Tyr Asp Asp Leu Val Ala Arg Gly Cys
            100                 105                 110

His Cys Ala
        115

<210> SEQ ID NO 13
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 13

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 14
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 14

Ala Arg Gln Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

```
Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 15
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 15

```
Ala Arg Asp Gly Asp His Cys Pro Leu Gly Pro Gly Arg Cys Cys Arg
 1                5                  10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 16
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 16

```
Ala Arg Asn Gly Glu His Cys Pro Leu Gly Pro Gly Arg Cys Cys Arg
 1                5                  10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 17
<211> LENGTH: 109
<212> TYPE: PRT

```
<213> ORGANISM: Artificial Sequence
<220> FEATURE:
<223> OTHER INFORMATION: Synthetic Polypeptide

<400> SEQUENCE: 17

Gly Glu His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 18
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 18

Ala Arg Gln Gly Glu His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 19
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 19

Gly Gly Gly Gly Ser
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Polypeptide
```

```
<400> SEQUENCE: 20

Gly Gly Gly Gly Ser Gly Gly Gly Gly Ser
1               5                   10

<210> SEQ ID NO 21
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 21

Gly Gly Gly Gly Ser Gly Gly Gly Gly Ser Gly Gly Gly Gly Ser Gly
1               5                   10                  15

Gly Gly Gly Ser
            20

<210> SEQ ID NO 22
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 22

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 23
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 23

Gly Gly Gly Gly
1

<210> SEQ ID NO 24
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 24

Gly Gly Gly Gly Gln
1               5

<210> SEQ ID NO 25
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 25

Gly Gly Gly Gly Gln Gly Gly Gly Gly Gln Gly Gly Gly Gly Gln Gly
1               5                   10                  15
```

Gly Gly Gly Gln
           20

<210> SEQ ID NO 26
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 26

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 27
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 27

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 28
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 28

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Cys Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 29
<211> LENGTH: 210
<212> TYPE: PRT
<213> ORGANISM: Artificial Sequence
<220> FEATURE:
<223> OTHER INFORMATION: Synthetic Polypeptide

<400> SEQUENCE: 29

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Cys Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly
    210
```

<210> SEQ ID NO 30
<211> LENGTH: 210
<212> TYPE: PRT
<213> ORGANISM: Artificial Sequence
<220> FEATURE:
<223> OTHER INFORMATION: Synthetic Polypeptide

<400> SEQUENCE: 30

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80
```

```
Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly
    210

<210> SEQ ID NO 31
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 31

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```

<210> SEQ ID NO 32
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 32

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 33
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 33

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

```
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 34
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 34

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Cys Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 35
<211> LENGTH: 211
<212> TYPE: PRT
<213> ORGANISM: Artificial Sequence
<220> FEATURE:
<223> OTHER INFORMATION: Synthetic Polypeptide

<400> SEQUENCE: 35

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Cys Arg Lys Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Tyr Lys Thr Thr Pro Pro
145                 150                 155                 160

Val Leu Lys Ser Asp Gly Ser Phe Phe Leu Tyr Ser Lys Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Lys
    210
```

<210> SEQ ID NO 36
<211> LENGTH: 211
<212> TYPE: PRT
<213> ORGANISM: Artificial Sequence
<220> FEATURE:
<223> OTHER INFORMATION: Synthetic Polypeptide

<400> SEQUENCE: 36

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80
```

```
Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Lys Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Lys Thr Thr Pro Pro
145                 150                 155                 160

Val Leu Lys Ser Asp Gly Ser Phe Phe Leu Tyr Ser Lys Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Lys
    210

<210> SEQ ID NO 37
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 37

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 38
<211> LENGTH: 630
<212> TYPE: PRT
<213> ORGANISM: Artificial Sequence
<220> FEATURE:
<223> OTHER INFORMATION: Fusion Protein

<400> SEQUENCE: 38

```
Gly Gly Gly Glu Arg Lys Ser Ser Val Glu Cys Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Ser His Glu Asp Pro Glu Val Gln Phe Asn Trp Tyr Val Asp
        50                  55                  60

Gly Val Glu Val His Asn Ala Lys Thr Lys Pro Arg Glu Glu Gln Phe
65                  70                  75                  80

Asn Ser Thr Phe Arg Val Val Ser Val Leu Thr Val Val His Gln Asp
                85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Gly Gly Gly Ser Gly Gly Gly Gly Ser
225                 230                 235                 240

Gly Gly Gly Gly Ser Gly Gly Gly Ser Gly Gly Gly Ser Gly
                245                 250                 255

Gly Gly Ser Gly Gly Gly Gly Ser Gly Gly Gly Ser Glu Arg
            260                 265                 270

Lys Ser Ser Val Glu Cys Pro Cys Pro Ala Pro Pro Val Ala Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser His Glu
305                 310                 315                 320

Asp Pro Glu Val Gln Phe Asn Trp Tyr Val Asp Gly Val Glu Val His
                325                 330                 335

Asn Ala Lys Thr Lys Pro Arg Glu Glu Gln Phe Asn Ser Thr Phe Arg
            340                 345                 350

Val Val Ser Val Leu Thr Val Val His Gln Asp Trp Leu Asn Gly Lys
        355                 360                 365
```

Glu Tyr Lys Cys Lys Val Ser Asn Lys Gly Leu Pro Ala Pro Ile Glu
            370                 375                 380

Lys Thr Ile Ser Lys Thr Lys Gly Gln Pro Arg Glu Pro Gln Val Tyr
385                 390                 395                 400

Thr Leu Pro Pro Ser Arg Glu Glu Met Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Met
            435                 440                 445

Leu Asp Ser Asp Gly Ser Phe Phe Leu Tyr Ser Lys Leu Thr Val Asp
450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
            485                 490                 495

Gly Ser Gly Gly Gly Ser Gly Gly Gly Ser Gly Gly Gly Gly
            500                 505                 510

Ser Gly Gly Gly Gly Ser Ala Arg Asn Gly Asp His Cys Pro Leu Gly
            515                 520                 525

Pro Gly Arg Cys Cys Arg Leu His Thr Val Arg Ala Ser Leu Glu Asp
530                 535                 540

Leu Gly Trp Ala Asp Trp Val Leu Ser Pro Arg Glu Val Gln Val Thr
545                 550                 555                 560

Met Cys Ile Gly Ala Cys Pro Ser Gln Phe Arg Ala Ala Asn Met His
            565                 570                 575

Ala Gln Ile Lys Thr Ser Leu His Arg Leu Lys Pro Asp Thr Val Pro
            580                 585                 590

Ala Pro Cys Cys Val Pro Ala Ser Tyr Asn Pro Met Val Leu Ile Gln
            595                 600                 605

Lys Thr Asp Thr Gly Val Ser Leu Gln Thr Tyr Asp Asp Leu Leu Ala
            610                 615                 620

Lys Asp Cys His Cys Ile
625                 630

<210> SEQ ID NO 39
<211> LENGTH: 348
<212> TYPE: PRT
<213> ORGANISM: Artificial Sequence
<220> FEATURE:
<223> OTHER INFORMATION: Fusion Protein

<400> SEQUENCE: 39

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
            165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Gly Gly Gly Ser Gly Gly Gly
            210                 215                 220

Gly Ser Gly Gly Gly Ser Gly Gly Gly Gly Ser Ala Arg Asn Gly
225                 230                 235                 240

Asp His Cys Pro Leu Gly Pro Gly Arg Cys Cys Arg Leu His Thr Val
            245                 250                 255

Arg Ala Ser Leu Glu Asp Leu Gly Trp Ala Asp Trp Val Leu Ser Pro
            260                 265                 270

Arg Glu Val Gln Val Thr Met Cys Ile Gly Ala Cys Pro Ser Gln Phe
            275                 280                 285

Arg Ala Ala Asn Met His Ala Gln Ile Lys Thr Ser Leu His Arg Leu
            290                 295                 300

Lys Pro Asp Thr Val Pro Ala Pro Cys Cys Val Pro Ala Ser Tyr Asn
305                 310                 315                 320

Pro Met Val Leu Ile Gln Lys Thr Asp Thr Gly Val Ser Leu Gln Thr
            325                 330                 335

Tyr Asp Asp Leu Leu Ala Lys Asp Cys His Cys Ile
            340                 345

<210> SEQ ID NO 40
<211> LENGTH: 332
<212> TYPE: PRT
<213> ORGANISM: Artificial Sequence
<220> FEATURE:
<223> OTHER INFORMATION: Fusion Protein

<400> SEQUENCE: 40

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
            100                 105                 110
```

```
Pro Arg Glu Pro Gln Val Tyr Thr Leu Pro Pro Ser Arg Lys Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Gly Gly Ala Arg Asn Gly
    210                 215                 220

Asp His Cys Pro Leu Gly Pro Gly Arg Cys Cys Arg Leu His Thr Val
225                 230                 235                 240

Arg Ala Ser Leu Glu Asp Leu Gly Trp Ala Asp Trp Val Leu Ser Pro
                245                 250                 255

Arg Glu Val Gln Val Thr Met Cys Ile Gly Ala Cys Pro Ser Gln Phe
            260                 265                 270

Arg Ala Ala Asn Met His Ala Gln Ile Lys Thr Ser Leu His Arg Leu
        275                 280                 285

Lys Pro Asp Thr Val Pro Ala Pro Cys Cys Val Pro Ala Ser Tyr Asn
    290                 295                 300

Pro Met Val Leu Ile Gln Lys Thr Asp Thr Gly Val Ser Leu Gln Thr
305                 310                 315                 320

Tyr Asp Asp Leu Leu Ala Lys Asp Cys His Cys Ile
                325                 330

<210> SEQ ID NO 41
<211> LENGTH: 325
<212> TYPE: PRT
<213> ORGANISM: Artificial Sequence
<220> FEATURE:
<223> OTHER INFORMATION: Fusion Protein

<400> SEQUENCE: 41

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140
```

```
Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Gly Asp His Cys Pro Leu Gly Pro
210                 215                 220

Gly Arg Cys Cys Arg Leu His Thr Val Arg Ala Ser Leu Glu Asp Leu
225                 230                 235                 240

Gly Trp Ala Asp Trp Val Leu Ser Pro Arg Glu Val Gln Val Thr Met
                245                 250                 255

Cys Ile Gly Ala Cys Pro Ser Gln Phe Arg Ala Ala Asn Met His Ala
                260                 265                 270

Gln Ile Lys Thr Ser Leu His Arg Leu Lys Pro Asp Thr Val Pro Ala
            275                 280                 285

Pro Cys Cys Val Pro Ala Ser Tyr Asn Pro Met Val Leu Ile Gln Lys
290                 295                 300

Thr Asp Thr Gly Val Ser Leu Gln Thr Tyr Asp Asp Leu Leu Ala Lys
305                 310                 315                 320

Asp Cys His Cys Ile
                325

<210> SEQ ID NO 42
<211> LENGTH: 328
<212> TYPE: PRT
<213> ORGANISM: Artificial Sequence
<220> FEATURE:
<223> OTHER INFORMATION: Fusion Protein

<400> SEQUENCE: 42

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175
```

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Ala Arg Asp Gly Asp His Cys Pro
    210                 215                 220

Leu Gly Pro Gly Arg Cys Cys Arg Leu His Thr Val Arg Ala Ser Leu
225                 230                 235                 240

Glu Asp Leu Gly Trp Ala Asp Trp Val Leu Ser Pro Arg Glu Val Gln
                245                 250                 255

Val Thr Met Cys Ile Gly Ala Cys Pro Ser Gln Phe Arg Ala Ala Asn
            260                 265                 270

Met His Ala Gln Ile Lys Thr Ser Leu His Arg Leu Lys Pro Asp Thr
        275                 280                 285

Val Pro Ala Pro Cys Cys Val Pro Ala Ser Tyr Asn Pro Met Val Leu
    290                 295                 300

Ile Gln Lys Thr Asp Thr Gly Val Ser Leu Gln Thr Tyr Asp Asp Leu
305                 310                 315                 320

Leu Ala Lys Asp Cys His Cys Ile
                325

<210> SEQ ID NO 43
<211> LENGTH: 325
<212> TYPE: PRT
<213> ORGANISM: Artificial Sequence
<220> FEATURE:
<223> OTHER INFORMATION: Fusion Protein

<400> SEQUENCE: 43

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Cys Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

```
Lys Ser Leu Ser Leu Ser Pro Gly Gly Asp His Cys Pro Leu Gly Pro
    210                 215                 220
Gly Arg Cys Cys Arg Leu His Thr Val Arg Ala Ser Leu Glu Asp Leu
225                 230                 235                 240
Gly Trp Ala Asp Trp Val Leu Ser Pro Arg Glu Val Gln Val Thr Met
                    245                 250                 255
Cys Ile Gly Ala Cys Pro Ser Gln Phe Arg Ala Ala Asn Met His Ala
                260                 265                 270
Gln Ile Lys Thr Ser Leu His Arg Leu Lys Pro Asp Thr Val Pro Ala
            275                 280                 285
Pro Cys Cys Val Pro Ala Ser Tyr Asn Pro Met Val Leu Ile Gln Lys
        290                 295                 300
Thr Asp Thr Gly Val Ser Leu Gln Thr Tyr Asp Asp Leu Leu Ala Lys
305                 310                 315                 320
Asp Cys His Cys Ile
                325

<210> SEQ ID NO 44
<211> LENGTH: 328
<212> TYPE: PRT
<213> ORGANISM: Artificial Sequence
<220> FEATURE:
<223> OTHER INFORMATION: Fusion Protein

<400> SEQUENCE: 44

Ala Pro Glu Leu Leu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
                20                  25                  30
Val Val Asp Val Ser His Glu Asp Pro Glu Val Lys Phe Asn Trp Tyr
            35                  40                  45
Val Asp Gly Val Glu Val His Asn Ala Lys Thr Lys Pro Arg Glu Glu
        50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
                100                 105                 110
Pro Arg Glu Pro Gln Val Cys Thr Leu Pro Pro Ser Arg Glu Glu Met
            115                 120                 125
Thr Lys Asn Gln Val Ser Leu Thr Cys Leu Val Lys Gly Phe Tyr Pro
        130                 135                 140
Ser Asp Ile Ala Val Glu Trp Glu Ser Asn Gly Gln Pro Glu Asn Asn
145                 150                 155                 160
Tyr Asp Thr Thr Pro Pro Val Leu Asp Ser Asp Gly Ser Phe Phe Leu
                165                 170                 175
Tyr Ser Asp Leu Thr Val Asp Lys Ser Arg Trp Gln Gln Gly Asn Val
                180                 185                 190
Phe Ser Cys Ser Val Met His Glu Ala Leu His Asn His Tyr Thr Gln
            195                 200                 205
Lys Ser Leu Ser Leu Ser Pro Gly Ala Arg Asp Gly Asp His Cys Pro
        210                 215                 220
Leu Gly Pro Gly Arg Cys Cys Arg Leu His Thr Val Arg Ala Ser Leu
225                 230                 235                 240
```

```
Glu Asp Leu Gly Trp Ala Asp Trp Val Leu Ser Pro Arg Glu Val Gln
                245                 250                 255

Val Thr Met Cys Ile Gly Ala Cys Pro Ser Gln Phe Arg Ala Ala Asn
            260                 265                 270

Met His Ala Gln Ile Lys Thr Ser Leu His Arg Leu Lys Pro Asp Thr
        275                 280                 285

Val Pro Ala Pro Cys Cys Val Pro Ala Ser Tyr Asn Pro Met Val Leu
    290                 295                 300

Ile Gln Lys Thr Asp Thr Gly Val Ser Leu Gln Thr Tyr Asp Asp Leu
305                 310                 315                 320

Leu Ala Lys Asp Cys His Cys Ile
                325

<210> SEQ ID NO 45
<211> LENGTH: 319
<212> TYPE: PRT
<213> ORGANISM: Artificial Sequence
<220> FEATURE:
<223> OTHER INFORMATION: Fusion Protein

<400> SEQUENCE: 45

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Cys Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Glu His Cys Pro Leu Gly Pro Gly Arg Cys Cys Arg Leu
    210                 215                 220

His Thr Val Arg Ala Ser Leu Glu Asp Leu Gly Trp Ala Asp Trp Val
225                 230                 235                 240

Leu Ser Pro Arg Glu Val Gln Val Thr Met Cys Ile Gly Ala Cys Pro
                245                 250                 255

Ser Gln Phe Arg Ala Ala Asn Met His Ala Gln Ile Lys Thr Ser Leu
            260                 265                 270
```

His Arg Leu Lys Pro Asp Thr Val Pro Ala Pro Cys Cys Val Pro Ala
            275                 280                 285

Ser Tyr Asn Pro Met Val Leu Ile Gln Lys Thr Asp Thr Gly Val Ser
    290                 295                 300

Leu Gln Thr Tyr Asp Asp Leu Leu Ala Lys Asp Cys His Cys Ile
305                 310                 315

<210> SEQ ID NO 46
<211> LENGTH: 322
<212> TYPE: PRT
<213> ORGANISM: Artificial Sequence
<220> FEATURE:
<223> OTHER INFORMATION: Fusion Protein

<400> SEQUENCE: 46

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Cys Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Ala Arg Gln Gly Glu His Cys Pro Leu Gly Pro Gly Arg Cys
    210                 215                 220

Cys Arg Leu His Thr Val Arg Ala Ser Leu Glu Asp Leu Gly Trp Ala
225                 230                 235                 240

Asp Trp Val Leu Ser Pro Arg Glu Val Gln Val Thr Met Cys Ile Gly
                245                 250                 255

Ala Cys Pro Ser Gln Phe Arg Ala Ala Asn Met His Ala Gln Ile Lys
            260                 265                 270

Thr Ser Leu His Arg Leu Lys Pro Asp Thr Val Pro Ala Pro Cys Cys
        275                 280                 285

Val Pro Ala Ser Tyr Asn Pro Met Val Leu Ile Gln Lys Thr Asp Thr
    290                 295                 300

```
Gly Val Ser Leu Gln Thr Tyr Asp Asp Leu Leu Ala Lys Asp Cys His
305                 310                 315                 320

Cys Ile
```

<210> SEQ ID NO 47
<211> LENGTH: 322
<212> TYPE: PRT
<213> ORGANISM: Artificial Sequence
<220> FEATURE:
<223> OTHER INFORMATION: Fusion Protein

<400> SEQUENCE: 47

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Ala Arg Gln Gly Glu His Cys Pro Leu Gly Pro Gly Arg Cys
    210                 215                 220

Cys Arg Leu His Thr Val Arg Ala Ser Leu Glu Asp Leu Gly Trp Ala
225                 230                 235                 240

Asp Trp Val Leu Ser Pro Arg Glu Val Gln Val Thr Met Cys Ile Gly
                245                 250                 255

Ala Cys Pro Ser Gln Phe Arg Ala Ala Asn Met His Ala Gln Ile Lys
            260                 265                 270

Thr Ser Leu His Arg Leu Lys Pro Asp Thr Val Pro Ala Pro Cys Cys
        275                 280                 285

Val Pro Ala Ser Tyr Asn Pro Met Val Leu Ile Gln Lys Thr Asp Thr
    290                 295                 300

Gly Val Ser Leu Gln Thr Tyr Asp Asp Leu Leu Ala Lys Asp Cys His
305                 310                 315                 320

Cys Ile
```

```
<210> SEQ ID NO 48
<211> LENGTH: 342
<212> TYPE: PRT
<213> ORGANISM: Artificial Sequence
<220> FEATURE:
<223> OTHER INFORMATION: Fusion Protein

<400> SEQUENCE: 48

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
                20                  25                  30

Glu Asp Pro Glu Val Lys Phe Asn Trp Tyr Val Asp Gly Val Glu Val
            35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gln Gly Gly Gly Gln Gly Gly Gly Gly
    210                 215                 220

Gln Gly Gly Gly Gln Ala Arg Asn Gly Asp His Cys Pro Leu Gly
225                 230                 235                 240

Pro Gly Arg Cys Cys Arg Leu His Thr Val Arg Ala Ser Leu Glu Asp
                245                 250                 255

Leu Gly Trp Ala Asp Trp Val Leu Ser Pro Arg Glu Val Gln Val Thr
            260                 265                 270

Met Cys Ile Gly Ala Cys Pro Ser Gln Phe Arg Ala Ala Asn Met His
        275                 280                 285

Ala Gln Ile Lys Thr Ser Leu His Arg Leu Lys Pro Asp Thr Val Pro
    290                 295                 300

Ala Pro Cys Cys Val Pro Ala Ser Tyr Asn Pro Met Val Leu Ile Gln
305                 310                 315                 320

Lys Thr Asp Thr Gly Val Ser Leu Gln Thr Tyr Asp Asp Leu Leu Ala
                325                 330                 335

Lys Asp Cys His Cys Ile
            340

<210> SEQ ID NO 49
<211> LENGTH: 342
<212> TYPE: PRT
```

<213> ORGANISM: Artificial Sequence
<220> FEATURE:
<223> OTHER INFORMATION: Fusion Protein

<400> SEQUENCE: 49

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
                20                  25                  30

Glu Asp Pro Glu Val Lys Phe Asn Trp Tyr Val Asp Gly Val Glu Val
            35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gln Gly Gly Gly Gln Gly Gly Gly
    210                 215                 220

Gln Gly Gly Gly Gln Ala Arg Gln Gly Asp His Cys Pro Leu Gly
225                 230                 235                 240

Pro Gly Arg Cys Cys Arg Leu His Thr Val Arg Ala Ser Leu Glu Asp
                245                 250                 255

Leu Gly Trp Ala Asp Trp Val Leu Ser Pro Arg Glu Val Gln Val Thr
            260                 265                 270

Met Cys Ile Gly Ala Cys Pro Ser Gln Phe Arg Ala Ala Asn Met His
        275                 280                 285

Ala Gln Ile Lys Thr Ser Leu His Arg Leu Lys Pro Asp Thr Val Pro
    290                 295                 300

Ala Pro Cys Cys Val Pro Ala Ser Tyr Asn Pro Met Val Leu Ile Gln
305                 310                 315                 320

Lys Thr Asp Thr Gly Val Ser Leu Gln Thr Tyr Asp Asp Leu Leu Ala
                325                 330                 335

Lys Asp Cys His Cys Ile
            340
```

<210> SEQ ID NO 50
<211> LENGTH: 342
<212> TYPE: PRT
<213> ORGANISM: Artificial Sequence
<220> FEATURE:
<223> OTHER INFORMATION: Fusion Protein

<400> SEQUENCE: 50

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gln Gly Gly Gly Gln Gly Gly Gly
    210                 215                 220

Gln Gly Gly Gly Gln Ala Arg Gln Gly Glu His Cys Pro Leu Gly
225                 230                 235                 240

Pro Gly Arg Cys Cys Arg Leu His Thr Val Arg Ala Ser Leu Glu Asp
                245                 250                 255

Leu Gly Trp Ala Asp Trp Val Leu Ser Pro Arg Glu Val Gln Val Thr
            260                 265                 270

Met Cys Ile Gly Ala Cys Pro Ser Gln Phe Arg Ala Ala Asn Met His
        275                 280                 285

Ala Gln Ile Lys Thr Ser Leu His Arg Leu Lys Pro Asp Thr Val Pro
    290                 295                 300

Ala Pro Cys Cys Val Pro Ala Ser Tyr Asn Pro Met Val Leu Ile Gln
305                 310                 315                 320

Lys Thr Asp Thr Gly Val Ser Leu Gln Thr Tyr Asp Asp Leu Leu Ala
                325                 330                 335

Lys Asp Cys His Cys Ile
            340
```

<210> SEQ ID NO 51
<211> LENGTH: 332
<212> TYPE: PRT
<213> ORGANISM: Artificial Sequence
<220> FEATURE:
<223> OTHER INFORMATION: Fusion Protein

<400> SEQUENCE: 51

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
                20                  25                  30

Glu Asp Pro Glu Val Lys Phe Asn Trp Tyr Val Asp Gly Val Glu Val
            35                  40                  45

His Asn Ala Lys Thr Lys Pro Arg Glu Glu Gln Tyr Asn Ser Thr Tyr
        50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Ser Gly Gly Gly Ser Ala Arg Gln Gly
210                 215                 220

Asp His Cys Pro Leu Gly Pro Gly Arg Cys Cys Arg Leu His Thr Val
225                 230                 235                 240

Arg Ala Ser Leu Glu Asp Leu Gly Trp Ala Asp Trp Val Leu Ser Pro
                245                 250                 255

Arg Glu Val Gln Val Thr Met Cys Ile Gly Ala Cys Pro Ser Gln Phe
            260                 265                 270

Arg Ala Ala Asn Met His Ala Gln Ile Lys Thr Ser Leu His Arg Leu
        275                 280                 285

Lys Pro Asp Thr Val Pro Ala Pro Cys Cys Val Pro Ala Ser Tyr Asn
290                 295                 300

Pro Met Val Leu Ile Gln Lys Thr Asp Thr Gly Val Ser Leu Gln Thr
305                 310                 315                 320

Tyr Asp Asp Leu Leu Ala Lys Asp Cys His Cys Ile
                325                 330

<210> SEQ ID NO 52
<211> LENGTH: 332
<212> TYPE: PRT
<213> ORGANISM: Artificial Sequence
<220> FEATURE:
<223> OTHER INFORMATION: Fusion Protein

<400> SEQUENCE: 52

Gly Pro Ser Val Phe Leu Phe Pro Pro Lys Pro Lys Asp Thr Leu Met
1               5                   10                  15

Ile Ser Arg Thr Pro Glu Val Thr Cys Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Ser Gly Gly Gly Gly Ser Ala Arg Gln Gly
    210                 215                 220

Glu His Cys Pro Leu Gly Pro Gly Arg Cys Cys Arg Leu His Thr Val
225                 230                 235                 240

Arg Ala Ser Leu Glu Asp Leu Gly Trp Ala Asp Trp Val Leu Ser Pro
                245                 250                 255

Arg Glu Val Gln Val Thr Met Cys Ile Gly Ala Cys Pro Ser Gln Phe
            260                 265                 270

Arg Ala Ala Asn Met His Ala Gln Ile Lys Thr Ser Leu His Arg Leu
        275                 280                 285

Lys Pro Asp Thr Val Pro Ala Pro Cys Cys Val Pro Ala Ser Tyr Asn
    290                 295                 300

Pro Met Val Leu Ile Gln Lys Thr Asp Thr Gly Val Ser Leu Gln Thr
305                 310                 315                 320

Tyr Asp Asp Leu Leu Ala Lys Asp Cys His Cys Ile
                325                 330

<210> SEQ ID NO 53
<211> LENGTH: 327
<212> TYPE: PRT
<213> ORGANISM: Artificial Sequence
<220> FEATURE:
<223> OTHER INFORMATION: Fusion Protein

<400> SEQUENCE: 53

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

```
His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
            115                 120                 125

Leu Thr Cys Leu Val Lys Gly Phe Tyr Pro Ser Asp Ile Ala Val Glu
        130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Ser Ala Arg Gln Gly Asp His Cys Pro Leu
210                 215                 220

Gly Pro Gly Arg Cys Cys Arg Leu His Thr Val Arg Ala Ser Leu Glu
225                 230                 235                 240

Asp Leu Gly Trp Ala Asp Trp Val Leu Ser Pro Arg Glu Val Gln Val
                245                 250                 255

Thr Met Cys Ile Gly Ala Cys Pro Ser Gln Phe Arg Ala Ala Asn Met
            260                 265                 270

His Ala Gln Ile Lys Thr Ser Leu His Arg Leu Lys Pro Asp Thr Val
        275                 280                 285

Pro Ala Pro Cys Cys Val Pro Ala Ser Tyr Asn Pro Met Val Leu Ile
290                 295                 300

Gln Lys Thr Asp Thr Gly Val Ser Leu Gln Thr Tyr Asp Asp Leu Leu
305                 310                 315                 320

Ala Lys Asp Cys His Cys Ile
                325

<210> SEQ ID NO 54
<211> LENGTH: 327
<212> TYPE: PRT
<213> ORGANISM: Artificial Sequence
<220> FEATURE:
<223> OTHER INFORMATION: Fusion Protein

<400> SEQUENCE: 54

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80
```

```
Lys Glu Tyr Lys Cys Lys Val Ser Asn Lys Ala Leu Pro Ala Pro Ile
                85                  90                  95
Glu Lys Thr Ile Ser Lys Ala Lys Gly Gln Pro Arg Glu Pro Gln Val
            100                 105                 110
Tyr Thr Leu Pro Pro Ser Arg Glu Glu Met Thr Lys Asn Gln Val Ser
        115                 120                 125
Leu Thr Cys Leu Val Lys Gly Phe Tyr Pro Ser Asp Ile Ala Val Glu
    130                 135                 140
Trp Glu Ser Asn Gly Gln Pro Glu Asn Asn Tyr Asp Thr Thr Pro Pro
145                 150                 155                 160
Val Leu Asp Ser Asp Gly Ser Phe Phe Leu Tyr Ser Asp Leu Thr Val
                165                 170                 175
Asp Lys Ser Arg Trp Gln Gln Gly Asn Val Phe Ser Cys Ser Val Met
            180                 185                 190
His Glu Ala Leu His Asn His Tyr Thr Gln Lys Ser Leu Ser Leu Ser
        195                 200                 205
Pro Gly Gly Gly Gly Ser Ala Arg Gln Gly Glu His Cys Pro Leu
    210                 215                 220
Gly Pro Gly Arg Cys Cys Arg Leu His Thr Val Arg Ala Ser Leu Glu
225                 230                 235                 240
Asp Leu Gly Trp Ala Asp Trp Val Leu Ser Pro Arg Glu Val Gln Val
                245                 250                 255
Thr Met Cys Ile Gly Ala Cys Pro Ser Gln Phe Arg Ala Ala Asn Met
            260                 265                 270
His Ala Gln Ile Lys Thr Ser Leu His Arg Leu Lys Pro Asp Thr Val
        275                 280                 285
Pro Ala Pro Cys Cys Val Pro Ala Ser Tyr Asn Pro Met Val Leu Ile
    290                 295                 300
Gln Lys Thr Asp Thr Gly Val Ser Leu Gln Thr Tyr Asp Asp Leu Leu
305                 310                 315                 320
Ala Lys Asp Cys His Cys Ile
                325

<210> SEQ ID NO 55
<211> LENGTH: 322
<212> TYPE: PRT
<213> ORGANISM: Artificial Sequence
<220> FEATURE:
<223> OTHER INFORMATION: Fusion Protein

<400> SEQUENCE: 55

Gly Pro Ser Val Phe Leu Phe Pro Pro Lys Pro Lys Asp Thr Leu Met
1               5                   10                  15
Ile Ser Arg Thr Pro Glu Val Thr Cys Val Val Val Asp Val Ser His
            20                  25                  30
Glu Asp Pro Glu Val Lys Phe Asn Trp Tyr Val Asp Gly Val Glu Val
        35                  40                  45
His Asn Ala Lys Thr Lys Pro Arg Glu Glu Gln Tyr Asn Ser Thr Tyr
    50                  55                  60
Arg Val Val Ser Val Leu Thr Val Leu His Gln Asp Trp Leu Asn Gly
65                  70                  75                  80
Lys Glu Tyr Lys Cys Lys Val Ser Asn Lys Ala Leu Pro Ala Pro Ile
                85                  90                  95
Glu Lys Thr Ile Ser Lys Ala Lys Gly Gln Pro Arg Glu Pro Gln Val
            100                 105                 110
```

Tyr Thr Leu Pro Pro Ser Arg Glu Glu Met Thr Lys Asn Gln Val Ser
            115                 120                 125

Leu Thr Cys Leu Val Lys Gly Phe Tyr Pro Ser Asp Ile Ala Val Glu
130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Ala Arg Gln Gly Asp His Cys Pro Leu Gly Pro Gly Arg Cys
    210                 215                 220

Cys Arg Leu His Thr Val Arg Ala Ser Leu Glu Asp Leu Gly Trp Ala
225                 230                 235                 240

Asp Trp Val Leu Ser Pro Arg Glu Val Gln Val Thr Met Cys Ile Gly
                245                 250                 255

Ala Cys Pro Ser Gln Phe Arg Ala Ala Asn Met His Ala Gln Ile Lys
            260                 265                 270

Thr Ser Leu His Arg Leu Lys Pro Asp Thr Val Pro Ala Pro Cys Cys
        275                 280                 285

Val Pro Ala Ser Tyr Asn Pro Met Val Leu Ile Gln Lys Thr Asp Thr
    290                 295                 300

Gly Val Ser Leu Gln Thr Tyr Asp Asp Leu Leu Ala Lys Asp Cys His
305                 310                 315                 320

Cys Ile

<210> SEQ ID NO 56
<211> LENGTH: 348
<212> TYPE: PRT
<213> ORGANISM: Artificial Sequence
<220> FEATURE:
<223> OTHER INFORMATION: Fusion Protein

<400> SEQUENCE: 56

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

```
Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Gly Gly Gly Gln Gly Gly Gly
210                 215                 220

Gly Gln Gly Gly Gly Gln Gly Gly Gly Gln Ala Arg Gln Gly
225                 230                 235                 240

Asp His Cys Pro Leu Gly Pro Gly Arg Cys Cys Arg Leu His Thr Val
                245                 250                 255

Arg Ala Ser Leu Glu Asp Leu Gly Trp Ala Asp Trp Val Leu Ser Pro
            260                 265                 270

Arg Glu Val Gln Val Thr Met Cys Ile Gly Ala Cys Pro Ser Gln Phe
            275                 280                 285

Arg Ala Ala Asn Met His Ala Gln Ile Lys Thr Ser Leu His Arg Leu
            290                 295                 300

Lys Pro Asp Thr Val Pro Ala Pro Cys Cys Val Pro Ala Ser Tyr Asn
305                 310                 315                 320

Pro Met Val Leu Ile Gln Lys Thr Asp Thr Gly Val Ser Leu Gln Thr
                325                 330                 335

Tyr Asp Asp Leu Leu Ala Lys Asp Cys His Cys Ile
            340                 345

<210> SEQ ID NO 57
<211> LENGTH: 348
<212> TYPE: PRT
<213> ORGANISM: Artificial Sequence
<220> FEATURE:
<223> OTHER INFORMATION: Fusion Protein

<400> SEQUENCE: 57

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160
```

-continued

```
Tyr Asp Thr Thr Pro Pro Val Leu Asp Ser Asp Gly Ser Phe Phe Leu
                165             170             175

Tyr Ser Asp Leu Thr Val Asp Lys Ser Arg Trp Gln Gln Gly Asn Val
            180             185             190

Phe Ser Cys Ser Val Met His Glu Ala Leu His Asn His Tyr Thr Gln
        195             200             205

Lys Ser Leu Ser Leu Ser Pro Gly Gly Gly Gly Gln Gly Gly Gly
    210             215             220

Gly Gln Gly Gly Gly Gln Gly Gly Gly Gln Ala Arg Gln Gly
225             230             235             240

Glu His Cys Pro Leu Gly Pro Gly Arg Cys Cys Arg Leu His Thr Val
                245             250             255

Arg Ala Ser Leu Glu Asp Leu Gly Trp Ala Asp Trp Val Leu Ser Pro
            260             265             270

Arg Glu Val Gln Val Thr Met Cys Ile Gly Ala Cys Pro Ser Gln Phe
            275             280             285

Arg Ala Ala Asn Met His Ala Gln Ile Lys Thr Ser Leu His Arg Leu
        290             295             300

Lys Pro Asp Thr Val Pro Ala Pro Cys Cys Val Pro Ala Ser Tyr Asn
305             310             315             320

Pro Met Val Leu Ile Gln Lys Thr Asp Thr Gly Val Ser Leu Gln Thr
                325             330             335

Tyr Asp Asp Leu Leu Ala Lys Asp Cys His Cys Ile
            340             345

<210> SEQ ID NO 58
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 58

Gly Gly Gly Gly Ala
1               5
```